United States Patent
Hare et al.

(10) Patent No.: US 9,962,409 B2
(45) Date of Patent: May 8, 2018

(54) THERAPY USING CARDIAC STEM CELLS AND MESENCHYMAL STEM CELLS

(75) Inventors: Joshua Hare, Miami Beach, FL (US); Konstantinos Chatzistergos, Kos (GR)

(73) Assignee: Vestion, Inc., Miami, FL (US)

( * ) Notice: Subject to any disclaimer, the term of this patent is extended or adjusted under 35 U.S.C. 154(b) by 782 days.

(21) Appl. No.: 12/751,445

(22) Filed: Mar. 31, 2010

(65) Prior Publication Data
US 2010/0260727 A1    Oct. 14, 2010

Related U.S. Application Data

(63) Continuation-in-part of application No. PCT/US2008/078379, filed on Oct. 1, 2008.

(60) Provisional application No. 61/183,316, filed on Jun. 2, 2009, provisional application No. 60/976,663, filed on Oct. 1, 2007.

(51) Int. Cl.
| | | |
|---|---|---|
| *A61K 35/34* | (2015.01) | |
| *A61K 35/28* | (2015.01) | |
| *C12N 5/0775* | (2010.01) | |
| *A61K 35/12* | (2015.01) | |

(52) U.S. Cl.
CPC .............. *A61K 35/34* (2013.01); *A61K 35/28* (2013.01); *C12N 5/0663* (2013.01); *A61K 2035/124* (2013.01)

(58) Field of Classification Search
None
See application file for complete search history.

(56) References Cited

U.S. PATENT DOCUMENTS

| | | | |
|---|---|---|---|
| 6,387,369 B1 * | 5/2002 | Pittenger et al. | 424/93.7 |
| 6,930,222 B2 * | 8/2005 | Yu | 800/10 |
| 7,070,943 B2 | 7/2006 | Darzynkiewicz et al. | |
| 2004/0126879 A1 * | 7/2004 | Schneider et al. | 435/372 |
| 2011/0123500 A1 | 5/2011 | Anversa et al. | |
| 2012/0034595 A1 | 2/2012 | Phillips et al. | |
| 2014/0369976 A1 | 12/2014 | Hare et al. | |
| 2015/0316535 A1 | 11/2015 | Hare et al. | |
| 2016/0250261 A1 | 9/2016 | Chatzistergos et al. | |

FOREIGN PATENT DOCUMENTS

| | | |
|---|---|---|
| WO | 200006701 A1 | 2/2000 |
| WO | WO2006/039630 A2 | 4/2006 |
| WO | WO2008/054819 A2 | 5/2008 |
| WO | WO2008/058216 A2 | 5/2008 |
| WO | WO2014/093051 A2 | 6/2014 |

OTHER PUBLICATIONS

Baeltrami et al. Cell, vol. 114, 763-776, Sep. 19, 2003, C.*

Hou et al., "Transplantation of mesenchymal stem cells from human bone marrow improves damaged heart function in rats", International Journal of Cardiology, Elsevier Science Publishers, Amsterdam, NL, vol. 115, No. 2, Jan. 25, 2007 (Jan. 25, 2007), pp. 220-228, XP005658417.

Wenhui Jiang et al., "Homing and differentiation of mesenchymal stem cells delivered intravenously to ischemic myocardium in vivo: a time-series study", Pflügers Archiv—European Journal of Physiology, Springer, Berlin, DE, vol. 453, No. 1, Aug. 17, 2006 (Aug. 17, 2006), pp. 43-52, XP019443285.

Dai W et al., "Allogeneic mesenchymal stem cell transplantation in postinfarcted rat myocardium: Short- and long-term effects", Circlulation, Lippincott Williams & Wilkins, US, vol. 112, No. 2, Jul. 12, 2005 (Jul. 12, 2005), pp. 214-223, XP002462182.

Huang et al., "Transplantation of angiogenin-overexpressing mesenchymal stem cells synergistically augments cardiac function in a porcine model of chronic ischemia", Journal of Thoracic and Cardiovascular Surgery, Mosby-Year Book, Inc., St. Louis, MO, US, vol. 132, No. 6, Nov. 29, 2006 (Nov. 29, 2006), pp. 1329-1338, XP005752949.

Wang et al., "The roles of mesenchymal stem cells (MSCs) therapy in ischemic heart diseaes", Biochemical and Biophysical Research Communications, Academic Press Inc, Orlando, FL, US, vol. 359, No. 2, Jun. 9, 2007 (Jun. 9, 2007), pp. 189-193, XP022107148.

Li et al., "Bone marrow mesenchymal stem cells differentiate into functional cardiac phenotypes by cardiac microenvironment", Journal of Molecular and Cellular Cardiology, Academic Press, GB, vol. 42, No. 2, Jan. 24, 2007 (Jan. 24, 2007), pp. 295-303, XP005853927.

Toma C. et al., "Human mesenchymal stem cells differentiate to a cardiomyocyte phenotype in the adult murine heart", Circulation, Lippincott Williams & Wilkins, US, vol. 105, No. 1, Jan. 8, 2002 (Jan. 8, 2002), pp. 93-98, XP002984364.

European Patent Office, "Extended European Search Report" dated Feb. 24, 2012, pp. 1-13.

Enrichment of Pluripotent Stem Cell Derived Neural Crest Stem Cells and Further Differentiation to Peripheral Neurons, retrieved from https://www.miltenyibiotec.com/en/research-areas/stem-cell-research/es-and-ips-cells/~/media/Images/Products/Import/0007200/IM007298.ashx.

European Search Report and Written Opinion (Partial) for European Application No. 14858818.9 dated May 19, 2017.

Faucherre et al., The Heart's Content—renewalble Resources, Int'l J. of Cardiology (Oct. 6, 2012), 167 (4):1141-1146.

Holmes et al., "Preparation of Cells and Reagents for Flow Cytometry," Current Protocols in Immun.(2001), Unit 5.3:1-24.

(Continued)

*Primary Examiner* — Blaine Lankford
(74) *Attorney, Agent, or Firm* — Pepper Hamilton LLP

(57) ABSTRACT

Compositions comprising stem cells delivered into infarcted myocardium by endocardial injection, engraft and differentiate into myocytes, endothelial cells, and vascular smooth muscle, and do so without the requirement for survival enhancing modification. These cells engraft whether injected acutely (days) or late (months) after myocardial infarction, and the efficiency of engraftment correlates with the functional recovery of the heart. The stem cells also recruit endogenous cardiac precursor cells, reconstitute myocardial stem cell niches, and enhance endogenous cell differentiation into myocytes.

38 Claims, 26 Drawing Sheets

(56) References Cited

OTHER PUBLICATIONS

Lee et al., Derivation of Neural Crest Cells from Human Pluripotent Stem Cells, Nature Protocols, Nature Publishing Group, GB (Apr. 1, 2010), 5(4):688-701.
Medepalli et al., "A New Technique for Reversible permeabilization of live cells for intracellular delivery of quantum dots," Nanotech. (2013), 24(205101):1-13.
Oskouei et al., Increased Potency of Cardiac Stem Cells Compared with Bone Marrow Mesenchymal Stem Cells in Cardiac Repair, Stem Cells Translational Medicine (Feb. 7, 2012), 1(2):116-124.
Practical Flow Cytometry (Shapiro, John Wiley & Sons) (Feb. 25, 2005), 43.
Lam et al. Embroyic stem cell-derived cardiomyocytes harbor a subpopulation of niche-forming Sco-1progenitor cells, Mol. Cell. Biochem (Dec. 3, 2010) 349(1-2):69-76.
Lin et al. High-purity enrichment of functional cardiovascular cells from human iPS cells, Cardio. Res. (Aug. 2012) 95(3):327-335.
Dingar et al., "Anti-apoptotic Function of the E2F Transcription Factor 4 (E2F4)/p130, a Member of Retinoblastoma Gene Family in Cardiac Myocytes", Journal of Molecular and Cellular Cardiology (Sep. 15, 2012), 53(6):820-828.
European Patent Office, "Extended European Search Report", dated Mar. 16, 2016, pp. 1-10.
Hatzistergos et al., "Bone Marrow Mesenchymal Stem Cells Stimulate Cardiac Stem Cell Proliferation and Differentiation", Circulation Research (Oct. 1, 2010), 107(7):913-922.
Hatzistergos et al., "Abstract 19546: Retinoblastoma Regulates Cardiac and Mesenchymal Stem Cell Niches during Adult Heart Regeneration," Circulation (Nov. 20, 2012), 126:A19546.
International Search Report and Written Opinion for International Application No. PCT/US2013/072660 dated Jul. 1, 2014.
Sdek et al., "Assessment of Cardiomyocyte DNA Synthesis During Hypertrophy in Adult Mice", The Journal of Cell Biology: JCB (Aug. 8, 2011), 266(3):H1439-423.
Uosaki et al., "Direct Contact with Endoderm-Like Cells Efficiently Induces Cardiac Progenitors from Mouse and Human Pluripotent Stem Cells", Plos One (Oct. 1, 2012), 7(10):e46413.
Yang et al., "A Key Role for Telomerase Reverse Transcriptase Unit in Modulating Human Embryonic Stem Cells Proliferation, Cell Cycle Dynamics, and In Vitro Differentiation," Stem Cells (Jan. 17, 2008), 26(4) pp. 805-863.
Chatzistergos et al., "Abstract 18448: Ckit Marks Cardiac Neural Crest Progenitors in the Developing Mouse Heart," American Heart Association, Scientific Sessions and Resuscitation Science Symposium (2013), 128(22) pp. 1-20.
International Search Report and Written Opinion for International Application No. PCT/US2014/062939 dated Mar. 16, 2015.
Tamura et al., "Neural Crest-Derived Stem Cells Migrate and Differentiate Into Cardiomyocytes After Myocardial Infarction," Arterioscler Thromb Vasc Biol. (2011), 31(3) pp. 582-589.
Tomita et al., "Cardiac neural crest cells contribute to the dormant multipotent stem cell in the mammalian heart," J Cell Biology (2005), 170(7) pp. 1135-1146.

* cited by examiner

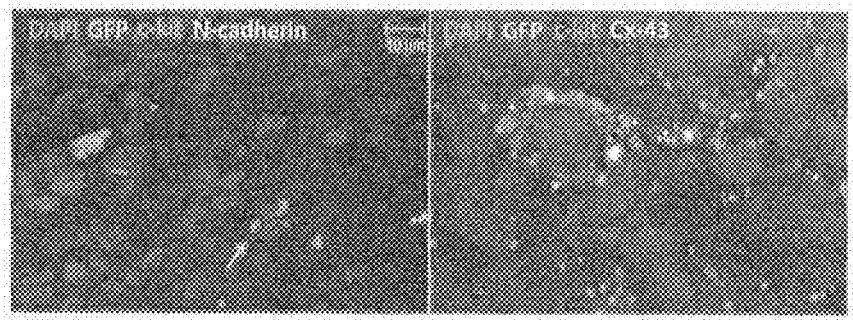

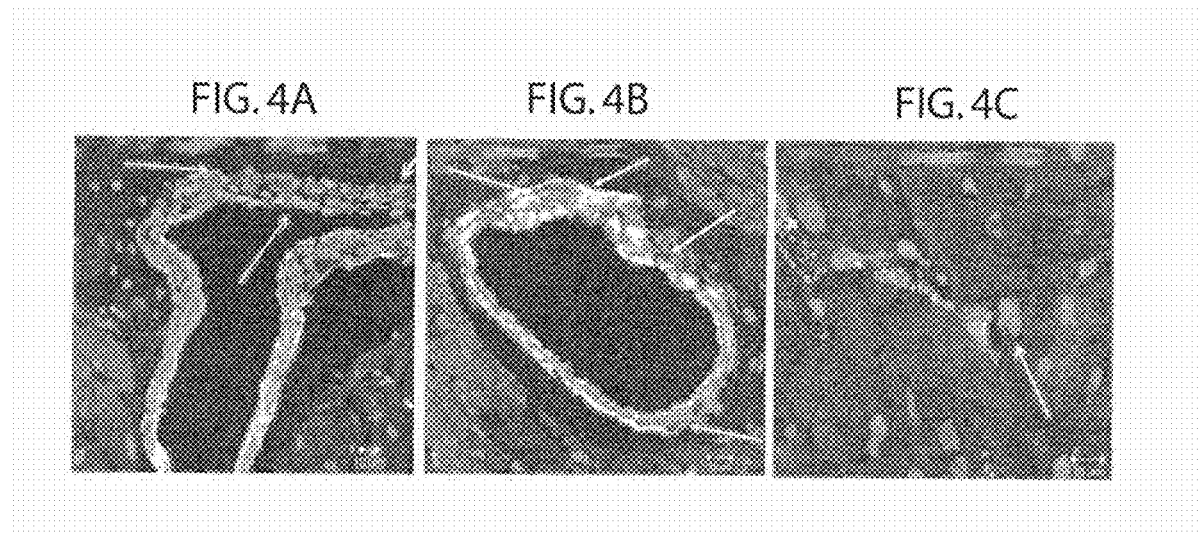
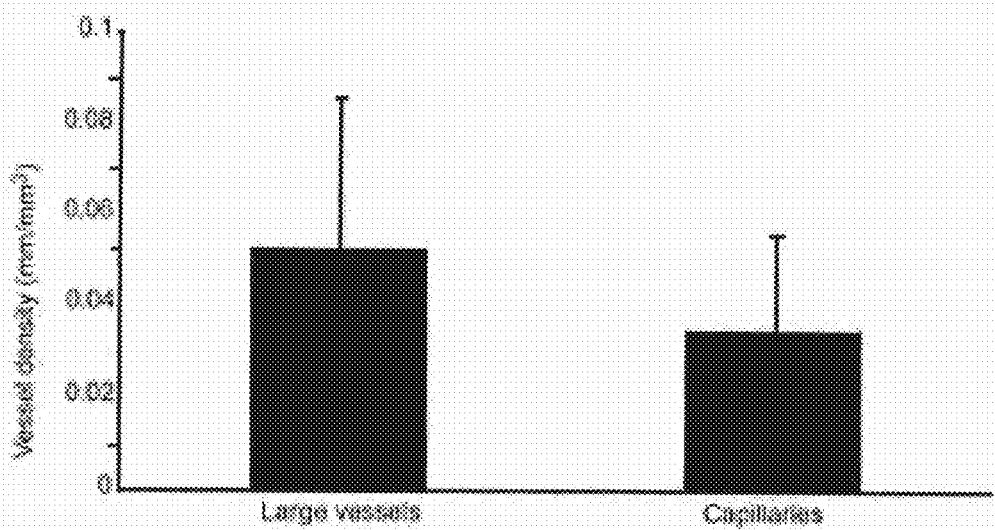
FIG. 4D
Border zone

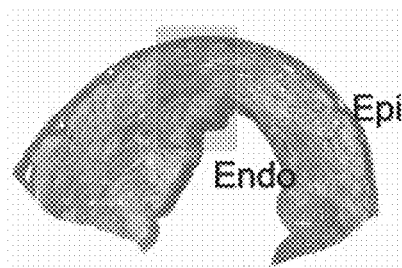
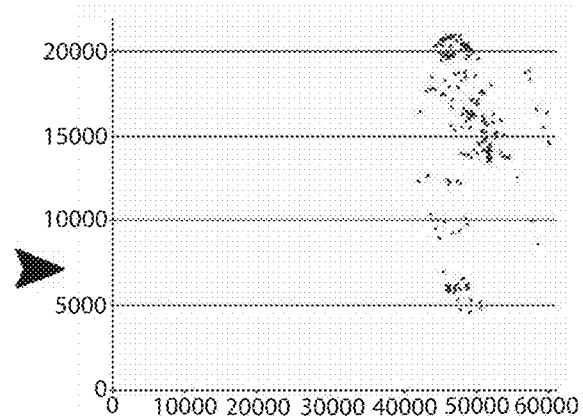
FIG. 6A　　　　　　　　FIG. 6B
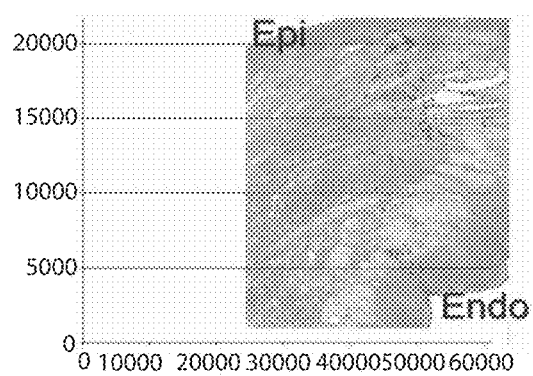
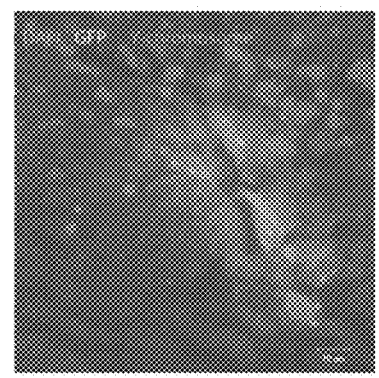
FIG. 6C　　　　　　　　FIG. 6D
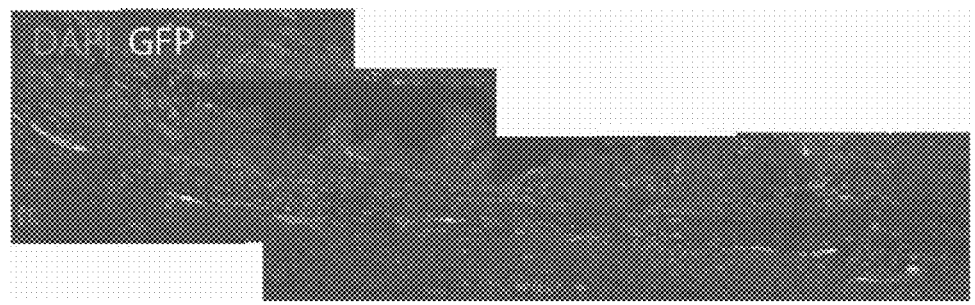
FIG. 6E FIG. 10A
FIG. 10B
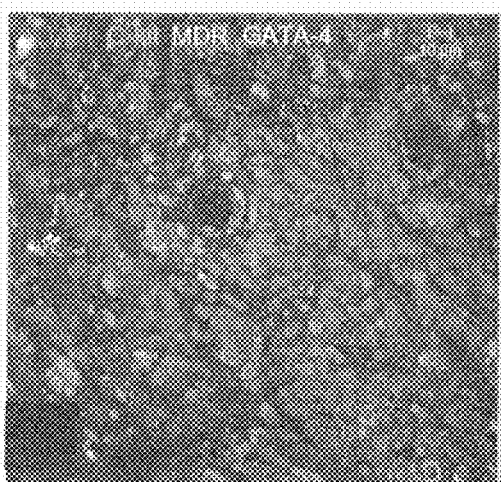
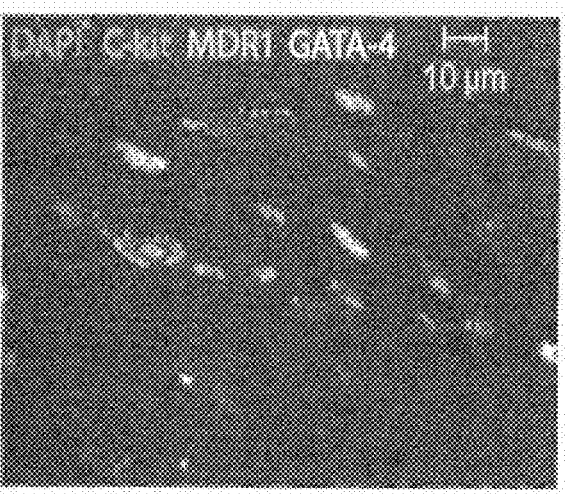
FIG. 10C
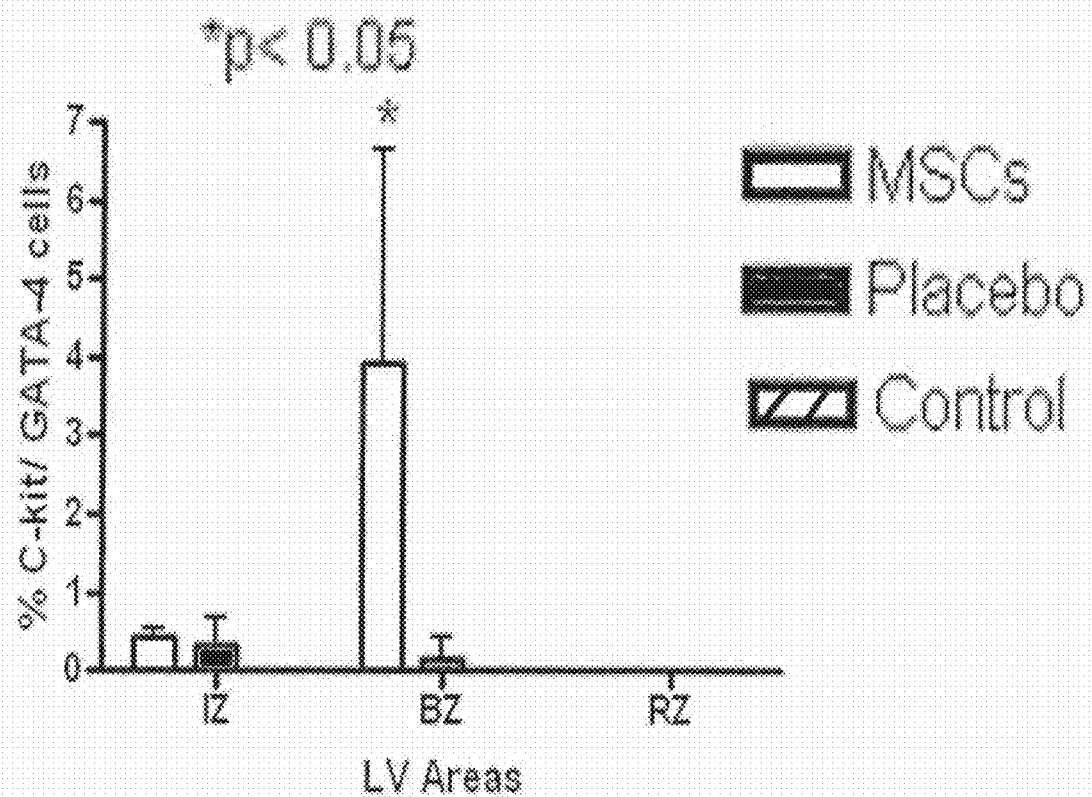

FIGURES 13A-13E
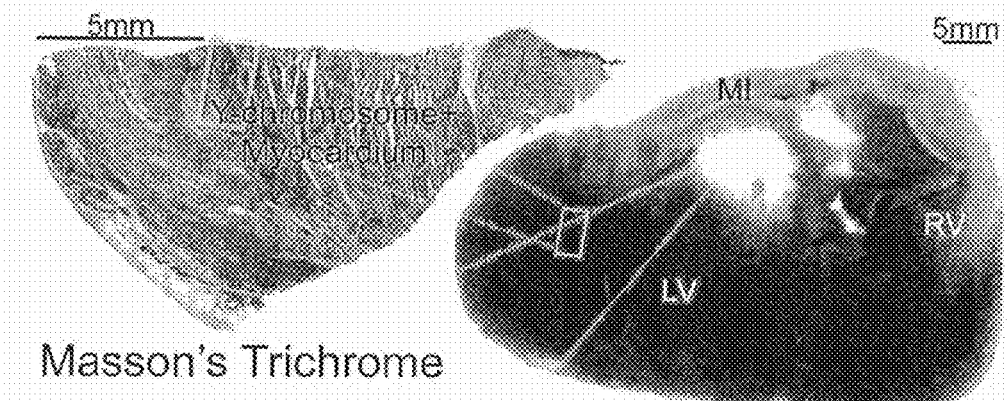
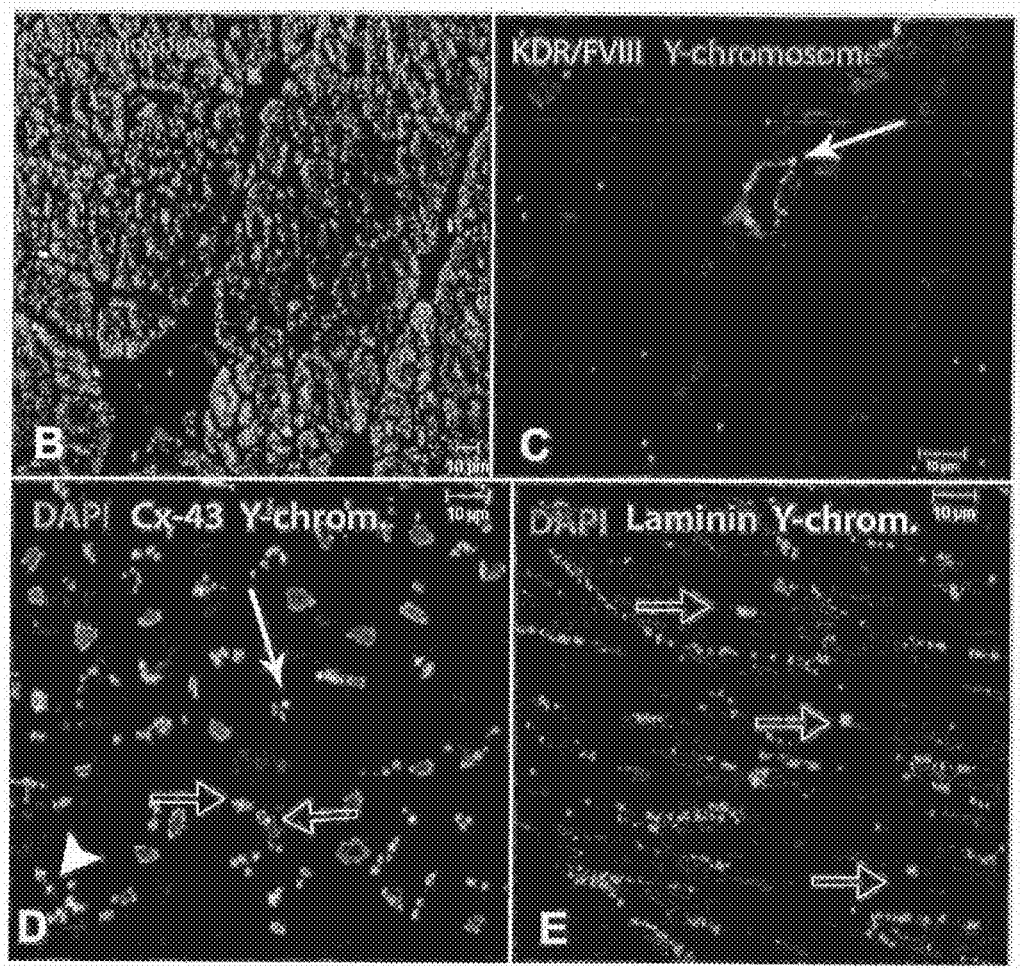

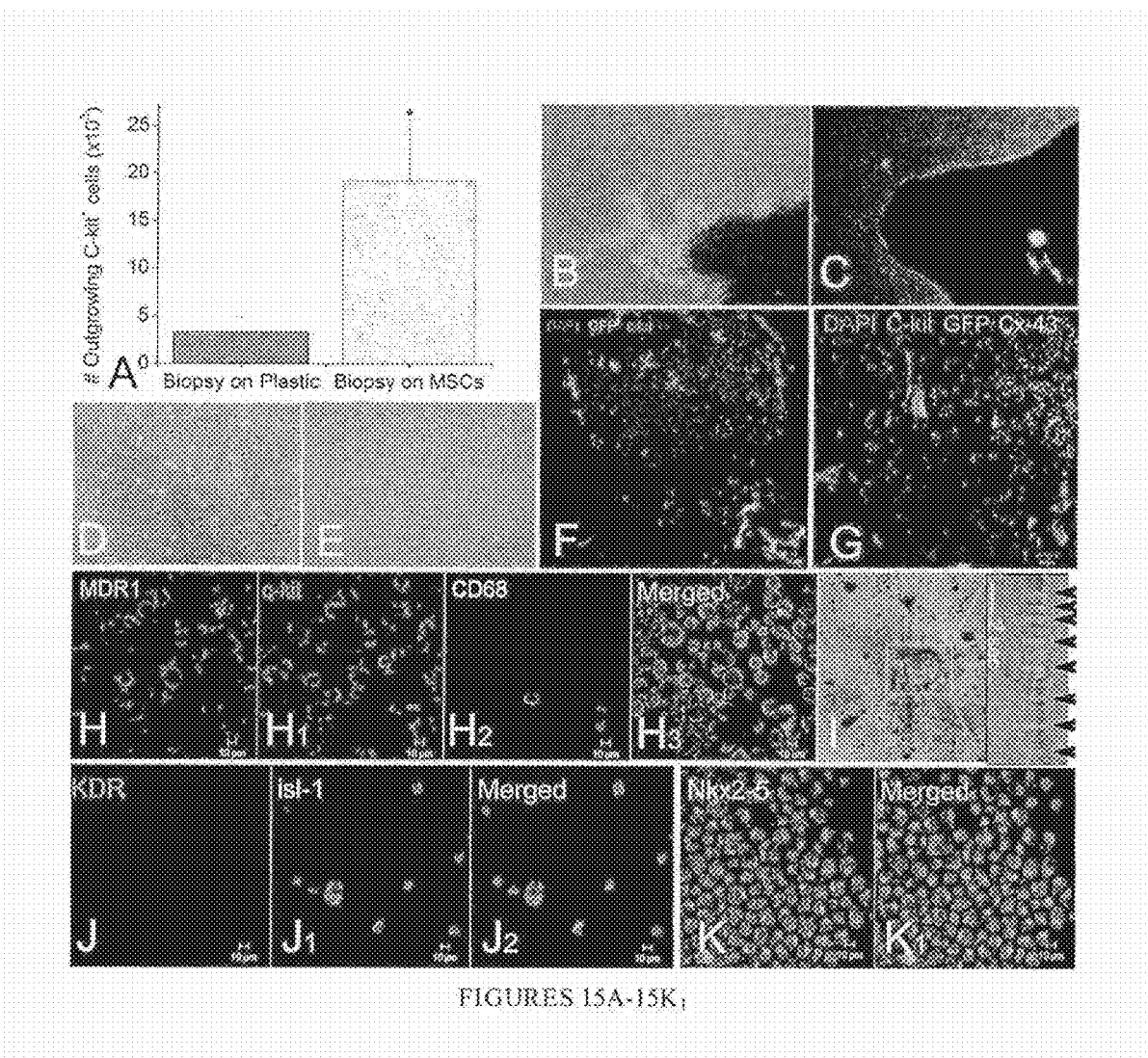
FIGURES 15A-15K1

THERAPY USING CARDIAC STEM CELLS AND MESENCHYMAL STEM CELLS

CROSS-REFERENCE TO RELATED APPLICATIONS

This application claims priority to U.S. Provisional Application No. 61/183,316 filed Jun. 2, 2009; and this application is a continuation-in-part of International Application No. PCT/US2008/78379, with an international filing date of Oct. 1, 2008, which claims priority to U.S. Provisional Application No. 60/976,663 filed Oct. 1, 2007, which are incorporated herein by reference in their entirety.

FIELD OF THE INVENTION

Embodiments of the invention relate to stem cell compositions and methods of tissue repair, and amplifying cardiac stem cells in vivo and in vitro.

BACKGROUND

Mesenchymal stem cells (MSCs) are bone marrow derived stem cells that have entered clinical trials for the treatment of various diseases including myocardial infarction and heart failure. In the past decade there have been extensive attempts to characterize the nature of bone marrow and cardiac precursor cell participation in recovery following ischemic injury to the heart. The idea that potentially reparative precursor cells exist in the marrow and in the heart has enormous clinical implications and has spurred a large number of clinical studies testing whether bone marrow or its derivatives exert clinical recovery following myocardial infarction (MI) and other types of cardiac injury. Despite this work proceeding both at clinical and basic levels, no consensus has emerged regarding the ability of these adult cell types to differentiate into cellular elements comprising the heart. To the contrary, there are diametrically opposing reports regarding this issue, and definitive proof of cellular engraftment is lacking in the clinical setting.

SUMMARY

This Summary is provided to present a summary of the invention to briefly indicate the nature and substance of the invention. It is submitted with the understanding that it will not be used to interpret or limit the scope or meaning of the claims.

This invention addresses a major limitation in the cardiac cell therapy area. This limitation involves using cardiac stem cells to treat patients with heart disease. Cardiac stem cells, while highly promising as a therapy, require a tissue biopsy and a long period of growth in the laboratory. MSCs can be used to accelerate the growth of CSCs in vitro or can be used to amplify CSCs in vivo, thereby eliminating the need for the tissue biopsy.

In an preferred embodiment, a method of treating heart disease and heart disorders in a patient comprises isolating stem cells from a patient or donor; purifying the stem cells and obtaining mesenchymal stem cells; administering to a patient's cardiac tissue, mesenchymal stem cells in a concentration effective to repair damaged cardiac tissue; and, treating heart disease and heart disorders.

In another preferred embodiment, the mesenchymal stem cells are autologous or donor derived.

In another preferred embodiment, the mesenchymal stem cells differentiate into multi-lineages. Preferably, the mesenchymal stem cells differentiate into at least one lineage of cardiac cells; more preferably, the mesenchymal stem cells differentiate into at least two lineages of cardiac cells; more preferably, the mesenchymal stem cells differentiate into three lineages of cardiac cells.

In another preferred embodiment, the lineages of cardiac cells are identified by at least one marker comprising cardiac transcription factor GATA-4; endothelial cell markers Factor VIII and KDR; vascular smooth muscle marker α-smooth muscle actin; or cardiomyocyte marker α-sarcomeric actinin.

In another preferred embodiment, the stem cells are obtained from bone marrow, circulation or tissues and organs.

In another preferred embodiment, the mesenchymal stem cells isolated from adult bone marrow cells.

In another preferred embodiment, the mesenchymal cells recruit endogenous cardiac stem cells, reconstitute myocardial stem cell niches and accelerate endogenous cell differentiation into myocytes.

In another preferred embodiment, the endogenous cardiac stem cells are identified by at least one marker comprising connexin-43, N-cadherin, c-kit$^{pos}$, CD3$^{neg}$, CD14$^{neg}$ and CD68$^{neg}$.

In another preferred embodiment, cardiac stem cells are autologous or donor derived.

In yet another preferred embodiment, the mesenchymal stem cell factors are administered to the patient.

In one preferred embodiment, a method of recruiting endogenous cardiac stem cells to damaged heart tissue comprises administering to the damaged heart tissue, purified mesenchymal stem cells; and, recruiting endogenous cardiac stem cells.

In a preferred embodiment, the mesenchymal stem cells are purified from adult bone marrow.

In another preferred embodiment, the mesenchymal stem cells are autologous, heterologous, syngeneic, allogeneic or xenogeneic.

In another preferred embodiment, the damage to heart tissue can be from any source or cause and comprises disease, physical damage, chemical damage, surgery, transplantation, or congenital defects.

In another preferred embodiment, the method of inducing and/or accelerating cardiac stem cell proliferation comprises isolating mesenchymal stem cells; co-culturing mesenchymal stem cells and cardiac stem cells in a concentration sufficient to induce and/or accelerate cardiac stem cells proliferation.

In another preferred embodiment, the cardiac stem cells differentiate into cardiac cells expressing at least one of MDR1 or GATA-4.

In another preferred embodiment, the cardiac stem cells are derived from an autologous or histocompatible tissue biopsy.

In another preferred embodiment, the isolated the mesenchymal cells are administered to a patient.

In another preferred embodiment, the mesenchymal cells and cardiac stem cells are autologous, heterologous, syngeneic, allogeneic or xenogeneic.

In yet another embodiment, the mesenchymal stem cells and cardiac stem cells are isolated from differing sources. Preferably, the cardiac stem cells are endogenous stem cells or donor derived. Cardiac stem cells are preferably identified by at least one marker comprising connexin-43, N-cadherin, c-kit$^{pos}$, CD3$^{neg}$, CD14$^{neg}$ and CD68$^{neg}$.

In another preferred embodiment, the mesenchymal cells are autologous stem cells and are administered to a patient in a therapeutically effective dose to recruit endogenous stem cells to damaged tissue.

In another preferred embodiment, the mesenchymal stem cell and endogenous cardiac stem cells are optionally isolated and cultured ex-vivo and administered to a patient.

In another preferred embodiment, a method of treating damaged cardiac tissue comprises administering mesenchymal stem cells to cardiac tissue; stimulating cardiac stem cell in vivo proliferation; and, treating damaged cardiac tissue.

In another preferred embodiment, soluble factors from cultured mesenchymal stem cells are administered to cardiac tissue. In a preferred embodiment, a mesenchymal stem cell factor stimulates the proliferation of cardiac stem cells in vivo.

In another preferred embodiment, an antibody or aptamer is specific, i.e. specifically binds a mesenchymal stem cell factor.

In another preferred embodiment, a mesenchymal stem cell factor stimulates the proliferation of cardiac stem cells in vitro.

In another preferred embodiment a composition comprises mesenchymal stem cells and cardiac stem cells. In another preferred embodiment, the composition comprises mesenchymal stem cells from one source, e.g. autologous, donor derived, etc; and/or cardiac stem cells from another source, e.g. autologous, donor derived etc.

In another preferred embodiment, a mesenchymal stem cell comprises a polynucleotide encoding for a therapeutic agent, chemokine, growth factor or ligands thereof.

Other aspects of the invention are described infra.

BRIEF DESCRIPTION OF THE DRAWINGS

FIG. 1A: Cardiac lineage commitment of $GFP^{pos}$ αMSC expressing GATA-4 (arrows) in the BZ of a treated heart 24 h after transplantation. FIG. 1B: Cardiac committed αMSC undergoing symmetric division in the infarct zone of a treated heart 72 h after transplantation. FIG. 1C: $GFP^{pos}$ αMSC undergoing asymmetric division within the infarct zone of a 72 h treated heart and giving rise to a cardiac committed ($GATA-4^{pos}$) and an uncommitted daughter cell. FIG. 1D: Endothelial lineage commitment of αMSCs 72 h after transplantation, indicated by the colocalization of GFP and KDR/factor VIII (arrows). FIG. 1E: Magnification of the lower right corner of FIG. 1C. FIG. 1F: vascular smooth muscle cell commitment of αMSCs 72 h after transplantation, as indicated by the co-localization of GFP with α-smooth muscle actin (arrows). FIG. 1G: Magnification of the lower right corner of FIG. 1E. Electrical coupling of αMSCs with surrounding cardiac tissue 24 h after transplantation, as indicated by the co-localization of GFP and Connexin-43. FIG. 1I: $GFP^{pos}$ cells in a regenerating zone (Rgz) 72 h after transplantation are expressing α-sarcomeric actinin (arrows) and are mechanically coupled by N-cadherin with the infarcted (IZ) and border zone (BZ).

FIGS. 2A to 2J are scans of photographs showing the regeneration of cardiac muscle, vasculature and stem cell niches. FIG. 2A: An immature $GFP^{pos}$ cardiac progenitor MSC expressing GATA-4 in the border zone of a treated heart 2 weeks after. Notice the adjoining $c-kit^{pos}$ CSC. FIG. 2B: Immature MSCs in the border zone of a 2 week treated heart, expressing α-sarcomeric actinin (arrows). FIG. 2C: Robust regeneration of the infarcted myocardium 2 weeks after transplantation, as demonstrated by the presence of Y-chromosome containing cardiac myocytes. FIG. 2D: New coronary vessel formation 2 weeks after transplantation, as indicated by the Y-chromosome containing endothelial cell (arrow). FIG. 2E: The chimeric myocardium consisted of mature cardiac myocytes, cardiac precursors and immature MSCs, all connected by connexin-43 with each other and the surrounding cardiac muscle (arrows). FIG. 2F: Definite cardiac myocyte differentiation of MSCs 2 weeks after transplantation, as indicated by the existence of Y-chromosome containing mature cardiac myocytes. FIG. 2G: Mobilization of c-kitpos cells at the sites of injury 2 weeks after transplantation. C-kit cells were found in clusters in close proximity to GFP cells. FIG. 2H: In contrast to the aMSCs treated animals, Placebo and control groups, showed significantly lower numbers of c-kit cells which were also isolated. FIGS. 2I, 2J: The mobilized c-kit cells, often were connected with N-cadherin and connexin-43 with each other, the surrounding cardiac tissue and with $GFP^{pos}$ cells, indicating cardiac stem cell niches reconstitution.

FIG. 3A is a graph showing the assessment of global LV function by cine-MR images showing significant increase in % ejection fraction in the αMSCs-treated group compared to placebo, at 2 months [16.9±1% increase in αMSCs, n=6, vs. 0.4±3.7% increase in placebo, n=4; *p=0.005] and 3 months after treatment [16.5±8% increase in αMSCs, n=6, vs. 5.5±4.6% decrease in placebo, n=4; †p=0.05]. FIGS. 3B, 3C are scans of photographs showing delayed contrast enhancement (DCE) MR images 3 months after experimental myocardial infarction (MI) (FIG. 3B) and same short axis view after 3 months of αMSCs therapy (FIG. 3C). Notice the development of new endocardial tissue at the BZ of the treated hearts (arrowheads). FIG. 3D is a graph showing the quantitation of infarct size by DCE MRI which showed a significant % decrease in scar size in αMSCs animals compared to placebo group at 2 months [21.9±7.3% decrease in αMSCs, n=6, vs. 1.1±5.5% increase in placebo n=4; *p=0.047 and 3 months after treatment [29.0±5.1% decrease in αMSCs, n=6, vs. 4.3±9.4% increase in placebo, n=4; †p=0.01]. FIGS. 3E, 3F are scans of photographs showing representative 4 mm-thick slices from the harvested hearts 12 weeks after MI, illustrating differences in LV diameter as well as in the extent of the scar size between the placebo and αMSCs-treated animals (FIGS. 3E and 3F respectively). FIG. 3G is a graph showing a plot of the peak circumferential strain (peak Ecc) of the endocardial wall over time, demonstrating significant improvements in regional contractility of the treated-hearts (negative peak Ecc denotes normal regional contraction), 8 and 12 weeks after αMSCs therapy (*p=0.001 vs. placebo). FIG. 3H is a graph showing improvement in contractility, evidenced by the absolute changes in peak Ecc, exhibited correlation with the absolute reduction in infarct size (Pearson's correlation: R=−0.97). FIG. 3I is a graph showing recovery in peak Ecc was strongly related to the aMSCs engraftment (R=−0.82). FIG. 3J is a scan of a photograph showing evidence of chimeric heart 12 weeks after transplantation, demonstrated by the presence of newly formed $GATA-4^{pos}/Y^{pos}$ mature CM.

FIGS. 4A to 4E show the regeneration of large and small coronary vessels following αMSC transplantation. FIGS. 4A-4C are scans of photographs showing confocal microscopy of large (FIG. 4A), middle-sized (FIG. 4B) and capillary vessels (FIG. 4C) in BZ of the αMSCs-treated group exhibiting $Y^{pos}$ cells into their structure. Large and middle-sized regenerated vessels co-localized with a smooth muscle actin and factor VIII. FIGS. 4D, 4E are graphs showing quantification of new vessel densities per unit volume of myocardium. The majority of the regenerated vessels were detected in the BZ of the αMSCs treated hearts.

FIGS. 6A-6E show Laser Scanning Cytometry (LSC) for mapping cell trafficking. FIGS. 6A-6C: Within 72 h post implantation, the GFP$^{pos}$ MSCs migrated from the endomyocardial site of injection to the infarcted subepicardial rim. No cells could be detected into the healthy surrounding myocardium indicating that MSCs trafficking was driven from damage signals. FIGS. 6D, 6E: Confocal Microscopy for anti-GFP and Y-chromosome was used to verify the detection of MSCs. Note that not all GFP$^{pos}$ cells are Y-chromosome$^{pos}$ and vice versa. The sensitivity of combined FISH/immunofluorescence detection was 45.5±2.1% of the total male cells.

FIG. 7A shows hematoxylin and eosin histological stain demonstrating the tracing of an injection site. FIG. 7B shows the presence of GFP$^{pos}$ cells within the same injection confirming the origin of the exogenous cells. FIGS. 7C, 7D: Connexin-43 and β1-Integrin were used as markers of homing and engraftment of the MSCs in the host myocardium. Notice the strong presence of c-kit cells in FIG. 7C.

FIG. 8A is a scan of a photograph showing immunofluorescence detection of the serine-10 phosphorylated Histone H3 (arrows) demonstrated the presence of mitotic αMSCs within an injection site, 72 h after transplantation. FIG. 8B: Co-localization of phospho-H3 and cleaved caspase-3 illustrated the premature chromatin condensation of an αMSC (arrow) and initiation of apoptosis 72 h after transplantation. Arrowhead shows an adjacent αMSC in mitosis. FIG. 8C: The number of apoptotic MSCs was counterbalanced by an analogous number of cells undergoing mitosis. Mitotic: phopshoHistone-H3$^{pos}$-GFP$^{pos}$: 1.2±0.7% of the total GFP$^{pos}$ cells at 24 h (n=1) and 1.3±0.4% at 72 h (n=3)]; Differentiating: GATA-4$^{pos}$-GFP$^{pos}$ 13.4±5.4% of the GFP-pos detected cells at 24 h (n=1) and 23.4±3.2%, at 72 hours (n=3); Apoptotic: caspase3$^{pos}$-GFP$^{pos}$: 0.31±1.0% at 24 h (n=1) and 1.0±0.6% at 72 h of the total GFPpos cells (n=3).

FIGS. 9A-9C show the dramatic recruitment of c-kit$^{pos}$ cells at the sites of injection. The c-kit cells were in clusters in the IZ (FIG. 9A) and BZ (FIG. 9B) of the treated hearts, but were mainly isolated in the healthy zones and/or the hearts of the nontreated animals (FIG. 9C). FIG. 9D is a graph showing the distribution of the c-kit cells within the different zones of the treated and untreated animals. IZ: 2.14±0.09 cells/mm$^2$ for the αMSCs group (n=3) vs. 0.04±0.02 cells/mm$^2$ for the placebo (n=3) and 0.09±0.04 cells/mm$^2$ for the control groups (n=3) respectively, *p<0.001; BZ: 0.74±0.12 cells/mm$^2$ for the αMSCs vs. 0.008±0.002 cells/mm$^2$ for the placebo and 0.013±0.003 cells/mm$^2$ for the control groups respectively, †p=0.001; RZ: 0.10±0.01 cells/mm$^2$ for the αMSCs vs. 0.002±0.001 cells/mm$^2$ for the placebo and 0.01±0.005 cells/mm$^2$ for the control groups respectively, *p<0.001.

FIGS. 10A to 10C show the stimulation of endogenous cardiac repair following αMSCs transplantation. FIGS. 10A, 10B: Besides the GFPpos MSCs, the regenerated CSC niches were containing clusters of c-kit$^{pos}$ cells which were co-localized with MDR1$^{pos}$ and GATA-4$^{pos}$. FIG. 10C: Quantification of the c-kit/GATA-4$^{pos}$ cardiac precursor cells between groups, demonstrated an active endogenous repair process in the MSCs treated animals which was commenced, but not restricted, in the BZ of the infarcted hearts. IZ: 0.4±0.08% of total c-kit$^{pos}$ cells in the αMSCs group (n=3) vs. 0.3±0.3% in the placebo (n=3) and none in the control (n=3), p=0.5; BZ: 3.9±1.6% in the αMSCs group vs. 0.28±0.14% in the placebo and none in the control, *p=0.038; RZ: none for any groups).

FIG. 11A: Transplanted αMSCs were found in clusters into the IZ and BZ of the host myocardium. Co-localization of BrdU with Y chromosome were used to confirm the origin of the allografts (arrows). Some of these cells had lost BrdU, presumably by mitotic division (arrowheads). FIG. 11B: Distribution of the αMSCs in the chronic infarcted myocardium. Cells were detected in the IZ and BZ but not the remote healthy zones. FIG. 11C: Newly formed cardiomyocytes were fully functional and integrated into the host myocardium; Demonstration of electrical coupling of αMSCs with the resident cardiomyocytes via the development of connexin-43 gap junctions (arrows).

(FIG. 12A) Significant decrease in the absolute value of the infarct size between MSCs and CCM-treated groups could be documented as early as 4 days post injections. By 8 weeks MSCs group exhibited diminished scar size (p<0.001) [absolute decrease (% of LV) 8.3±1.8% vs. 0.7±0.9% at day 4 (*p=0.018); 10.9±1.4% vs 3.3±1.7% at 2 weeks (*p=0.002); and 13±0.6% vs 2.3±1.3% at 8 weeks post injection (*p=0.002) between MSCs and CCM groups respectively]. (FIG. 12B) Ejection fraction was similar between the two groups through the 2 month study. However, by 2 weeks the MSCs group exhibited a significant recovery compared to post-MI (absolute decrease in EF between baseline and pre injection: 8.9±1.7% vs 12.3±3.7% (p=NS); baseline and 4d post-injection: 3.5±4.6% vs 11.1±2.4% (p=NS); baseline and 2 weeks post injection: 0.72±5.6 vs 9.2±2.5% (p=NS); baseline and 8 weeks post injection: 1.03±11.5% vs. 10.5±3.4% (p=NS) between MSCs and CCM-group respectively]. (†p=0.042 and †p=0.026 within MSCs group at 2 and 8 weeks respectively). Blue arrows indicate the day before injections. (FIGS. 12C, 12D) Delayed contrast hyperenhanced images of MSCs (FIG. 12C) and CCM (FIG. 12D) treated animals before and 8 weeks after injections. Notice the reduction in infarct size (yellow) in the MSCs but not the CCM-treated heart. Mean values±SEM (n=6 each at baseline, 4-days and 2 weeks, n=3 each at 8 weeks).

FIGS. 13A-13E: MSCs differentiate into new cardiac myocytes and vessels. (FIG. 13A) Masson's trichrome stained tissue section showing the context of a Y-chromosome containing region with respect to the infarct, 2 weeks after MSCs therapy. MSCs differentiated into new myocardial tissue at the border line of a previously infarcted region. The section is located ~8 mm far from the apex and ~30 mm from base of the LV. (FIG. 13B) Chimeric myocardium as indicated by the Y-chromosome containing myocytes in the cross-section of panel (FIG. 13A). (FIG. 13C) New coronary vessel formation 2 weeks after transplantation, as indicated by the Y-chromosome containing endothelial cell (arrow). (FIG. 13D) Chimeric myocardium consisted of mature cardiac myocytes (arrow), cardiac precursors (arrowhead) and immature MSCs (open arrow), all connected by connexin-43 with each other and the surrounding cardiac muscle. (FIG.

13E) Y-chromosome containing mature cardiomyocytes highlighted by Laminin (open arrows). [MI, myocardial infarct; LV, left ventricle; RV, right ventricle].

Figures 14A, 14B, 14C, 14D, 14E, 14F, 14G, 14H:
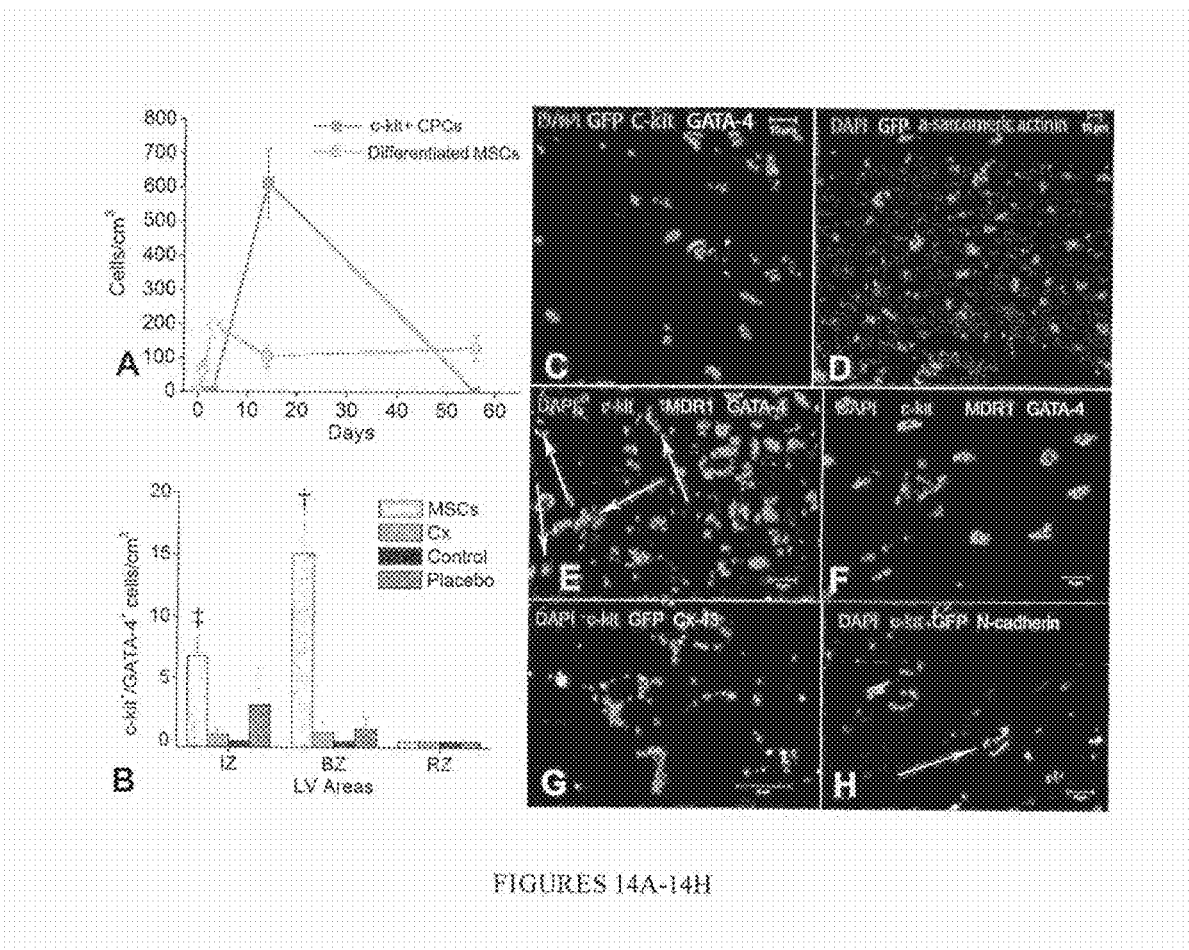
Figures 16A, 16B, 16C, 16D:
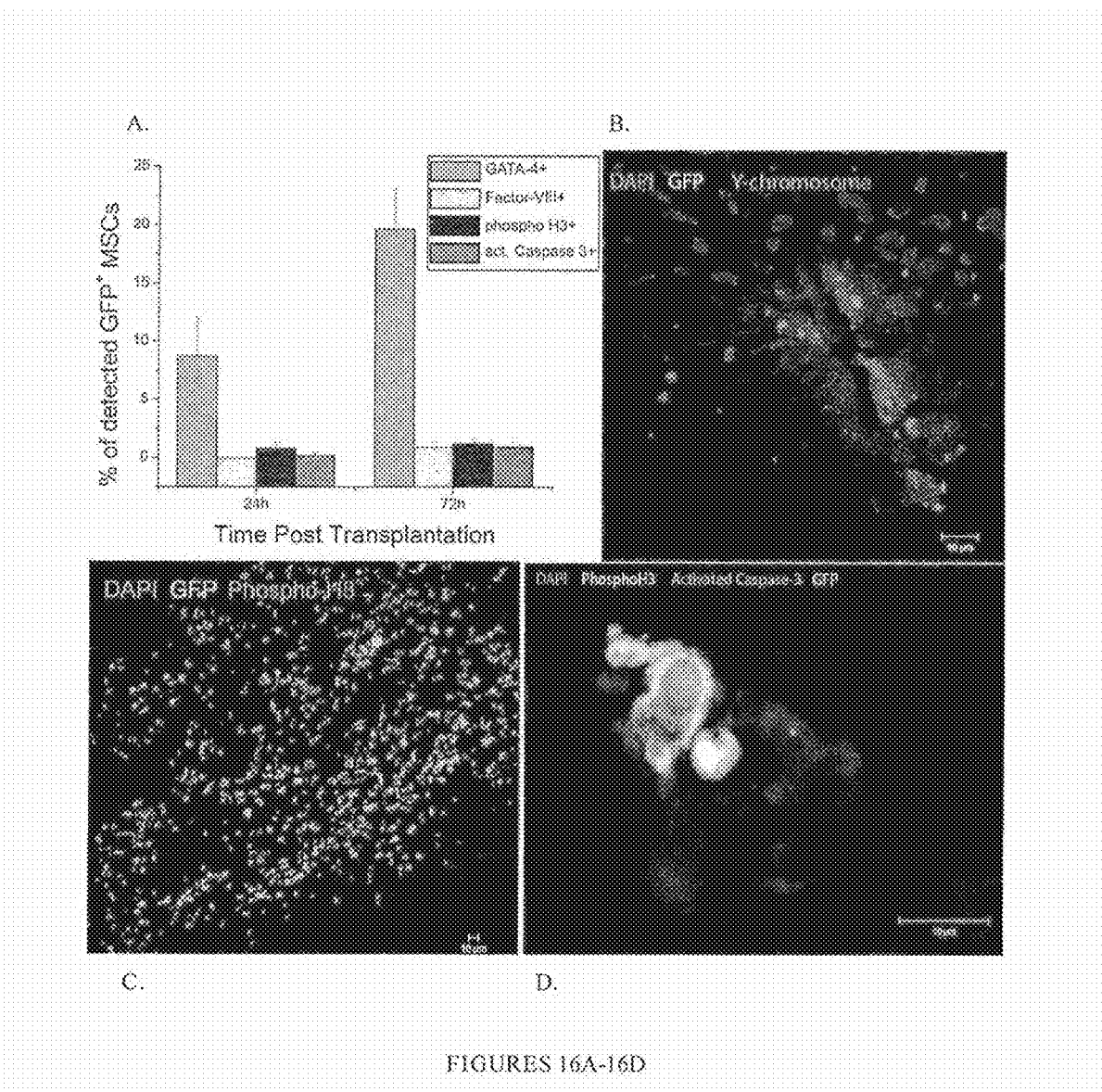
Figures 17A, 17B, 17C, 17D, 17E, 17F:
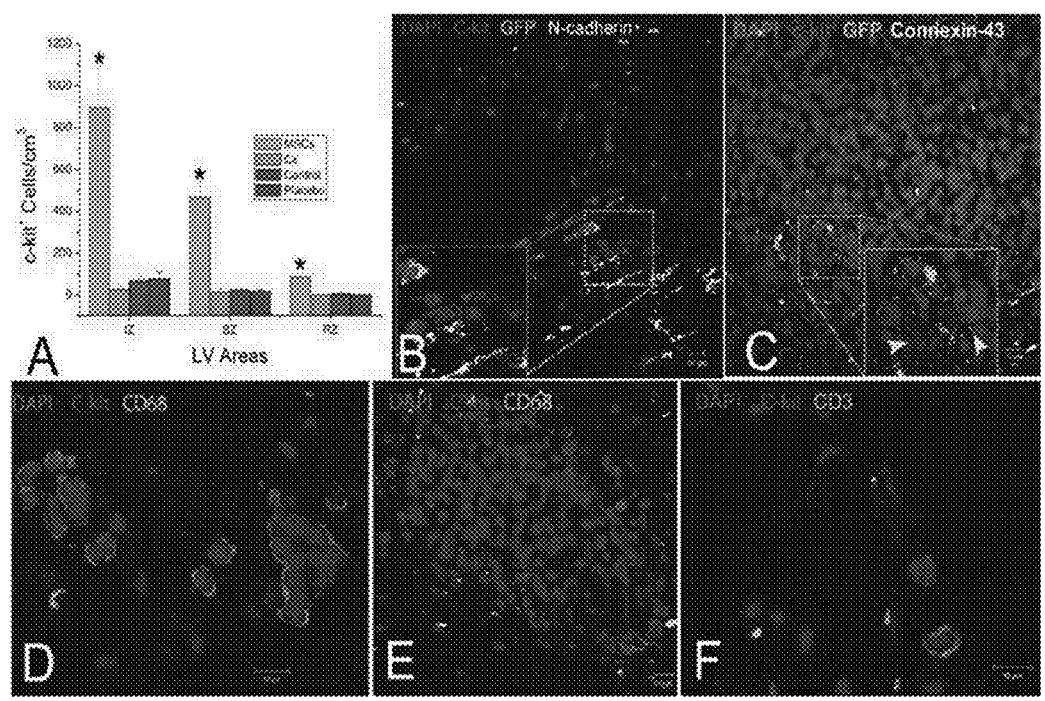

FIGS. 14A-14H. MSCs stimulate endogenous CPCs. (FIG. 14A) Differentiation of MSCs peaks 3-days postimplantation and the regenerated allografts are sustained for 2 months after transplantation [(see FIG. 16 for 24 h and 72 h values of GFP$^+$/GATA-4$^+$ MSCs); Y-chromosome$^+$ cardiomyocytes/cm$^3$: 75.3±24.9 in IZ and 135.5±64.1 in BZ at 2 weeks, and 76.7±33.2 in IZ and 185.01±64.3 in BZ at 8 weeks]. Two weeks later, MSCs stimulated a dramatic expansion of the endogenous c-kit$^+$ CPCs pool. (FIG. 14B) Quantification of c-kit$^+$/GATA-4$^+$ CPCs illustrated a significantly increased commitment of CPCs in the MSC-group. IZ: 6.8±1.7 GATA-4$^+$ CPCs/cm$^3$ in the MSCs (n=6) vs. 2.9±2.9 CPCs/cm$^3$ in the placebo (n=3), none in the control (n=3), and 0.5±0.5 CPCs/cm$^3$ in the CCM groups respectively, ‡p=0.019; BZ: 15.1±3.1 GATA-4$^+$ CPCs/cm$^3$ in the MSCs vs. 1.0±1.0 CPCs/cm$^3$ in the placebo, none in the control (n=3), and 0.7±0.7 CPCs/cm$^3$ in the CCM groups respectively, †p<0.0001; RZ: none for any groups). (FIGS. 14C, 14D) Co-localization of GFP with GATA-4 (FIG. 14C) and a-sarcomeric actinin (FIG. 14D) documents cardiac precursors of MSCs origin in the infarcted hearts which are found in close proximity to c-kit$^+$ CPCs (FIG. 14C). (FIG. 14E) Cluster of c-kit+ CPCs in an MSCs-treated heart; numerous CPCs are committed to cardiac lineage documented by GATA-4 and MDR-1 co-expression (arrows). (FIG. 14F) c-kit$^+$ cells were found isolated in non-MSC treated animals. (FIGS. 14G, 14H) MSCs interact with c-kit$^+$ CPCs by connexin-43 (FIG. 14F) and N-cadherin (FIG. 14G) connections, closely resembling cardiac stem cell niches.

FIGS. 15A-15K$_1$. Ex-vivo cardiac stem cell niche regeneration. (FIG. 15A) Culture of biopsies in a lawn of MSCs for 1 week facilitates a dramatic outgrowth of c-kit$^+$ CPCs. A mean of 19,158.82±6,505.7 vs 3,347.05±1,519.5 c-kit$^+$ cells were purified from biopsies cultured with and without MSCs respectively (*p=0.003). (FIG. 15B) A small number of cells outgrow from the biopsies cultured alone. (FIG. 15C) Organotypic cultures with MSCs have become confluent while, some GFP$^+$ MSCs have infiltrated the heart samples. (FIG. 15D, FIG. 15E). In contrast to the purified c-kit+ cells from the biopsy-alone which are large, quiescent cells with a macrophages morphology (FIG. 15E), co-cultures with MSCs egress small, semi-adherent CPCs that renew their population constantly (FIG. 15D). (FIGS. 15F, 15G), Immunostaining of the primary cell cultures documents interactions between GFP$^+$ MSCs and c-kit$^+$ cells as indicated by co-localization with CCM-43; these clusters closely resemble cardiac stem cell niches. (FIGS. 15H-15H$_3$) Cytospins of purified c-kit$^+$ CPCs, illustrating co-localization with MDR1, while lack of the surface marker CD68 from the vast majority of them excludes an inflammatory or mast cell phenotype. (FIG. 15I) Spontaneously contracting CPCs 3 days after co-culture in a transwell insert with NRCMs. Arrows indicate 8 contractions of the CPCs through a 12 sec period of time. (FIGS. 15J-15J$_2$) Expression of isl-1 in a subset of the CPCs. This information underlies that mechanisms of cell reprogramming (perhaps reactivation of the fetal gene program) are implicated in the MSCs-mediated recruitment of c-kit$^+$ CPCs. (FIGS. 15K-15K$_1$) Nkx2-5, is expressed in more than 90% of the CPCs. Mean values±SEM (n=19 each).

FIGS. 16A-16D. Fate of the allografts during the first 3 days after transplantation. (FIG. 16) The numbers of GFP$^+$ cells that were detected in the porcine LVs did not differ significantly between the first 24 and 72 h post-implantation. Histological quantification revealed that the 100×10$^6$ transplanted MSCs accounted for 1585.17±746.7 cells/cm$^3$ at 24 h and 1317.1±393.3 cells/cm$^3$ at 72 h. The extent of differentiating, mitotic and apoptotic MSCs during the first 3 days: myocytic (GFP$^+$/GATA-4$^+$): 63.7±23.9 cells/cm$^3$ at 24 h and 198.03±36.3 cells/cm$^3$ at 72 h; angiogenic (GFP$^+$/Factor VIII$^+$): none at 24 h, 0.94±0.4 cells/cm$^3$ at 72 h; mitotic: phopsho-H3$^+$/GFP$^+$: 0.8±0.5 cells/cm$^3$ at 24 h and 1.2±0.4 cells/cm$^3$ at 72 h]; apoptotic: activated caspase3$^+$/GFP$^+$: 0.2±0.2 cells/cm$^3$ at 24 h and 1.0±0.6 cells/cm$^3$ at 72 h. (FIG. 16B) The presence of exogenous cells within the host myocardium was confirmed by both GFP and chromosome co-localization. (FIG. 16C) Co-localization of phospho-H3 with GFP demonstrates the presence of mitotic MSCs within an injection site, 72 h after transplantation. (FIG. 16D) Colocalization of phospho-H3 and cleaved caspase-3 illustrates premature chromatin condensation of an MSC and initiation of apoptosis 72 h after transplantation. Arrow shows an adjacent MSC in mitosis. Mean Values±SEM (n=2 at 24 h, n=3 at 72 h).

FIGS. 17A-17F: MSCs stimulate amplification of endogenous c-kit+ CPCs 2 weeks after injection. (FIG. 17A) Recruitment of c-kit$^+$ CPCs in the MSCs-treated vs non-treated hearts and distribution of the c-kit cells within the different zones. IZ: 897.9±195.2 c-kit$^+$ cells/cm$^3$ for the MSCs group (n=6) vs. 78.1±32.6 cells/cm$^3$ for the placebo (n=3), 69.4±21.2 cells/cm$^3$ for the control and 27.1±18 cells/cm$^3$ for the Cx groups (n=3) respectively, *p<0.001; BZ: 467.5±70.6 cells/cm$^3$ for the MSCs vs. 18.9±5.9 cells/cm$^3$ for the placebo, 24.1±8.4 cells/cm$^3$ for the control and 16.1±11.3 cells/cm$^3$ for the Cx groups respectively, *p=0.001; RZ: 87.5±17.9 c-kit$^+$ cells/cm$^3$ for the MSCs vs. 0.5±0.5 cells/cm$^3$ for the placebo, 7.4±3.8 cells/cm$^3$ for the control and none for the Cx groups respectively, *p<0.001. (FIG. 17B) Endogenous c-kit$^+$ CPCs become functionally coupled with the infarcted myocardium as indicated by colocalization with N-cadherin (arrows). (FIG. 17C), A large cluster of c-kit$^+$ CPCs connected to each other and to adjacent GFP$^+$ MSCs by connexin-43. (FIGS. 17D-17F), Representative figures illustrating the non-inflammatory/mast cell phenotype of the c-kit+ CPCs. While clusters of CD68$^{pos}$/ckit$^{neg}$ cells could be detected in the non MSCs-treated hearts (FIG. 17C), the MSCs-treated hearts were rich in c-kit$^{pos}$/CD-68$^{neg}$ and CD3$^{neg}$ clusters of CPCs (FIG. 17D) Mean values±SEM (n=6 MSCs, 3 placebo, 3 Cx and 3 Control).

DETAILED DESCRIPTION

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the invention may be practiced without the theoretical aspects presented. Moreover, the theoretical aspects are presented with the understanding that Applicants do not seek to be bound by the theory presented.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, "heart disease" refers to any type of heart disease including cardiomyopathy, hypertrophic cardiomyopathy, dilated cardiomyopathy, atherosclerosis, coronary artery disease, ischemic heart disease, myocarditis, viral infection, wounds, hypertensive heart disease, valvular disease, congenital heart disease, myocardial infarction, congestive heart failure, arrhythmias, diseases resulting in remodeling of the heart, etc. Diseases of the heart can be due to any reason, such as for example, damage to cardiac tissue such as a loss of contractility (e.g., as might be demonstrated by a decreased ejection fraction).

Cardiac damage or disorder characterized by insufficient cardiac function includes any impairment or absence of a normal cardiac function or presence of an abnormal cardiac function. Abnormal cardiac function can be the result of disease, injury, and/or aging. As used herein, abnormal cardiac function includes morphological and/or functional abnormality of a cardiomyocyte, a population of cardiomyocytes, or the heart itself. Non-limiting examples of morphological and functional abnormalities include physical deterioration and/or death of cardiomyocytes, abnormal growth patterns of cardiomyocytes, abnormalities in the physical connection between cardiomyocytes, under- or over-production of a substance or substances by cardiomyocytes, failure of cardiomyocytes to produce a substance or substances which they normally produce, and transmission of electrical impulses in abnormal patterns or at abnormal times. Abnormalities at a more gross level include dyskinesis, reduced ejection fraction, changes as observed by echocardiography (e.g., dilatation), changes in EKG, changes in exercise tolerance, reduced capillary perfusion, and changes as observed by angiography. Abnormal cardiac function is seen with many disorders including, for example, ischemic heart disease, e.g., angina pectoris, myocardial infarction, chronic ischemic heart disease, hypertensive heart disease, pulmonary heart disease (cor pulmonale), valvular heart disease, e.g., rheumatic fever, mitral valve prolapse, calcification of mitral annulus, carcinoid heart disease, infective endocarditis, congenital heart disease, myocardial disease, e.g., myocarditis, dilated cardiomyopathy, hypertensive cardiomyopathy, cardiac disorders which result in congestive heart failure, and tumors of the heart, e.g., primary sarcomas and secondary tumors. Heart damage also includes wounds, such as for example, knife wound; biological (e.g. viral; autoimmune diseases) or chemical (e.g. chemotherapy, drugs); surgery; transplantation and the like.

"Myocardial ischemia" refers to a lack of oxygen flow to the heart which results in myocardial ischemic damage. As used herein, the phrase myocardial ischemic damage includes damage caused by reduced blood flow to the myocardium. Non-limiting examples of causes of myocardial ischemia and myocardial ischemic damage include: decreased aortic diastolic pressure, increased intraventricular pressure and myocardial contraction, coronary artery stenosis (e.g., coronary ligation, fixed coronary stenosis, acute plaque change (e.g., rupture, hemorrhage), coronary artery thrombosis, vasoconstriction), aortic valve stenosis and regurgitation, and increased right atrial pressure. Non-limiting examples of adverse effects of myocardial ischemia and myocardial ischemic damage include: myocyte damage (e.g., myocyte cell loss, myocyte hypertrophy, myocyte cellular hyperplasia), angina (e.g., stable angina, variant angina, unstable angina, sudden cardiac death), myocardial infarction, and congestive heart failure. Damage due to myocardial ischemia may be acute or chronic, and consequences may include scar formation, cardiac remodeling, cardiac hypertrophy, wall thinning, dilatation, and associated functional changes. The existence and etiology of acute or chronic myocardial damage and/or myocardial ischemia may be diagnosed using any of a variety of methods and techniques well known in the art including, e.g., non-invasive imaging (e.g., MRI, echocardiography), angiography, stress testing, assays for cardiac-specific proteins such as cardiac troponin, and clinical symptoms. These methods and techniques as well as other appropriate techniques may be used to determine which subjects are suitable candidates for the treatment methods described herein.

"Stem cell niche" refers to the microenvironment in which stem cells are found, which interacts with stem cells to regulate stem cell fate. (See, for example, Kendall Powell, *Nature* 435, 268-270 (2005). The word 'niche' can be in reference to the in vivo or in vitro stem cell microenvironment. During embryonic development, various niche factors act on embryonic stem cells to alter gene expression, and induce their proliferation or differentiation for the development of the fetus. Within the human body, stem cell niches maintain adult stem cells in a quiescent state, but after tissue injury, the surrounding microenvironment actively signals to stem cells to either promote self renewal or differentiation to form new tissues. Several factors are important to regulate stem cell characteristics within the niche: cell-cell interactions between stem cells, as well as interactions between stem cells and neighboring differentiated cells, interactions between stem cells and adhesion molecules, extracellular matrix components, the oxygen tension, growth factors, cytokines, and physiochemical nature of the environment including the pH, ionic strength (e.g. $Ca^{2+}$ concentration, metabolites like ATP are also important. The stem cells and niche may induce each other during development and reciprocally signal to maintain each other during adulthood. The niche also refers to specific anatomic locations that regulate how they participate in tissue generation, maintenance and repair. The niche saves stem cells from depletion, while protecting the host from over-exuberant stem-cell proliferation. It constitutes a basic unit of tissue physiology, integrating signals that mediate the balanced response of stem cells to the needs of organisms. Yet the niche may also induce pathologies by imposing aberrant function on stem cells or other targets. The interplay between stem cells and their niche creates the dynamic system necessary for sustaining tissues, and for the ultimate design of stem-cell therapies.

"Biological samples" include solid and body fluid samples. The biological samples used in the present invention can include cells, protein or membrane extracts of cells, blood or biological fluids such as ascites fluid or brain fluid (e.g., cerebrospinal fluid). Examples of solid biological samples include, but are not limited to, samples taken from tissues of the central nervous system, bone, breast, kidney, cervix, endometrium, head/neck, gallbladder, parotid gland, prostate, pituitary gland, muscle, esophagus, stomach, small intestine, colon, liver, spleen, pancreas, thyroid, heart, lung, bladder, adipose, lymph node, uterus, ovary, adrenal gland, testes, tonsils and thymus. Examples of "body fluid samples" include, but are not limited to blood, serum, semen, prostate fluid, seminal fluid, urine, saliva, sputum, mucus, bone marrow, lymph, and tears.

"Bone marrow derived progenitor cell" (BMDC) or "bone marrow derived stem cell" refers to a primitive stem cell with the machinery for self-renewal constitutively active. Included in this definition are stem cells that are totipotent, pluripotent and precursors. A "precursor cell" can be any cell in a cell differentiation pathway that is capable of differentiating into a more mature cell. As such, the term "precursor cell population" refers to a group of cells capable of developing into a more mature cell. A precursor cell population can comprise cells that are totipotent, cells that are pluripotent and cells that are stem cell lineage restricted (i.e. cells capable of developing into less than all hematopoietic lineages, or into, for example, only cells of erythroid lineage). As used herein, the term "totipotent cell" refers to a cell capable of developing into all lineages of cells. Similarly, the term "totipotent population of cells" refers to a composition of cells capable of developing into all lineages of cells. Also as used herein, the term "pluripotent cell" refers to a cell capable of developing into a variety (albeit not all) lineages and are at least able to develop into all hematopoietic lineages (e.g., lymphoid, erythroid, and thrombocytic lineages). Bone marrow derived stem cells contain two well-characterized types of stem cells. Mesenchymal stem cells (MSC) normally form chondrocytes and osteoblasts. Hematopoietic stem cells (HSC) are of mesodermal origin that normally give rise to cells of the blood and immune system (e.g., erythroid, granulocyte/macrophage, magakaryocite and lymphoid lineages). In addition, hematopoietic stem cells also have been shown to have the potential to differentiate into the cells of the liver (including hepatocytes, bile duct cells), lung, kidney (e.g., renal tubular epithelial cells and renal parenchyma), gastrointestinal tract, skeletal muscle fibers, astrocytes of the CNS, Purkinje neurons, cardiac muscle (e.g., cardiomyocytes), endothelium and skin.

As used herein, the term "autologous" is meant to refer to any material derived from the same individual to whom it is later to be re-introduced into the individual.

The term "xenogeneic cell" refers to a cell that derives from a different animal species than the animal species that becomes the recipient animal host in a transplantation or vaccination procedure.

The term "allogeneic cell" refers to a cell that is of the same animal species but genetically different in one or more genetic loci as the animal that becomes the "recipient host". This usually applies to cells transplanted from one animal to another non-identical animal of the same species.

The term "syngeneic cell" refers to a cell which is of the same animal species and has the same genetic composition for most genotypic and phenotypic markers as the animal who becomes the recipient host of that cell line in a transplantation or vaccination procedure. This usually applies to cells transplanted from identical twins or may be applied to cells transplanted between highly inbred animals.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

The terms "specific binding" or "specifically binding" when used in reference to the interaction of an antibody and a protein or peptide or aptamers, means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody. Thus, an antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

General Techniques

For further elaboration of general techniques useful in the practice of this invention, the practitioner can refer to standard textbooks and reviews in cell biology, tissue culture, embryology, and cardiophysiology.

With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, *Meth. Enzymol.* 225:900, 1993); Properties and uses of Embryonic Stem Cells: Prospects for Application to Human Biology and Gene Therapy (P. D. Rathjen et al., *Reprod. Fertil. Dev.* 10:31, 1998). With respect to the culture of heart cells, standard references include The Heart Cell in Culture (A. Pinson ed., CRC Press 1987), Isolated Adult Cardiomyocytes (Vols. I & II, Piper & Isenberg eds., CRC Press 1989), Heart Development (Harvey & Rosenthal, Academic Press 1998), I Left my Heart in San Francisco (T. Bennet, Sony Records 1990); and Gone with the Wnt (M. Mitchell, Scribner 1996).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Stem Cell Compositions

Embodiments of the invention provide for compositions comprising mesenchymal stem cells (MSCs) utilized, in some aspects, for the acceleration of the preparation of cardiac stem cells (CSCs.) Enhancing the CSCs in vitro will improve their utility. MSCs can also be used to proliferate CSCs in vivo. The CSCs proliferate and differentiate into cardiac cells, e.g. cardiomyocytes. Briefly, the results described herein show that injections of MSCs into pig hearts caused massive proliferation of CSCs. MSCs bind to and form complexes with CSCs, and cause their proliferation and differentiation into cardiac myocytes. Without wishing to be bound by theory, the cardiac stem cell proliferation can be due to a mesenchymal stem cell factor, a receptor ligand interaction between the MSCs and CSCs or other cells in the cardiac tissue, or combinations of both.

Figure 5:
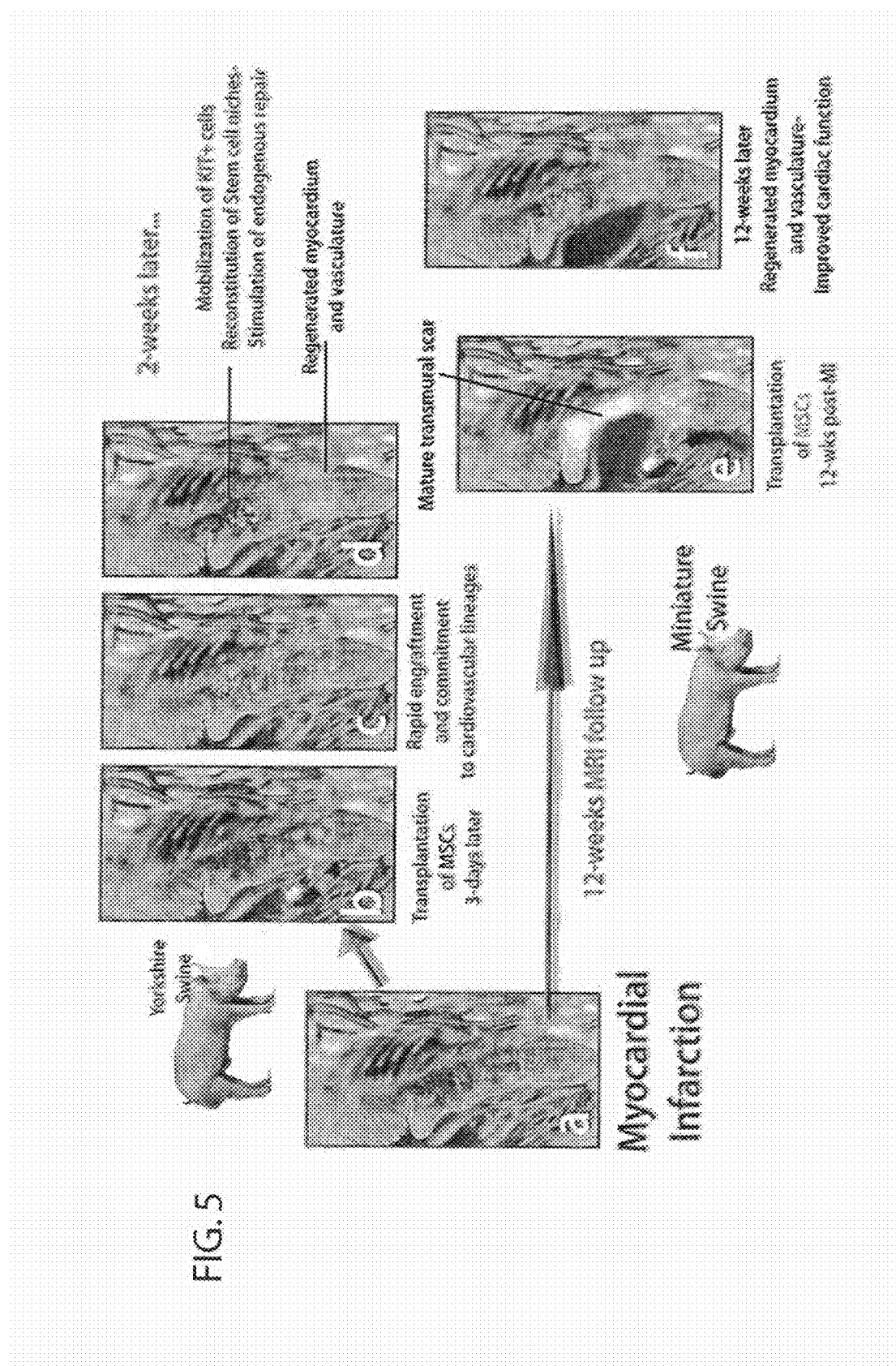
FIG. 5 is a schematic illustration showings summary of the in vivo results (panel insets a-f).
Figure 7A:
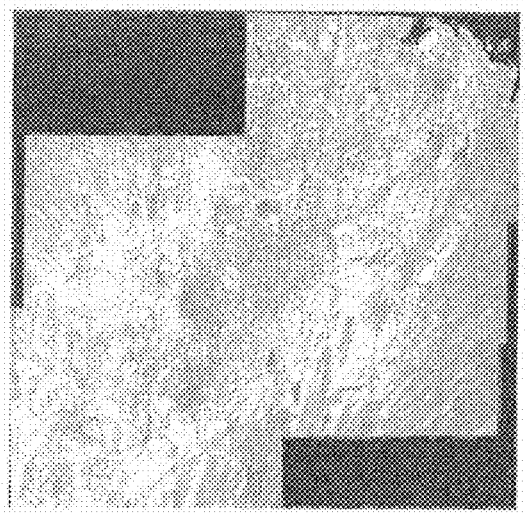
FIGS. 7A to 7D are scans of photographs showing robust retention of αMSCs two weeks after intramyocardial transplantation.
Figure 7B:
Figure 7C:
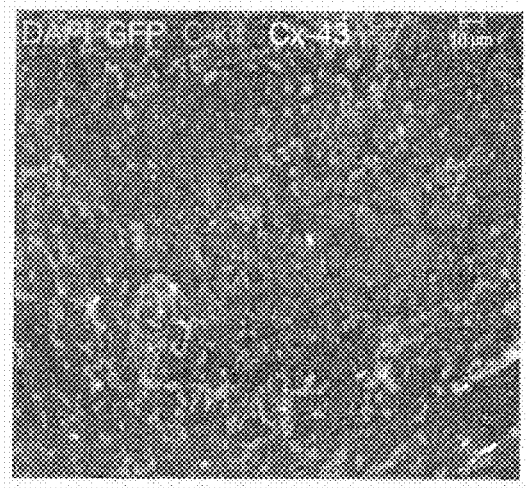
Figure 7D:
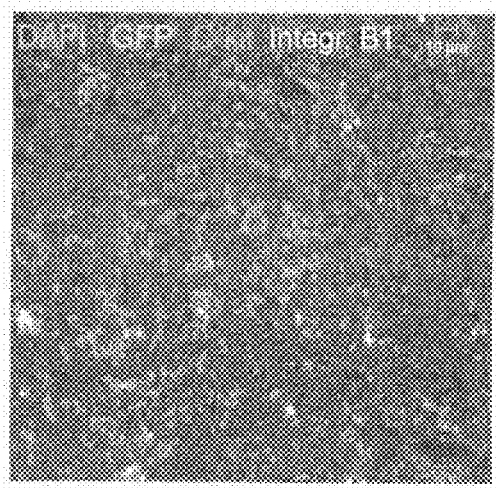

In order to determine whether MSCs had cardiac precursor potential or whether their therapeutic effect is exerted through paracrine effects, GFP labeled male allogeneic adult bone marrow derived mesenchymal stem cells (αMSCs) were injected into female pigs following myocardial infarction (MI) (FIG. 5). It was hypothesized that allogeneic adult bone marrow derived mesenchymal stem cells (αMSCs) were true adult precursor cells which could differentiate into three cardiac cell lineages, and that αMSCs participate in cardiac recovery by forming cell-cell interactions with existing myocardial elements including with endogenous precursor cells.

A stem cell is a cell from the embryo, fetus, or adult that has, under certain conditions, the ability to reproduce itself for long periods or, in the case of adult stem cells, throughout the life of the organism. It also can give rise to specialized cells that make up the tissues and organs of the body.

A pluripotent stem cell has the ability to give rise to types of cells that develop from the three germ layers (mesoderm, endoderm, and ectoderm) from which all the cells of the body arise. The only known sources of human pluripotent stem cells are those isolated and cultured from early human embryos and from fetal tissue that was destined to be part of the gonads.

An embryonic stem cell is derived from a group of cells called the inner cell mass, which is part of the early (4- to 5-day) embryo called the blastocyst. Once removed from the blastocyst the cells of the inner cell mass can be cultured into embryonic stem cells. These embryonic stem cells are not themselves embryos.

An adult stem cell is an undifferentiated (unspecialized) cell that occurs in a differentiated (specialized) tissue, renews itself, and becomes specialized to yield all of the specialized cell types of the tissue in which it is placed when transferred to the appropriate tissue. Adult stem cells are capable of making identical copies of themselves for the lifetime of the organism. This property is referred to as "self-renewal." Adult stem cells usually divide to generate progenitor or precursor cells, which then differentiate or develop into "mature" cell types that have characteristic shapes and specialized functions, e.g., muscle cell contraction or nerve cell signaling. Sources of adult stem cells include bone marrow, blood, the cornea and the retina of the eye, brain, skeletal muscle, dental pulp, liver, skin, the lining of the gastrointestinal tract and pancreas.

Stem cells from the bone marrow are the most-studied type of adult stem cells. They can be used clinically to restore various blood and immune components to the bone marrow via transplantation. There are currently identified two major types of stem cells found in bone marrow: hematopoietic stem cells (HSC, or $CD34^+$ cells) which are typically considered to form blood and immune cells, and stromal (mesenchymal) stem cells (MSC) that are typically considered to form bone, cartilage, muscle and fat. However, both types of marrow-derived stem cells recently have demonstrated extensive plasticity and multipotency in their ability to form the same tissues.

The marrow, located in the medullary cavity of bones, is the sole site of hematopoiesis in adult humans. It produces about six billion cells per kilogram of body weight per day. Hematopoietically active (red) marrow regresses after birth until late adolescence after which time it is focused in the lower skull vertebrae, shoulder and pelvic girdles, ribs, and sternum. Fat cells replace hematopoietic cells in the bones of the hands, feet, legs and arms (yellow marrow). Fat comes to occupy about fifty percent of the space of red marrow in the adult and further fatty metamorphosis continues slowly with aging. In very old individuals, a gelatinous transformation of fat to a mucoid material may occur (white marrow). Yellow marrow can revert to hematopoietically active marrow if prolonged demand is present such as with hemolytic anemia. Thus hematopoiesis can be expanded by increasing the volume of red marrow and decreasing the development (transit) time from progenitor to mature cell.

The marrow stroma consists principally of a network of sinuses that originate at the endosteum from cortical capillaries and terminate in collecting vessels that enter the systemic venous circulation. The trilaminar sinus wall is composed of endothelial cells; an underdeveloped, thin basement membrane, and adventitial reticular cells that are fibroblasts capable of transforming into adipocytes. The endothelium and reticular cells are sources of hematopoietic cytokines. Hematopoiesis takes place in the intersinus spaces and is controlled by a complex array of stimulatory and inhibitory cytokines, cell-to-cell contacts and the effects of extracellular matrix components on proximate cells. In this unique environment, lymphohematopoietic stem cells differentiate into all of the blood cell types. Mature cells are produced and released to maintain steady state blood cell levels. The system may meet increased demands for additional cells as a result of blood loss, hemolysis, inflammation, immune cytopenias, and other causes.

A "progenitor or precursor" cell occurs in fetal or adult tissues and is partially specialized; it divides and gives rise to differentiated cells. Researchers often distinguish precursor/progenitor cells from adult stem cells in that when a stem cell divides; one of the two new cells is often a stem cell capable of replicating itself again. In contrast when a progenitor/precursor cell divides, it can form more progenitor/precursor cells or it can form two specialized cells. Progenitor/precursor cells can replace cells that are damaged or dead, thus maintaining the integrity and functions of a tissue such as liver or brain.

Mesenchymal stem cells are the formative pluripotential blast cells found inter alia in bone marrow, blood, dermis and periosteum that are capable of differentiating into any of the specific types of mesenchymal or connective tissues (i.e. the tissues of the body that support the specialized elements; particularly adipose, osseous, cartilaginous, elastic, and fibrous connective tissues) depending upon various influences from bioactive factors, such as cytokines.

The isolation and purification of mesenchymal stem cells has been described in detail in the examples which follow. In one preferred embodiment, mesenchymal stem cells are isolated from bone marrow of adult patients. In one aspect, the cells are passed through a density gradient to eliminate undesired cell types. The cells are preferably, plated and cultured in appropriate media. In another preferred embodiment, the cells are cultured for at least one day, preferably, about three to about seven days, and removing non-adherent cells. The adherent cells are plated and expanded.

Other means for isolating and culturing stem cells useful in the present invention are well known. Umbilical cord blood is an abundant source of hematopoietic stem cells. The stem cells obtained from umbilical cord blood and those obtained from bone marrow or peripheral blood appear to be very similar for transplantation use. Placenta is an excellent readily available source for mesenchymal stem cells. Moreover, mesenchymal stem cells can be derivable from adipose tissue and bone marrow stromal cells and speculated to be present in other tissues. While there are dramatic qualitative and quantitative differences in the organs from which adult stem cells can be derived, the initial differences between the cells may be relatively superficial and balanced by the similar range of plasticity they exhibit.

Homogeneous human mesenchymal stem cell compositions are provided which serve as the progenitors for all mesenchymal cell lineages. MSCs are identified by specific cell surface markers which are identified with unique monoclonal antibodies. The homogeneous MSC compositions are obtained by positive selection of adherent marrow or periosteal cells which are free of markers associated with either hematopoietic cell or differentiated mesenchymal cells. These isolated mesenchymal cell populations display epitopic characteristics associated with only mesenchymal stem cells, have the ability to regenerate in culture without differentiating, and have the ability to differentiate into specific mesenchymal lineages when either induced in vitro or placed in vivo at the site of damaged tissue.

In order to obtain subject human mesenchymal stem cells, pluripotent mesenchymal stem cells are separated from other cells in the bone marrow or other MSC source. Bone marrow cells may be obtained from iliac crest, femora, tibiae, spine, rib or other medullary spaces. Other sources of human mesenchymal stem cells include embryonic yolk sac, placenta, umbilical cord, fetal and adolescent skin, and blood.

As discussed above, the mesenchymal stem cells can be isolated and purified by different methods. A preferred method has been described in detail in the examples section which follows. Other methods include, providing a tissue specimen containing mesenchymal stem cells, adding cells from the tissue specimen to a medium which contains factors that stimulate mesenchymal stem cell growth without differentiation and allows, when cultured, for the selective adherence of only the mesenchymal stem cells to a substrate surface, culturing the specimen-medium mixture, and removing the non-adherent matter from the substrate surface.

In a preferred embodiment, the mesenchymal stem cells are derived from one or sources comprising: autologous, heterologous, syngeneic, allogeneic or xenogeneic sources. These sources can include cell lines. As used herein, "source" refers to the animal in which these stem cells were obtained from, including human.

Differentiation of mesenchymal stem cells to the cardiac lineage is controlled by factors present in the cardiac environment. Local chemical, electrical and mechanical environmental influences alter pluripotent MSCs and convert the cells administered to the heart into the cardiac lineage.

In a preferred embodiment, mesenchymal stem cells differentiate into lineages of cells that make up the different heart tissues. In some embodiments, the lineages are identified by cardiac cell specific markers comprising cardiac transcription factor GATA-4, MDR1; endothelial cell markers Factor VIII and KDR; vascular smooth muscle marker α-smooth muscle actin; or cardiomyocyte marker α-sarcomeric actinin. For example, detection of expression of cardiomyocyte specific proteins is achieved using antibodies to, for example, myosin heavy chain monoclonal antibody MF 20 (MF20), sarcoplasmic reticulum calcium ATPase (SERCA1) (mnAb 10D1) or gap junctions using antibodies to connexin 43. Other markers for cardiomyocytes comprise cardiac troponin I (cTnI), cardiac troponin T (cTnT), sarcomeric myosin heavy chain (MHC), GATA-4, Nkx2.5, N-cadherin, β1-adrenoceptor β1-AR), ANF, the MEF-2 family of transcription factors, creatine kinase MB (CK-MB), myoglobin, or atrial natriuretic factor (ANF).

GATA transcription factor includes members of the GATA family of zinc finger transcription factors. GATA transcription factors are involved in the development of several mesodermally derived cell lineages. Preferably, GATA transcription factors include GATA-4 and/or GATA-6. The GATA-6 and GATA-4 proteins share high-level amino acid sequence identity over a proline-rich region at the amino terminus of the protein that is not conserved in other GATA family members.

In another preferred embodiment, soluble factors from mesenchymal stem cell cultures are administered to a patient with heart disease or disorders thereof. The factors are administered in an effective amount resulting in the localization, proliferation and maturation of cardiac stem cells into cells of the damaged heart tissue.

In another preferred embodiment, the mesenchymal cells are administered to a patient, for treating heart disease or disorders thereof. The cells can be autologous or donor derived. The administration of the mesenchymal stem cells results in the recruitment of cardiac stem cells to the damaged tissues, accelerated proliferation and differentiation of the cardiac stem cells and the repair of the damaged tissues. In preferred embodiments, the cardiac stem cells are endogenous stem cells. In other embodiments, the cardiac stem cells can be donor derived. The combinations of origins of the mesenchymal stem cells and cardiac stem cells can be in any combinations. For example, mesenchymal stem cells are autologous and the cardiac stem cells are endogenous. In other alternatives the mesenchymal stem cells are donor derived and the cardiac stem cells are endogenous. In another embodiment, the mesenchymal stem cells are autologous and the cardiac stem cells are donor derived. In other embodiments the mesenchymal stem cells comprise both autologous and donor derived cells and the cardiac stem cells comprise donor derived and endogenous cells. In other embodiments, soluble factors from mesenchymal stem cells are administered to the damaged heart tissue for recruiting, accelerating proliferation and differentiation of cardiac stem cells.

In a preferred embodiment, cardiac stem cells are identified by markers comprising: c-kit$^{pos}$, CD3$^{neg}$, CD14$^{neg}$ and CD68$^{neg}$.

Cardiac injury promotes tissue responses which enhance myogenesis using implanted MSCs. Thus, MSCs are introduced to the infarct zone to reduce the degree of scar formation and to augment ventricular function. New muscle is thereby created within an infarcted myocardial segment. MSCs are directly infiltrated into the zone of infarcted tissue. The integration and subsequent differentiation of these cells is characterized, as described above. Timing of intervention is designed to mimic the clinical setting where patients with acute myocardial infarction would first come to medical attention, receive first-line therapy, followed by stabilization, and then intervention with myocardial replacement therapy if necessary.

Of the four chambers of the heart, the left ventricle is primarily responsible for pumping blood under pressure through the body's circulatory system. It has the thickest myocardial walls and is the most frequent site of myocardial injury resulting from congestive heart failure. The degree of advance or severity of the congestive heart failure ranges from those cases where heart transplantation is indicated as soon as a suitable donor organ becomes available to those where little or no permanent injury is observed and treatment is primarily prophylactic.

The severity of resulting myocardial infarction, i.e. the percentage of muscle mass of the left ventricle that is involved can range from about 1 to about 80 percent. This represents affected tissue areas, whether as one contiguous ischemia or the sum of smaller ischemic lesions, having horizontal affected areas from about 1 cm$^2$ to about 6 cm$^2$ and a thickness of from 1-2 mm to 1-1.5 cm. The severity of the infarction is significantly affected by which vessel(s) is involved and how much time has passed before treatment intervention is begun.

The mesenchymal stem cells used in accordance with the invention are, in order of preference, autologous, allogeneic or xenogeneic, and the choice can largely depend on the urgency of the need for treatment. A patient presenting an imminently life threatening condition may be maintained on a heart/lung machine while sufficient numbers of autologous MSCs are cultured or initial treatment can be provided using other than autologous MSCs.

The MSC therapy of the invention can be provided by several routes of administration, including the following. First, intracardiac muscle injection, which avoids the need for an open surgical procedure, can be used where the MSCs are in an injectable liquid suspension preparation or where they are in a biocompatible medium which is injectable in liquid form and becomes semi-solid at the site of damaged myocardium. A conventional intracardiac syringe or a controllable arthroscopic delivery device can be used so long as the needle lumen or bore is of sufficient diameter (e.g. 30 gauge or larger) that shear forces will not damage the MSCs. The injectable liquid suspension MSC preparations can also be administered intravenously, either by continuous drip or as a bolus. During, open surgical procedures, involving direct physical access to the heart, all of the described forms of MSC delivery preparations are available options.

As a representative example of a dose range is a volume of about 20 to about 50 µl of injectable suspension containing about 10-40×10$^6$ MSCs/ml. The concentration of cells per unit volume, whether the carrier medium is liquid or solid remains within substantially the same range. The amount of MSCs delivered will usually be greater when a solid, "patch" type application is made during an open procedure, but follow-up therapy by injection will be as described above. The frequency and duration of therapy will, however, vary depending on the degree (percentage) of tissue involvement, as already described (e.g. 5-40% left ventricular mass).

In cases having in the 5-10% range of tissue involvement, it is possible to treat with as little as a single administration of one million MSCs in 20-50 µl of injection preparation. The injection medium can be any pharmaceutically acceptable isotonic liquid. Examples include phosphate buffered saline (PBS), culture media such as DMEM (preferably serum-free), physiological saline or 5% dextrose in water.

In cases having more in a range around the 20% tissue involvement severity level, multiple injections of 20-50 µl (10-40×10$^6$ MSCs/ml) are envisioned. Follow-up therapy may involve additional dosings.

In very severe cases, e.g. in a range around the 40% tissue involvement severity level, multiple equivalent doses for a more extended duration with long term (up to several months) maintenance dose aftercare may well be indicated.

In another embodiment, the isolated and culture expanded mesenchymal stem cells can be utilized for the implantation of various prosthetic devices. For example, using porous ceramic structures filled with culture-expanded human mesenchymal stem cells, and implanting these structures in areas where there is extensive tissue damage.

Additional Types of Stem Cells

In other embodiments, other stem cells can be used with the mesenchymal stem cells in the treatment of heart diseases and disorders thereof. Preferably, the stem cells are totipotent or pluripotent stem cells.

There are many undifferentiated cells found in vivo. Stem cells are undifferentiated immature cells, capable of self renewal (division without limit) and differentiation (specialization). These juvenile cells are abundant in a developing embryo; however, their numbers decrease as development progresses. By contrast, an adult organism contains limited number of stem cells which are confined to certain body compartments.

It is generally believed that stem cells are either: monopotent, bipotent or pluripotent. Monopotent and bipotent stem cells are more restricted in development and give rise to one or two types of specialized cells, respectively. In contrast, the pluripotent stem cells (PSCs) can differentiate into many different types of cells, giving rise to tissue (which constitute organs) or in the case of totipotent stem cells, the whole organism. Pluripotent stem cells, unlike monopotent or bipotent, are capable of multilineage differentiation, giving rise to a tissue which would consist of a collection of cells of different types or lineages.

According to the current understanding, a stem cell, such as a pluripotent stem cell, has the following four characteristics: (i) it is an undifferentiated cell—i.e. it is not terminally differentiated; (ii) it has the ability to divide without limit; (iii) it has the ability to give rise to differentiated progeny; and (iv) when it divides each daughter has a choice: it can either remain as stem cell like its parent or it can embark on a course leading to differentiation.

The hematopoietic stem cell is an example of a pluripotent stem cell which is found among marrow cells and gives rise to all the various blood cells (including leucocytes and erythrocytes). Hemopoietic stem cells can be extracted by isolation from (i) bone marrow, (ii) growth factor mobilized peripheral blood or (iii) cord blood (placenta). Recently, hemopoietic stem cells have been prepared from Embryonic Stem cells (ES), which are extracted from embryos obtained using in vitro fertilization techniques. These undifferentiated cells are capable of multi-lineage differentiation and reconstitution of all body tissue i.e. are totipotent.

There are a number of undifferentiated stem cells of the hemopoietic lineage. These include pluripotent stem cells (PSCs), lymphoid stem cells (LSCs) and myeloid stem cells known collectively as lymphohaematopoietic progenitor cells (LPCs). LSCs and myeloid stem cells are each formed by the differentiation of PSCs. Hence, LSCs and myeloid stem cells are more committed than PSCs. Examples of differentiated cells of the hemopoietic lineage include T cells, B cells, eosinophils, basophils, neutrophils, megakaryocytes, monocytes, granulocytes, mast cells, and lymphocytes.

Other stem cells include neural stem cells, multipotent stem cells that can generate neurons, atrocytes and oligodendrocytes (Nakafuku and Nakamura, 1995, *J. Neurosci Res.*, vol 41(2): 153-68; Anderson, 1994, *FASEB J.*, vol 8(10): 707-13; Morshead et al., 1994, *Neuron*, Vol 13(5): 1071-82). Skeletal muscle satellite cells are another type of stem cell, more specifically a distinct class of myogenic cells that are maintained as quiescent stem cells in the adult and can give rise to new muscle cells when needed (Bischoff, 1986, *Dev Biol.*, vol 115(1): 129-39). Other types of stem cells are epithelial stem cells, a subset of basal cells, and mesenchymal stem cells.

Embryonic stem (ES) cells are routinely used in the production of transgenic animals. ES cells have been shown to differentiate in vitro into several cell types including lymphoid precursors (Potocnik et al., 1994, *EMBO J.*, vol 13(22): 5274-83) and neural cells. ES cells are characterized by a number of stage-specific markers such as stage-specific embryonic markers 3 and 4 (SSEA-3 and SSEA-4), high molecular weight glycoproteins TRA-1-60 and TRA-1-81 and alkaline phosphatase (Andrews et al., 1984, *Hybridoma*, vol 3: 347-361; Kannagi et al., 1983, *EMBO J.*, vol 2: 2355-2361; Fox et al., 1984, *Dev. Biol.*, vol 103: 263-266; Ozawa et al., 1985, *Cell. Differ.*, vol 16: 169-173).

Various antigens are associated with undifferentiated and differentiated cells. The term "associated" here means the cells expressing or capable of expressing, or presenting or capable of being induced to present, or comprising, the respective antigen(s). Most undifferentiated cells and differentiated cells comprise Major Histocompatibility Complex (MHC) Class I antigens and/or Class II antigens. If these antigens are associated with those cells then they are called Class $I^+$ and/or Class $II^+$ cells. Each specific antigen associated with an undifferentiated cell or a differentiated cell can act as a marker. Hence, different types of cells can be distinguished from each other on the basis of their associated particular antigen(s) or on the basis of a particular combination of associated antigens. Examples of these marker antigens include the antigens CD34, CD19 and CD3. If these antigens are present then these particular cells are called $CD34^+$, $CD19^+$ and $CD3^+$ cells respectively. If these antigens are not present then these cells are called $CD34^-$, $CD19^-$ and $CD3^-$ cells respectively.

Some of the markers identified on myeloid stem cells comprise $CD34^+$ $DR^+$, $CD13^+$, $CD33^+$, $CD7^+$ and $TdT^+$ cells. PSCs are $CD34^+$ $DR^-$ $TdT^-$ cells (other useful markers being $CD38^-$ and $CD36^+$). LSCs are $DR^+$, $CD34^+$ and $TdT^+$ cells (also $CD38^+$). Embryonic stem cells express SSEA-3 and SSEA-4, high molecular weight glycoproteins TRA-1-60 and TRA-1-81 and alkaline phosphatase. They also do not express SSEA-1, the presence of which is an indicator of differentiation. Other markers are known for other types of stem cells, such as Nestein for neuroepithelial stem cells (*J. Neurosci*, 1985, Vol 5: 3310). Mesenchymal stem cells are also positive for SH2, SH3, CD29, CD44, CD71, CD90, CD106, CD120a and CD124, for example, and negative for CD34, CD45 and CD14.

Stem cells may further be isolated for transduction and differentiation using known methods. For example, in mice, bone marrow cells are isolated by sacrificing the mouse and cutting the leg bones with a pair of scissors. Stem cells may also be isolated from bone marrow cells by panning the bone marrow cells with antibodies which bind unwanted cells, such as $CD4^+$ and $CD8^+$ (T cells), $CD45^+$ (panB cells), GR-1 (granulocytes), and Iad (differentiated antigen presenting cells). For an example of this protocol see, Inaba et al., *J. Exp. Med.* 176:1693-1702 (1992).

In humans, $CD34^+$ hematopoietic stem cells can be obtained from a variety of sources including cord blood, bone marrow, and mobilized peripheral blood. Purification of $CD34^+$ cells can be accomplished by antibody affinity procedures. An affinity column isolation procedure for isolating $CD34^+$ cells is described by Ho et al., *Stem Cells* 13 (suppl. 3): 100-105 (1995). See also, Brenner, *Journal of Hematotherapy* 2: 7-17 (1993). Methods for isolating, purifying and culturally expanding mesenchymal stem cells are known.

Alternatively, or in addition, many cells can be identified by morphological characteristics. The identification of cells using microscopy, optionally with staining techniques is an extremely well developed branch of science termed histology and the relevant skills are widely possessed in the art.

Various techniques may be employed to separate the cells by initially removing cells of dedicated lineage. Monoclonal antibodies are particularly useful for identifying markers associated with particular cell lineages and/or stages of differentiation.

If desired, a large proportion of terminally differentiated cells may be removed by initially using a "relatively crude" separation. For example, magnetic bead separations may be used initially to remove large numbers of lineage committed cells. Desirably, at least about 80%, usually at least 70% of the total hematopoietic cells will be removed.

Procedures for separation may include but are not limited to, magnetic separation, using antibody-coated magnetic beads, affinity chromatography, cytotoxic agents joined to a monoclonal antibody or used in conjunction with a monoclonal antibody, including but not limited to, complement and cytotoxins, and "panning" with antibody attached to a solid matrix, e.g., plate, elutriation or any other convenient technique.

Techniques providing accurate separation include but are not limited to, flow cytometry, which can have varying degrees of sophistication, e.g., a plurality of color channels, low angle and obtuse light scattering detecting channels, impedance channels, etc.

Cardiotropic Agents: In some aspects of the invention, one or more "cardiotropic factors" can be included in the culture medium if it is desired by a user to differentiate the stem cells. These are factors that either alone or in combination enhance proliferation or survival of cardiomyocyte type cells, or inhibit the growth of other cell types. The effect may be due to a direct effect on the cell itself, or due to an effect on another cell type, which in turn enhances cardiomyocyte formation. For example, factors that induce the formation of hypoblast or epiblast equivalent cells, or cause these cells to produce their own cardiac promoting elements, all come within the rubric of cardiotropic factors.

Factors thought to induce differentiation of pluripotent stem cells into cells of the mesoderm layer, or facilitate further differentiation into cardiomyocyte lineage cells include the following: Nucleotide analogs that affect DNA methylation and altering expression of cardiomyocyte-related genes TGF-β ligands (exemplified by TGF-β1, TGF-β2, TGF-β3 and other members of the TGF-β superfamily). Ligands bind a TGF-β receptor activate Type I and Type II serine kinases and cause phosphorylation of the Smad effector. Morphogens like Activin A and Activin B (members of the TGF-β superfamily); Insulin-like growth factors (such as IGF II); Bone morphogenic proteins (members of the TGF-β superfamily, exemplified by BMP-2 and BMP-4); Fibroblast growth factors (exemplified by bFGF, FGF-4, and FGF-8) and other ligands that activate cytosolic kinase raf-1 and mitogen-activated proteins kinase (MAPK); Platelet-derived growth factor (exemplified by PDGFβ) Natriuretic factors (exemplified by atrial natriuretic factor (ANF), brain natriuretic peptide (BNP). Related factors such as insulin, leukemia inhibitory factor (LIF), epidermal growth factor (EGF), TGFα, and products of the cripto gene. Specific antibodies with agonist activity for the same receptors. Alternatively or in addition, the cells can be cocultured with cells (such as endothelial cells of various kinds) that secrete factors enhancing cardiomyocyte differentiation. Nucleotide analogs that affect DNA methylation (and thereby influence gene expression) can effectively be used to increase the proportion of cardiomyocyte lineage cells that emerge following initial differentiation. For example, it has been found that inclusion of 5-m-deoxy-cytidine in the culture medium increases the frequency of contracting cells in the population, and expression of cardiac αMHC.

Particularly effective combinations of cardiotropic agents include use of a morphogen like Activin A and a plurality of growth factors, such as those included in the TGF-β and IGF families during the early commitment stage, optionally supplemented with additional cardiotropins such as one or more fibroblast growth factors, bone morphogenic proteins, and platelet-derived growth factors.

During the elaboration of this invention, it was found that omitting factors such as insulin-like growth factor II (IGF II) and related molecules from the final stages of in vitro differentiation actually increased the levels of cardiac gene expression. In unrelated studies, IGF II has been found to decrease the levels of GSK3β in fibroblasts (Scalia et al., *J. Cell. Biochem.* 82:610, 2001). IGF II may therefore potentiate the effects of Wnt proteins present in the culture medium or secreted by the cells. Wnt proteins normally stabilize and cause nuclear translocation of a cytoplasmic molecule, β-catenin, which comprises a portion of the transcription factor TCF. This changes transcriptional activity of multiple genes. In the absence of Wnt, β-catenin is phosphorylated by the kinase GSK3β, which both destabilizes β-catenin and keeps it in the cytoplasm.

Since Wnt activators like IL-2 apparently limit cardiomyocyte differentiation, it is believed that culturing with Wnt antagonists can increase the extent or proportion of cardiomyocyte differentiation of hES cells. Wnt signaling can be inhibited by injection of synthetic mRNA encoding either DKK-1 or Crescent (secreted proteins that bind and inactivate Wnts) (Schneider et al., *Genes Dev.* 15:304, 2001), or by infection with a retrovirus encoding DKK-1 (Marvin et al., *Genes Dev.* 15:316, 2001). Alternatively, the Wnt pathway can be inhibited by increasing the activity of the kinase GSK3β, for example, by culturing the cells with factors such as IL-6 or glucocorticoids.

The combinations and amounts of such compounds that are effective for enriching cardiomyocyte production can be determined empirically by culturing undifferentiated or early differentiated embryonic stem cells or their progeny in a culture environment incorporating such factors, and then determining whether the compound has increased the number of cardiomyocyte lineage cells in the population according to the phenotypic markers listed below.

Following initial differentiation (and before or after a separation step, if employed), it is possible to increase the percentage of cardiomyocyte lineage cells by culturing in an environment containing a "cardiomyocyte enrichment agent". This is a factor in the medium or on a surface substrate that promotes the outgrowth of the desired cell type—either by facilitating proliferation of cardiomyocyte lineage cells, or by inhibiting the growth (or causing apoptosis) of cells of other tissue types. Some of the cardiotropic factors listed above are suitable for this purpose. Also suitable are certain compounds known beneficial to cardiomyocytes in vivo, or their analogs. Included are compounds capable of forming a high energy phosphate bond (such as creatine); an acyl group carrier molecule (such as carnitine); and a cardiomyocyte calcium channel modulator (such as taurine).

Cardiomyocyte specific markers comprise: Cardiac troponin I (cTnI), a subunit of troponin complex that provides a calcium-sensitive molecular switch for the regulation of striated muscle contraction. Cardiac troponin T (cTnT) Atrial natriuretic factor (ANF), a hormone expressed in developing heart and fetal cardiomyocytes but down-regulated in adults. It is considered a good marker for cardiomyocytes because it is expressed in a highly specific manner in cardiac cells but not skeletal myocytes. The cells will also typically express at least one (and often at least 3, 5, or more) of the following markers: sarcomeric myosin heavy chain (MHC) Titin, tropomyosin, α-actinin, and desmin, GATA-4, a transcription factor that is highly expressed in cardiac mesoderm and persists in the developing heart. It regulates many cardiac genes and plays a role in cardiogenesis Nkx2.5, a cardiac transcription factor expressed in cardiac mesoderm during early mouse embryonic development, which persists in the developing heart. MEF-2A, MEF-2B, MEF-2C, MEF-2D; transcription factors that are expressed in cardiac mesoderm and persist in developing heart N-cadherin, which mediates adhesion among cardiac cells Connexin 43, which forms the gap junction between cardiomyocytes. β1-adrenoceptor (β1-AR) creatine kinase MB (CK-MB) and myoglobin, which are elevated in serum following myocardial infarction. Other markers that may be positive on cardiomyocytes and their precursors include α-cardiac actin, early growth response-I, and cyclin D2.

Tissue-specific markers can be detected using any suitable immunological technique—such as flow immunocytochemistry or affinity adsorption for cell-surface markers, immunocytochemistry (for example, of fixed cells or tissue sections) for intracellular or cell-surface markers, Western blot analysis of cellular extracts, and enzyme-linked immunoassay, for cellular extracts or products secreted into the medium. Expression of an antigen by a cell is said to be antibody-detectable if a significantly detectable amount of antibody will bind to the antigen in a standard immunocytochemistry or flow cytometry assay, optionally after fixation of the cells, and optionally using a labeled secondary antibody or other conjugate (such as a biotin-avidin conjugate) to amplify labeling.

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. See U.S. Pat. No. 5,843,780 for details of general technique. Sequence data for other markers listed in this disclosure can be obtained from public databases such as GenBank (URL www.ncbi.nlm.nih.gov:80/entrez). Expression at the mRNA level is said to be detectable according to one of the assays described in this disclosure if the performance of the assay on cell samples according to standard procedures in a typical controlled experiment results in clearly discernable hybridization or amplification product. Expression of tissue-specific markers as detected at the protein or mRNA level is considered positive if the level is at least 2-fold, and preferably more than 10- or 50-fold above that of a control cell, such as an undifferentiated pluripotent stem cell or other unrelated cell type.

Once markers have been identified on the surface of cells of the desired phenotype, they can be used for immunoselection to further enrich the population by techniques such as immunopanning or antibody-medicated fluorescence-activated cell sorting.

Gene Therapy

In some preferred embodiments, the mesenchymal stem cells comprise therapeutic genes for delivery into the body, such as for example, the heart. In some embodiments, the therapeutic gene is a transgene. For example, the delivery cells—e.g. the mesenchymal stem cells are removed from the body, and a therapeutic transgene is introduced into them via vehicles well known to those skilled in the art such as those used in direct-gene-transfer methods. For example, while still in the laboratory, the genetically modified cells are tested and then allowed to grow and multiply and, finally, are infused back into the patient. Alternatively, allogeneic cells that bear normal, endogenous genes can reverse a deficiency in a particular target tissue. Use of cells bearing either transgenes or normal, endogenous genes is referred to herein as gene therapy.

Gene therapy using genetically modified cells offers several unique advantages over direct gene transfer into the body. First the addition of the therapeutic transgene to the delivery cells takes place outside the patient, which allows the clinician an important measure of control because they can select and work only with those cells that both contain the transgene and produce the therapeutic agent in sufficient quantity.

In some embodiments, the mesenchymal stem cells express stem cell recruiting factors, growth factors, therapeutic factors, endogenous factors such as, for example, cardiac troponin I (cTnI), cardiac troponin T (cTnT), atrial natriuretic factor (ANF), and the like. In view of the foregoing, the methods according to the present invention are useful for targeting a gene of interest (either a transgene or an endogenous gene) to a tissue in a mammal by introducing a cell comprising the gene of interest to the mammal. Such methods are useful for treating a disease characterized by a deficiency in a gene product in a mammal by administering a cell comprising a functional gene encoding the gene product into the mammal and administering a glycoconjugate to the mammal. Stem cells may be used as a vehicle for delivering genes to specific tissues in the body. Stem cell-based therapies are a major area of investigation in cancer research.

Embodiments of the invention further provide localizing of transfused cells such as stem cells to provide a functional gene to a patient suffering from a disease caused by a lack of that gene, or, recruitment of endogenous stem cells to the damaged heart tissue. By providing a gene that allows for recruitment, stimulation and proliferation of cardiac stem cells, the treatment of heart disease or disorders thereof can be accelerated even further. Therefore, the present invention also provides the ability to direct the localization of the transfused cells such as allogeneic stem cells that have a stable, normal gene. Such transfused cells then create a stable micro-chimera of the recipient.

Recruiting the stem cells to the target site can be induced artificially by administering a suitable chemokine systemically or at the desired site via injection or through expression from the mesenchymal stem cells. A suitable molecule is hypoxia inducible factor-1, a chemokine such as stromal derived factor-1 (SDF-1). Endothelial stem cells may also be recruited to the desired site by means of an interleukin, such as IL-1 or IL-8.

It may be desirable that the cells have the ability to replicate in certain drug screening and therapeutic applications, and to provide a reservoir for the generation of cardiomyocytes and their precursors. The cells can optionally be telomerized to increase their replication potential, either before or after they progress to restricted developmental lineage cells or terminally differentiated cells. Stem cells that are telomerized may be taken down the differentiation pathway described earlier; or differentiated cells can be telomerized directly.

Cells are telomerized by genetically altering them by transfection or transduction with a suitable vector, homologous recombination, or other appropriate technique, so that they express the telomerase catalytic component (TERT), typically under a heterologous promoter that increases telomerase expression beyond what occurs under the endogenous promoter. Particularly suitable is the catalytic component of human telomerase (hTERT), provided in International Patent Application WO 98/14592. For certain applications, species homologs like mouse TERT (WO99/27113) can also be used. Transfection and expression of telomerase in human cells is described in Bodnar et al., *Science* 279:349, 1998 and Jiang et al., *Nat. Genet.* 21:111, 1999. In another example, hTERT clones (WO 98/14592) are used as a source of hTERT encoding sequence, and spliced into an EcoRI site of a PBBS212 vector under control of the MPSV promoter, or into the EcoRI site of commercially available pBABE retrovirus vector, under control of the LTR promoter.

Differentiated or undifferentiated stem cells are genetically altered using vector containing supernatants over a 8-16 h period, and then exchanged into growth medium for 1-2 days. Genetically altered cells are selected using a drug selection agent such as puromycin, G418, or blasticidin, and then recultured. They can then be assessed for hTERT expression by RT-PCR, telomerase activity (TRAP assay), immunocytochemical staining for hTERT, or replicative capacity. The following assay kits are available commercially for research purposes: TRAPeze™, XL Telomerase Detection Kit (Cat. s7707; Intergen Co., Purchase N.Y.); and TeloTAGGG Telomerase PCR ELISAplus (Cat. 2,013,89; Roche Diagnostics, Indianapolis Ind.). TERT expression can also be evaluated at the mRNA by RT-PCR. Available commercially for research purposes is the LightCycler TeloTAGGG hTERT quantification kit (Cat. 3,012,344; Roche Diagnostics). Continuously replicating colonies are enriched by further culturing under conditions that support proliferation, and cells with desirable phenotypes can optionally be cloned by limiting dilution.

In certain embodiments, stem cells are differentiated into cardiomyocyte precursors, and then genetically altered to express TERT. In other embodiments, stem cells are genetically altered to express TERT, and then differentiated into cardiomyocyte precursors or terminally differentiated cells. Successful modification to increase TERT expression can be determined by TRAP assay, or by determining whether the replicative capacity of the cells has improved.

Depending on the intended use of the cells, other methods of immortalization may also be acceptable, such as transforming the cells with DNA encoding myc, the SV40 large T antigen, or MOT-2 (U.S. Pat. No. 5,869,243, International Patent Applications WO 97/32972 and WO 01/23555). Transfection with oncogenes or oncovirus products is less suitable when the cells are to be used for therapeutic purposes. Telomerized cells are of particular interest in applications of where it is advantageous to have cells that can proliferate and maintain their karyotype—for example, in pharmaceutical screening, and in therapeutic protocols where differentiated cells are administered to an individual in order to augment cardiac function.

The cells can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type. Of particular interest are cells that are genetically altered to express one or more growth factors of various types, cardiotropic factors such as atrial natriuretic factor, cripto, and cardiac transcription regulation factors, such as GATA-4, Nkx2.5, and MEF2-C. Production of these factors at the site of administration may facilitate adoption of the functional phenotype enhance the beneficial effect of the administered cell, or increase proliferation or activity of host cells neighboring the treatment site.

Introducing Transgenes Into Stem Cells

Means for introducing transgenes into cells are well known. A variety of methods for delivering and expressing a nucleic acid within a mammalian cell are known to those of ordinary skill in the art. Such methods include, for example viral vectors, liposome-based gene delivery (WO 93/24640; Mannino Gould-Fogerite, *BioTechniques* 6(7): 682-691 (1988); U.S. Pat. No. 5,279,833; WO 91/06309; Felgner et al., *Proc. Natl. Acad. Sci. USA* 84:7413-7414 (1987); and Budker et al., *Nature Biotechnology*, 14(6):760-764 (1996)). Other methods known to the skilled artisan include electroporation (U.S. Pat. Nos. 5,545,130, 4,970,154, 5,098,843, and 5,128,257), direct gene transfer, cell fusion, precipitation methods, particle bombardment, and receptor-mediated uptake (U.S. Pat. Nos. 5,547,932, 5,525,503, 5,547,932, and 5,460,831). See also, U.S. Pat. No. 5,399,346.

Widely used retroviral vectors include those based upon murine leukemia virus (MuLV), gibbon ape leukemia virus (GaLV), Simian Immuno deficiency virus (SIV), human immuno deficiency virus (HIV), and combinations thereof. See, e.g., Buchscher et al., *J. Virol.* 66(5):2731-2739 (1992); Johann et al., *J. Virol.* 66(5):1635-1640 (1992); Sommerfelt et al., Virol. 176:58-59 (1990); Wilson et al., *J. Virol.* 63:2374-2378 (1989); Miller et al., *J. Virol.* 65:2220-2224 (1991); PCT/US94/05700, and Rosenburg & Fauci, in Fundamental Immunology, Third Edition (Paul ed., 1993)).

AAV-based vectors are also used to transduce cells with target nucleic acids, e.g., in the in vitro production of nucleic acids and polypeptides, and in vivo and ex vivo gene therapy procedures. See, West et al., Virology 160:38-47 (1987); U.S. Pat. No. 4,797,368; WO 93/24641; Kotin, *Human Gene Therapy* 5:793-801 (1994); Muzyczka, *J. Clin. Invst.* 94:1351 (1994) and Samulski (supra) for an overview of AAV vectors. Construction of recombinant AAV vectors are described in a number of publications, including Lebkowski, U.S. Pat. No. 5,173,414; Tratschin et al., *Mol. Cell. Biol.* 5(11):3251-3260 (1985); Tratschin et al., *Mol. Cell. Biol.* 4:2072-2081 (1984); Hermonat & Muzyczka, *Proc. Natl. Acad. Sci. USA* 81:6466-6470 (1984); and Samulski et al., *J. Virol.* 63:03822-3828 (1989).

Retroviral vectors are typically used for cells useful in the present invention. Such vectors may comprise, for example, an HIV-2 packageable nucleic acid packaged in an HIV-2 particle, typically using a packaging cell line. Cell transduction vectors have considerable commercial utility as a method of introducing genes into target cells. In particular, gene therapy procedures, in which the cell transduction vectors of the invention are used to transduce target cells with a therapeutic nucleic acid in an in vivo or ex vivo procedure may be used.

Stem cells such as $CD34^+$ stem cells may be used in ex vivo procedures for cell transduction and gene therapy. The present invention utilizes the feature that stem cells differentiate into other cell types in vitro, or can be introduced into a mammal (such as the donor of the cells) where they will engraft in the heart for differentiation. Hence, embodiments extend to directing stem cells to particular organs to regenerate tissue, such as to the heart to regenerate cardiac muscle cells. Stem cells, such as, for example, pluripotent stem cells, can also be used in conjunction with the mesenchymal stem cells. If it is desired, the stem cells can also be differentiated in vitro. Methods for differentiating $CD34^+$ cells in vitro into clinically important immune cell types using cytokines such a GM-CSF, IFNγ and TNFα are known (See, Inaba et al., *J. Exp. Med.* 176, 1693-1702 (1992)). Yu et al., *PNAS* 92: 699-703 (1995) describe a method of transducing CD34⁺ cells from human fetal cord blood using retroviral vectors.

Drug Screening

Cells of this invention can be used to screen for factors (such as solvents, small molecule drugs, peptides, oligonucleotides) or environmental conditions (such as culture conditions or manipulation) that affect the characteristics of such cells and their various progeny.

In some applications, mesenchymal stem cells or other stem cell types are used to screen factors that promote maturation into later-stage cardiomyocyte precursors, or terminally differentiated cells, or to promote proliferation and maintenance of such cells in long-term culture. For example, candidate maturation factors or growth factors are tested by adding them to cells in different wells, and then determining any phenotypic change that results, according to desirable criteria for further culture and use of the cells.

Other screening applications of this invention relate to the testing of pharmaceutical compounds for their effect on cardiac muscle tissue maintenance or repair. Screening may be done either because the compound is designed to have a pharmacological effect on the cells, or because a compound designed to have effects elsewhere may have unintended side effects on cells of this tissue type. The screening can be conducted using any of the stem cells or terminally differentiated cells.

The reader is referred generally to the standard textbook In vitro Methods in Pharmaceutical Research, Academic Press, 1997, and U.S. Pat. No. 5,030,015. Assessment of the activity of candidate pharmaceutical compounds generally involves combining the cells of this invention with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375-410 in In vitro Methods in Pharmaceutical Research, Academic Press, 1997) for further elaboration.

Effect of cell function can be assessed using any standard assay to observe phenotype or activity of cardiomyocytes, such as marker expression, receptor binding, contractile activity, or electrophysiology—either in cell culture or in vivo. Pharmaceutical candidates can also be tested for their effect on contractile activity—such as whether they increase or decrease the extent or frequency of contraction. Where an effect is observed, the concentration of the compound can be titrated to determine the median effective dose ($ED_{50}$).

Treatment

The amount of stem cells administered to the patient will also vary depending on the condition of the patient and should be determined via consideration of all appropriate factors by the practitioner. Preferably, however, about $1 \times 10^6$ to about $1 \times 10^{12}$, more preferably about $1 \times 10^8$ to about $1 \times 10^{11}$, more preferably, about $1 \times 10^9$ to about $1 \times 10^{10}$ stem cells are utilized for adult humans. These amounts will vary depending on the age, weight, size, condition, sex of the patient, the type of tumor to be treated, the route of administration, whether the treatment is regional or systemic, and other factors. Those skilled in the art should be readily able to derive appropriate dosages and schedules of administration to suit the specific circumstance and needs of the patient.

Methods of re-introducing cellular components are known in the art and include procedures such as those exemplified in U.S. Pat. No. 4,844,893 to Honsik, et al. and U.S. Pat. No. 4,690,915 to Rosenberg.

Pharmaceutical Compositions

In other embodiments, the present invention provides pharmaceutical compositions comprising mesenchymal stem cells. In other preferred embodiments, pharmaceutical compositions comprise a mesenchymal stem cell and embryonic stem cells.

In other aspects, the present invention features kits for treating cardiac tissue damage or for delivering a functional gene or gene product to the heart in a mammal comprising a mesenchymal stem cell. Stem cells generally have been presented to the desired organs either by injection into the tissue, by infusion into the local circulation, or by mobilization of autologous stem cells from the marrow accompanied by prior removal of stem cell-entrapping organs before mobilization when feasible, i.e., splenectomy.

In some embodiments, the administration of the stem cell compositions can be coupled with other therapies. For example, a therapeutic agent can be administered prior to, concomitantly with, or after infusing the stem cells to a patient.

Administration of cells transduced ex vivo can be by any of the routes normally used for introducing a cell or molecule into ultimate contact with blood or tissue cells. The stem cells may be administered in any suitable manner, preferably with pharmaceutically acceptable carriers. Suitable methods of administering such cells in the context of the present invention to a patient are available, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Parenteral administration is one useful method of administration. The formulations can be presented in unit-dose or multi-dose sealed containers, such as ampoules and vials, and in some embodiments, can be stored in a freeze-dried (lyophilized) condition requiring only the addition of the sterile liquid carrier, for example, water, for injections, immediately prior to use. These formulations may be administered with factors that mobilize the desired class of adult stem cells into the circulation.

Extemporaneous injection solutions and suspensions can be prepared from sterile powders, granules, and tablets of the kind previously described. Cells transduced by the vector as described above in the context of ex vivo therapy can also be administered parenterally as described above, except that lyophilization is not generally appropriate, since cells are destroyed by lyophilization. The dose administered to a patient, in the context of the present invention should be sufficient to effect a beneficial therapeutic response in the patient over time. The dose will be determined by the efficacy of the particular cells employed and the condition of the patient, as well as the body weight of the patient to be treated. The size of the dose also will be determined by the existence, nature, and extent of any adverse side effects that accompany the administration of a cell type in a particular patient. In determining the effective amount of cells to be administered in the treatment or prophylaxis of diseases, the physician should evaluate circulating plasma levels, and, in the case of replacement therapy, the production of the gene product of interest.

Transduced cells are prepared for reinfusion according to established methods. See, Abrahamsen et al., *J. Clin. Apheresis* 6:48-53 (1991); Carter et *Clin. Apheresis* 4:113-117 (1988); Aebersold et al., *J. Immunol. Methods* 112: 1-7 (1988); Muul et al., *J. Immunol. Methods* 101:171-181 (1987) and Carter et al., *Transfusion* 27:362-365 (1987). After a period of about 2-4 weeks in culture, the cells may number between $1\times10^6$ and $1\times10^{10}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

For administration, cells of the present invention can be administered at a rate determined by the $LD_{50}$ of the cell type, and the side effects of the cell type at various concentrations, as applied to the mass and overall health of the patient. Administration can be accomplished via single or divided doses. Adult stem cells may also be mobilized using exogenously administered factors that stimulate their production and egress from tissues or spaces, that may include, but are not restricted to, bone marrow or adipose tissues.

The invention has been described in detail with reference to preferred embodiments thereof. However, it will be appreciated that those skilled in the art, upon consideration of this disclosure, may make modifications and improvements within the spirit and scope of the invention. The following non-limiting examples are illustrative of the invention.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

EXAMPLES

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

Materials and Methods
Mesenchymal Stem Cell Isolation, Harvest and Labeling

Swine MSCs were isolated and expanded from a single, healthy male Yorkshire donor (Schuleri, K. H. et al. *Am. J. Physiol Heart Circ. Physiol* 294, H2002-H2011 (2008)). Briefly, bone marrow was obtained from the iliac crest, and aspirates were passed through a density gradient to eliminate undesired cell types and were plated with 25 ml MEM Alpha media (Mediatech, Manassas, Va.) containing 20% fetal Bovine Serum (Hyclone, Logan, Utah) in 162 $cm^2$ culture flasks (Fisher Scientific, Pittsburgh, Pa.). At 5-7 days after plating, non-adherent cells were washed away during medium changes and the remaining, plastic adherent, purified MSC population was expanded in culture. The MSC population was then harvested and transduced with 5-Bromodeoxyuridin (BrdU) or green fluorescent protein (Lenti-GFP vector, Lentigen) according to manufacturers' instructions. All used cells were harvested when they reached 80-90% confluence at passage 5. Labeled MSCs were placed in a cryopreservation solution consisting of 10% DMSO, 5% porcine serum albumin, and 85% Plasmalyte. Cells were placed in cryo bags at a concentration of 5-10 million MSCs per ml and frozen in a control-rate freezer to $-180°$ C. until the day of implantation. By using trypan blue staining, the viability of all thawed MSC lots was verified to be >85% before use in the study.

Induction of Myocardial Infarction and Transendocardial Injections

Seventeen healthy female Yorkshire swine weighed 25-35 kg, and 21 healthy Gottingen miniature swine weighing 20-27 kg were included in this study. Experimental myocardial infarction was generated (Schuleri, K. H. et al. *Am. J. Physiol Heart Circ. Physiol* 294, H2002-H2011 (2008); Amado, L. C. et al. *J. Am. Coll. Cardiol.* 48, 2116-2124 (2006)). Briefly, the right common carotid artery was canulated under anesthesia induced with ketamine (33 mg/kg, IM) and maintained with isoflurane (1.5-2.0%). Myocardial infarction was induced by accessing the Left Anterior Descending (LAD) coronary artery and occluding it after the first diagonal branch by inflating a coronary angioplasty balloon (2.75×15 mm). Because of differences in the coronary anatomy between Gottingen and Yorkshires, the balloon was inflated for 150 min and 60 min respectively in order to achieve comparable infarct sizes. Subsequently, the balloon was deflated, reperfusion was established and the carotid artery was permanently closed. All animals were adequately heparinized during the procedure. The Yorkshire group of animals received intramyocardial injections of allogeneic GFP labeled porcine MSCs (75×$10^6$ cells) or Placebo (Plasmalyte alone, Baxter Edwards Critical Care, Deerfield, Ill.), three days after myocardial infarction (MI). For the chronic heart failure model, infarcted minipigs were monitored for 12 weeks before transplantation (total of 200×$10^6$ allogeneic BrdU-labeled MSCs or plasmalyte). All injections were performed under fluoroscopy, with a pistol-needle tip injection catheter advanced to the LV through a steerable guide catheter (Stiletto, Boston Scientific, Natick, Mass.). Hypokinetic, akinetic, and dyskinetic areas were identified during contrast ventriculography, and injections were performed within and at the borders of the dysfunctional area, as defined by bi-plane ventriculography. A total of 15 injections were performed in each animal, with each injection containing 0.5 ml of the injectate. Each injection was fluoroscopically guided to distribute cells evenly throughout the entire infarct and border zones.

Cardiac MRI

Cardiac MR imaging (CMR) of the Gottingen's heart function were performed at the following time points: baseline, 10 days, 1, 2 and 3 months post-MI and 1, 2 and 3 months following transplantation. Serial CMR images were acquired with a four channel phase array, 1.5 T MR Scanner (Siemens Symphony, Erlangen, Germany) in anesthetized animals with electrocardiography gating and short breathhold acquisition. The protocol for cine-CMR images and tagging-CMR images has been described before (Amado, L. C. et al. *J. Am. Coll. Cardiol.* 48, 2116-2124 (2006); Amado, L. C. et al. *Proc. Natl. Acad. Sci. U.S.A.* 102, 11474-11479 (2005)). Briefly, LV Global function was assessed in steady state free precession with a number of slices to cover the entire LV from apex to base. Imaging parameters were as follow: Echo delay time (TE)=1.9 ms, repetition time (TR)= 4.2 ms; flip angle 45°; 256×160 matrix; 8 mm slice thickness/no gap; 28 cm field of view (FOV) and 1 number of signal average (NSA). Cine images were analyzed with research comprehensive software validated by the Cardiology MR group at Lund University, Sweden.

To assess regional cardiac function, tagging MRI images were acquired with an ECG-gated, segmented k-space, fast gradient recall echo-pulsed sequence with a spatial modulation to generate a grid pattern. Images were obtained at the same level of cine-MR images with the following parameters: TR: 6.7, TE: 3, flip angle=12°; 256×160 matrix; views/second 4; 8 mm slice thickness no gap; 31.25 kHz; 28 cm FOV; 1 NSA; and 6 pixels tagging space. Images were quantitatively analyzed with a custom software package (DIAGNOSOFT™ PLUS, Diagnosoft Inc, Palo Alto, Calif.). Regional strain magnitude was determined from the 24 radially displaced segments for each short axis section covering the entire LV and averaged among slices for each region and each time point, generating a strain map for each time point over the cardiac cycle. The peak systolic circumferential strain (peak Ecc) was determined from the strain map for each time point. Delayed Contrast enhancement was used to assess the extension of the infarcted area. The protocol included an intravenous bolus of Gadolinium-DTPA (0.1 mmol/kg, 5 m/s, MAGNEVISTT™, Berlex, Bayer Healthcare Pharmaceuticals) through a peripheral intravenous line. Images were acquired 15 minutes later at the same location as the short axis cine-images. Imaging parameters were TR=7.3, TE=3.3, TI=200 ms; flip angle=25°, 256×196 matrix; 8 mm slice thickness gap 31.2 kHz, 28 cm FOV and 2 NSA.

Histology

For the first phase of the study, microscopic evaluation between the treated (n=3), placebo (n=3) and control (n=3) Yorkshire pigs was performed at 2 weeks after the intramyocardial injections. Moreover, in order to assess the acute immunophenotypic evolution of the transplanted MSCs, 8 more animals were sacrificed at 24 h (n=1 placebo and n=1 MSCs treated) and 72 h (n=3 placebo and n=3 MSCs treated) postinjection. For the second phase of the study, microscopic evaluation between the treated (n=12) and placebo (n=9) Gottingen pigs was performed 3 months after the intramyocardial injections. All animals completing the study were humanely euthanized and their hearts were excised, sectioned into 4-mm-thick short-axis slices, weighted and digitally photographed. Multiple tissue samples were collected from the infarcted, border and remote zones of each slice, fixed in 10% buffered formalin and embedded in paraffin. Hematoxylin and Eosin (H&E), as well as Masson's Trichrome staining were used for the primary histological examination.

Immunofluorescence Confocal Microscopy

Immunofluorescence studies were carried out on 4 μm-thick paraffin sections. Briefly, after deparaffinizing and rehydrating the tissue sections, antigen unmasking was performed by microwaving the slides for 20 min in citrate buffer Solution, pH=6 (Dako, Carpenteria, Calif.). The sections were blocked for 1 h at RT with 10% normal donkey serum (Chemicon International Inc, Temecula, Calif.), followed by 1 h incubation at 37° C. with the primary antibody. The following antibodies were used: C-kit, α-sarcomeric actinin, α-smooth muscle actin, Connexin-43 (Sigma, Saint Louis, Mo.), N-cadherin, anti-GFP, Laminin, Phospho-Histone H3 (Abcam, Cambridge, Mass.), GATA-4, MDR1, Integrin-β1, CD3, CD14, CD68 (Santa Cruz Biotechnologies, Santa Cruz, Calif.), activated Caspase-3 (BD Biosciences, San Jose, Calif.), Nkx2.5 (R&D systems Inc, Minneapolis, Minn.), Factor VIII (Biocare Medical, Concord, Calif.) and KDR (Cell Signaling, Boston, Mass.). Consequently, the antibodies were visualized by incubating the sections for 1 h at 37° C. with FITC, Cy3 and Cy5-conjugated F(ab)$_2$ fragments of affinity-purified secondary antibodies (Jackson Immunoresearch, West Grove, Pa.). Slides were counterstained with DAPI, mounted with Pro-Long Antifade Gold reagent (Invitrogen, Carlsbad, Calif.) and stored at 4° C. until further examination. Microscopic evaluations and image acquisitions were performed with a Zeiss LSM-510 Confocal Microscope (Carl Zeiss MicroImaging, Inc. Thornwood, N.Y.).

Tissue Mapping

For assessing the trafficking of the MSCs, the Compucyte Laser Scanning Cytometer (LSC) was used according to manufacturers' instructions (CompuCyte Corporation, Cambridge, Mass.). Briefly, after detecting and amplifying the signal of the GFP$^{pos}$ transplanted MSCs with a FITC-labeled anti-GFP antibody according to immunofluorescent protocols established in this laboratory, the tissue slides were scanned under the LSC to map the spatial distribution of the FITC signal on the samples. The detected fluorescent signal was projected as a scatter plot and accordingly, was adjusted and merged to the H&E scanned slide (Coolscan, Nikon) of the same sample by using an imaging software package (Adobe Photoshop CS3). The detected scatters were further cross-checked under the confocal microscope to exclude the detection of any false positive signal.

Fluorescence In Situ Hybridization

Fluorescence in Situ Hybridization (FISH) was employed to detect the Y chromosome of the sex-mismatched transplanted allogeneic MSCs in the female porcine hearts. The metaphase chromosomes were detected by hybridizing the tissue samples with Cy3-conjugated porcine Y chromosome paints (StarFISH, Cambio Ltd, Cambridge, UK) according to manufacturers' instructions. Briefly, following deparaffinization and rehydration, the samples were microwaved for 20 min in citrate Buffer, pH=6 (Dako). After cooling for 30 min at room temperature (RT), tissues were digested for 3 min at 37° C. with pepsin, washed with 2×SSC buffer (Invitrogen) and dehydrated through serial ethanol washing steps. The samples were air-dried and the probe was applied. After covering the samples with a cover slip and sealing them with rubber cement, the samples were placed in the hybridizer (Dako) for denaturation (10 min at 80° C.) followed by overnight hybridization at 37° C. The next day, samples were washed with 2×SSC, mounted with DAPI and covered.

Morphometric Analyses and Microscopic Evaluation

The numbers of GFPP$^{pos}$, c-kit$^{pos}$ and Y$^{pos}$ cells were quantitated per square millimeter (mm$^2$). Apoptotic and mitotic cells at 24 h and 72 h time points were expressed as the percentage of the GFP$^{pos}$ cells co-localized with activated caspase 3 and phospho-H3 respectively. The same approach was followed for the quantification of the cardiac and vascular commitment of the allografts as well as the endogenous c-kit$^{pos}$ cells. Morphometric analysis was performed by using a custom research package (Image J, NIH, Bethesda, Md.). For assessing the density of newly formed vessels, the axial ratio (major diameter/minor diameter) for each Y chromosome containing vascular structure was obtained. This methodology was used to correct the angle of orientation of the vessels with the plane of section (Tillmanns, J. et al. *Proc. Natl. Acad. Sci. USA* 105, 1668-1673 (2008)). The sum of the axial ratios of vessels per unit area of tissue yielded the vessel density per sample.

Statistical Analysis

All the values are presented as means±SEM. All analyses were performed by using the SPSS for Windows version 15.0 (SPSS Inc., Chicago, Ill.). Differences between groups following immunohistological evaluation were compared by using One Way ANOVA. Differences between groups in ejection fraction and infarct size based on MR images were calculated by using one-way ANOVA within different time points. The Tukey's test was used for the post-hoc analysis. Difference in peak Ecc were calculated by repeated measurements 2 way analysis of variance with one factor repetition. Pearson correlation was applied to find a relation between cell engraftment and increase in peak Ecc. A level of $P \leq 0.05$ was considered statistically significant.

Animal Studies

For this study, 17 healthy female Yorkshire swine weighing 25-35 kg, and 21 healthy Gottingen miniature swine weighing 20-27 kg, underwent experimental myocardial infarction (MI) followed by reperfusion. The study was conducted in 2 phases. In the first phase, three groups were studied: Yorkshire pigs received transendocardial injections (TEI) (Stiletto, Boston Scientific, Natick, Mass.) of $75 \times 10^6$ GFP labeled allogeneic adult bone marrow derived mesenchymal stem cells (αMSCs) (n=7), Placebo (n=7) or no injection (n=3) three days following the MI. Animals were sacrificed at 24 h (n=1 placebo and n=1-αMSCs treated), 72 h (n=3 placebo and n=3 αMSCs treated) and 2 weeks (n=3 αMSCs treated n=3 placebo and n=3 control) after transplantation in order to study the fate of the allogeneic cells.

In the second phase, two groups were studied: Gottingen minipigs received TEI of $200 \times 10^6$ cells of male αMSCs (n=12) or placebo (n=9), 12 weeks after MI. Animals were followed up by cine and Tagging-MRI analyses (Siemens Symphony, Erlangen, Germany) at multiple time points (baseline, 10 days, 1, 2 and 3 months post-MI and 1, 2 and 3 months following transplantation) in order to assess the amount of functional recovery of the treated vs. the untreated groups.

Example 1: Mesenchymal Stem Cells Regenerate Cardiac Muscle, Vasculature and Stem Cell Niches In order to determine whether mesenchymal stem cells have cardiac precursor potential or whether their therapeutic effect is exerted through paracrine effects, GFP labeled male allogeneic adult bone marrow derived mesenchymal stem cells (αMSCs) were injected into female pigs following myocardial infarction (MI) (FIG. 5). Without wishing to be bound by theory, it was hypothesized that allogeneic adult bone marrow derived mesenchymal stem cells (αMSCs) are true adult precursor cells which can differentiate into the three cardiac cell lineages, and that αMSCs participate in cardiac recovery by forming cell-cell interactions with existing myocardial elements including with endogenous precursor cells.

Figure 8A:
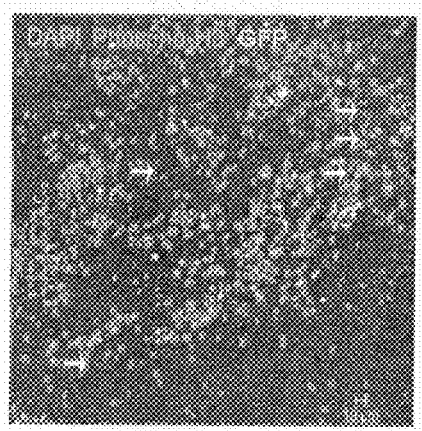
FIGS. 8A to 8C show the fate of the allografts in the host myocardium during the first 72 h after transplantation.
Figure 8B:
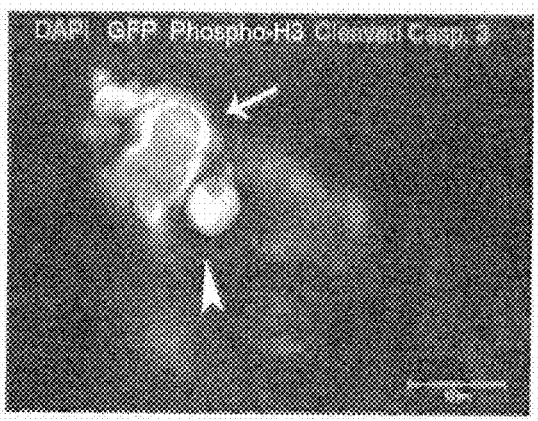
Figure 8C:
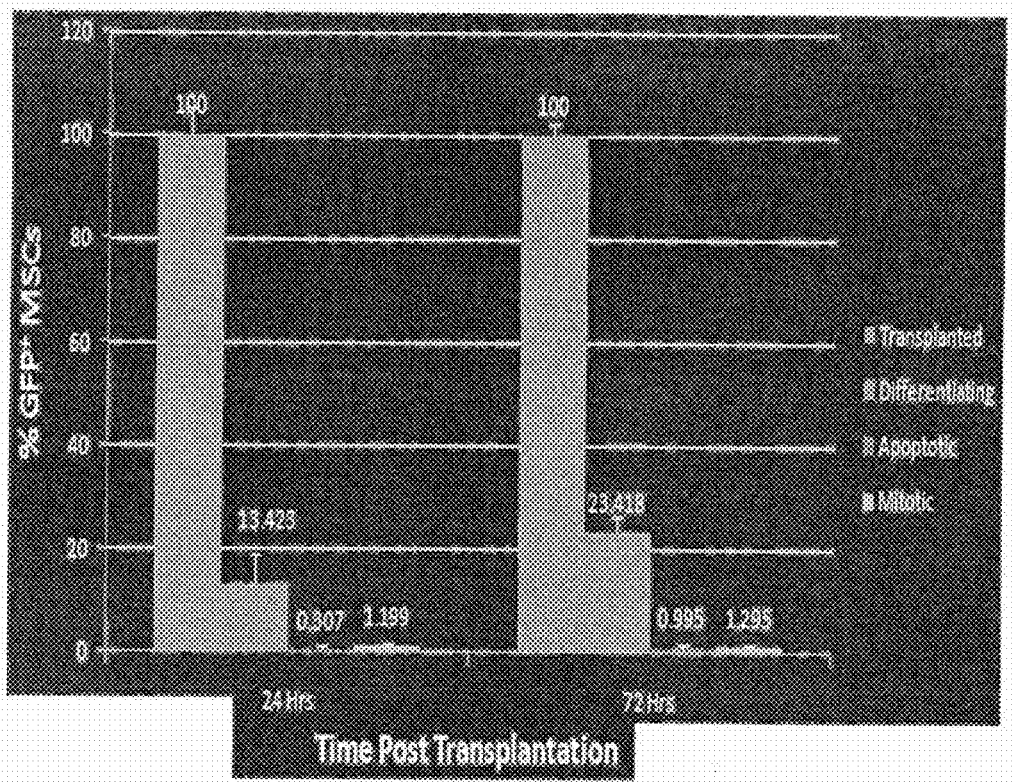
Figure 9A:
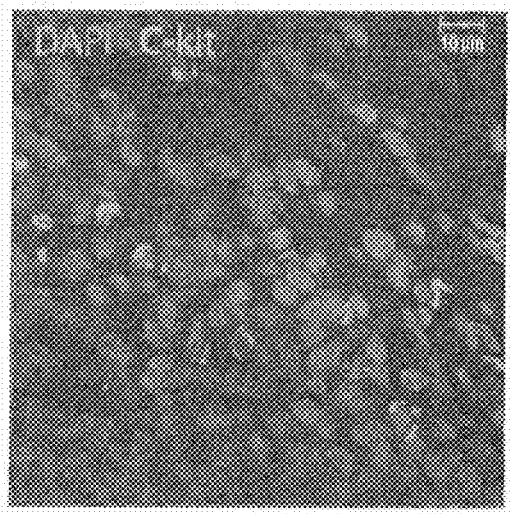
FIGS. 9A to 9D show the mobilization of endogenous c-kit$^{pos}$ CSCs 2 weeks after transplantation of MSCs.
Figure 9B:
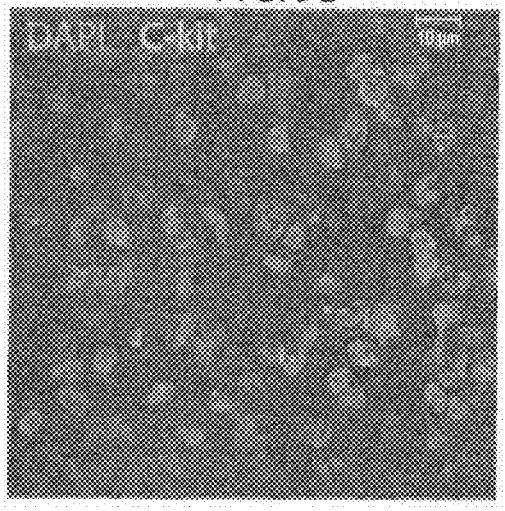
Figure 9C:
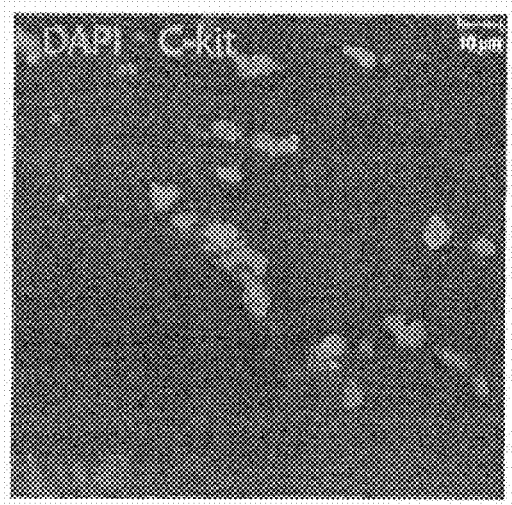
Figure 9D:
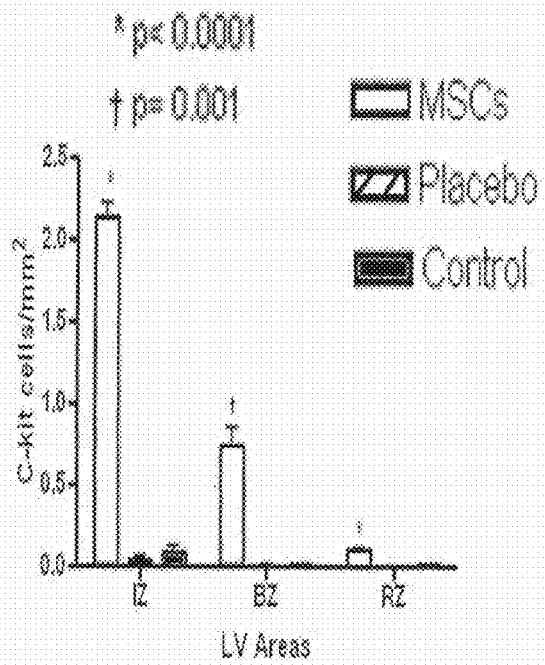

First the fate of allogeneic GFP, Y-chromosome positive αMSCs injected directly into the myocardium via an endocardial catheter in pigs 3-days following myocardial infarction (MI), was examined. After cell delivery to the infarct and border zones, cell retention was robust and was entirely confined to the infarct and border zones of the myocardium, with evidence of migration of cells throughout this region (FIGS. 6A-6E and FIGS. 7A-7D), including endo- to epicardial migration, and in cellular streams throughout the area of damage. From 1 to 3 days after injection, αMSCs displayed evidence of self-renewal with minimal apoptosis (FIGS. 8A, 8C). Immunostaining for phosphorylated histone-H3 1 and 3 days after transplantation demonstrated that a substantial number of cells entered the cell cycle and underwent mitosis, whereas concurrent absence of the pro-apoptotic marker activated caspase-3 in the majority of αMSCs indicated their capacity for survival (FIGS. 8B, 8C).

Figure 1A:
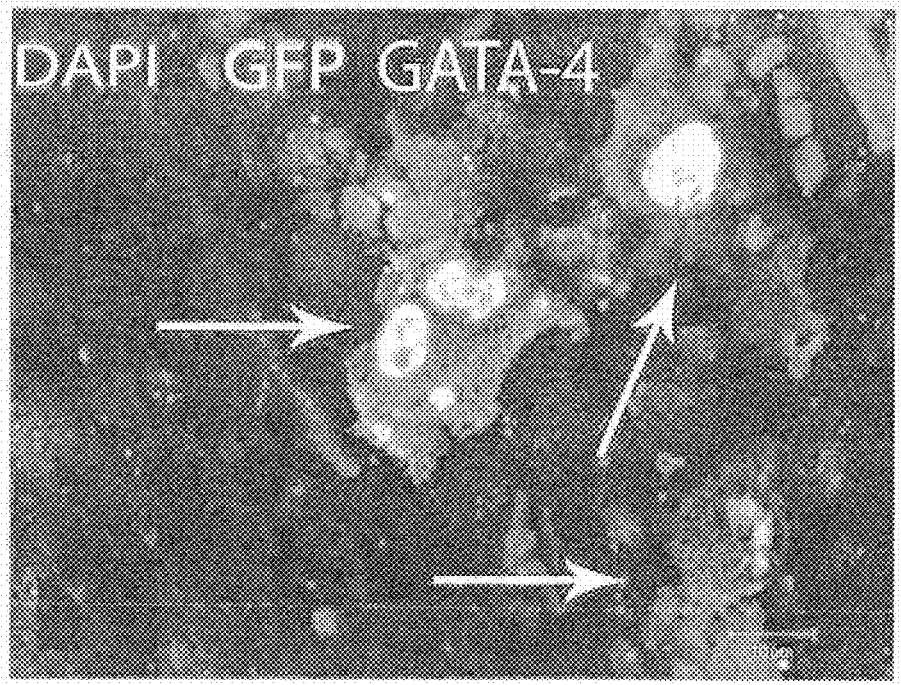
FIGS. 1A-1I are scans of photographs showing the trilineage differentiation of allogeneic MSCs.
Figure 1B:
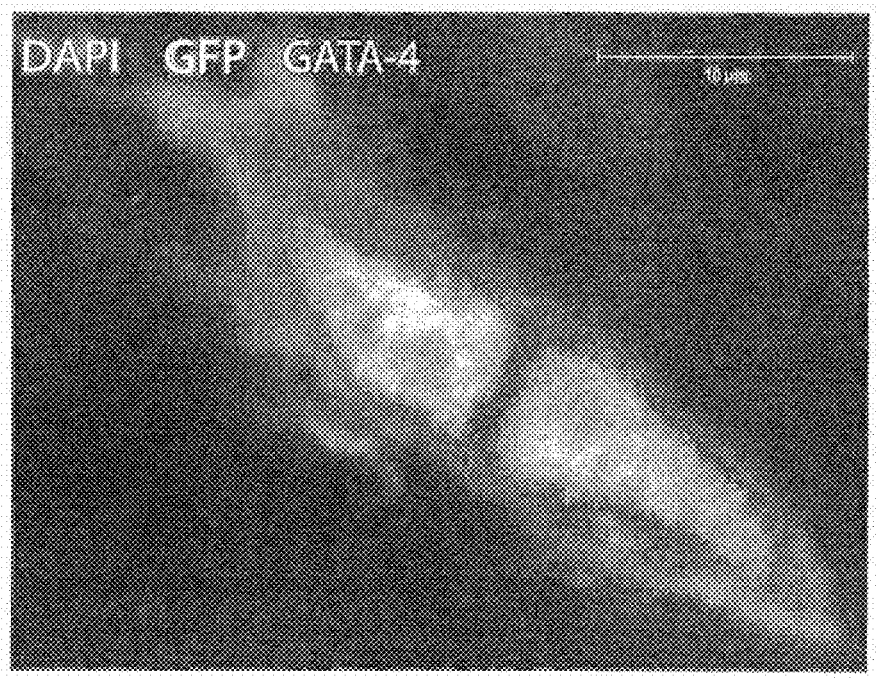
Figure 1C:
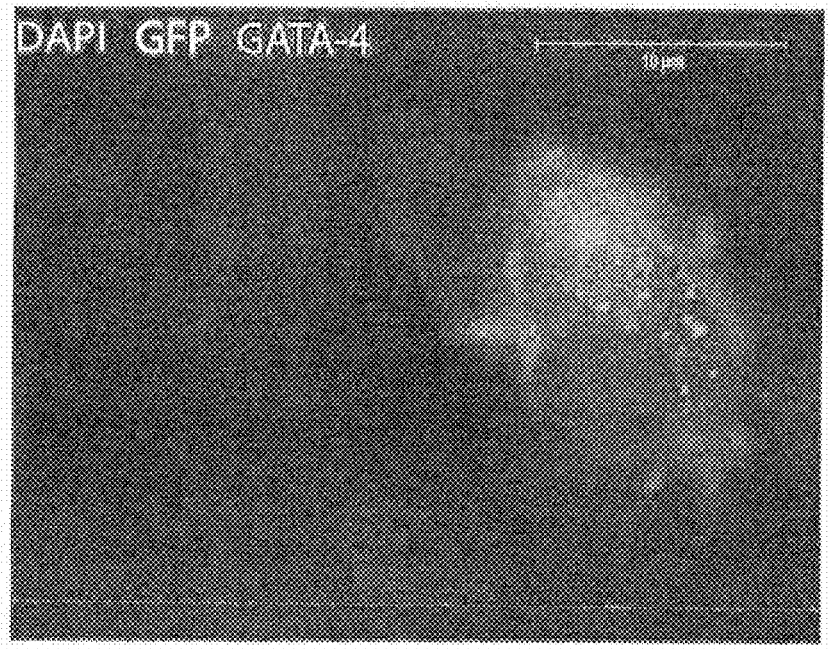
Figure 1D:
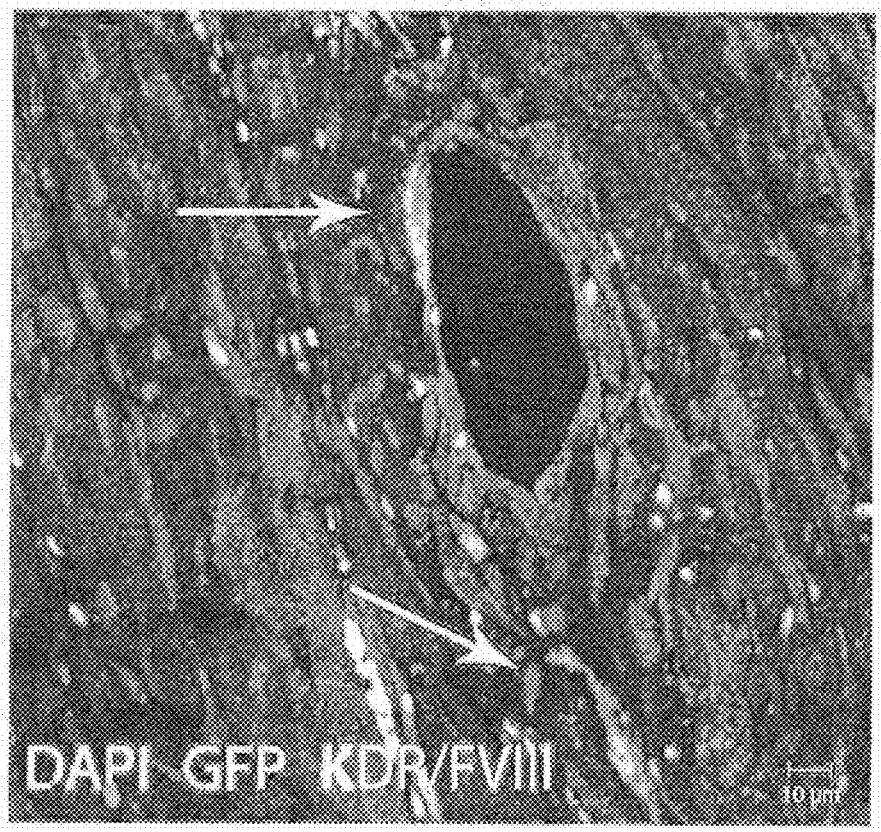
Figure 1E:
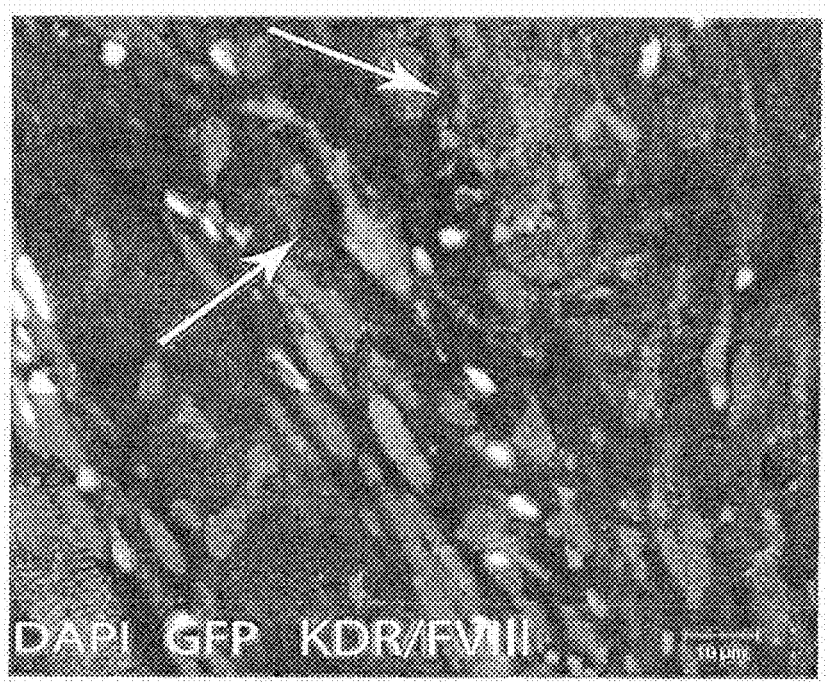
Figure 1F:
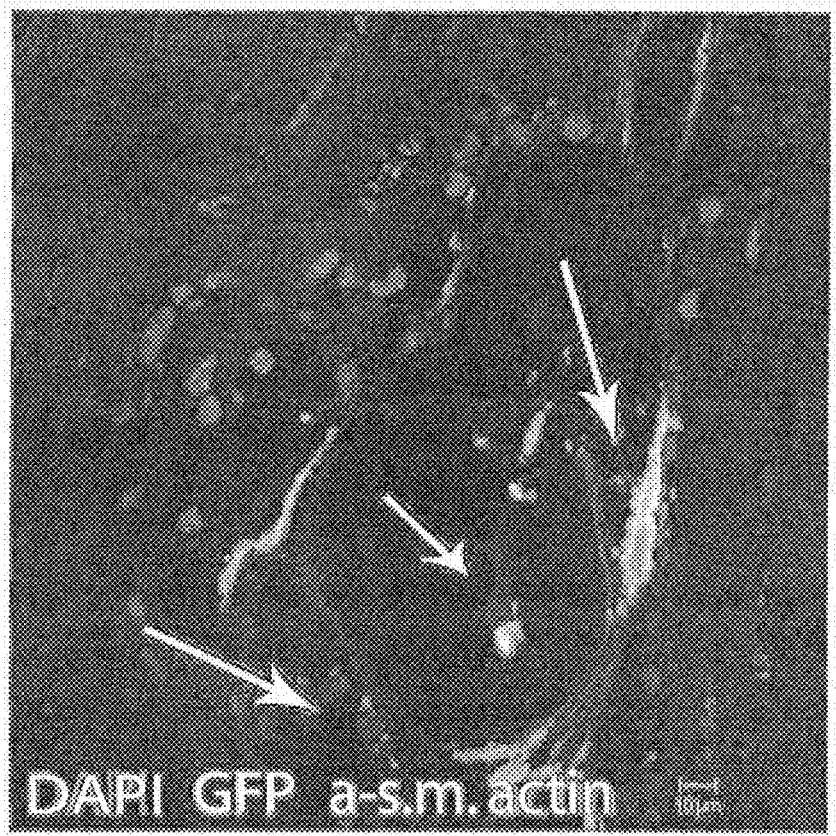
Figure 1G:
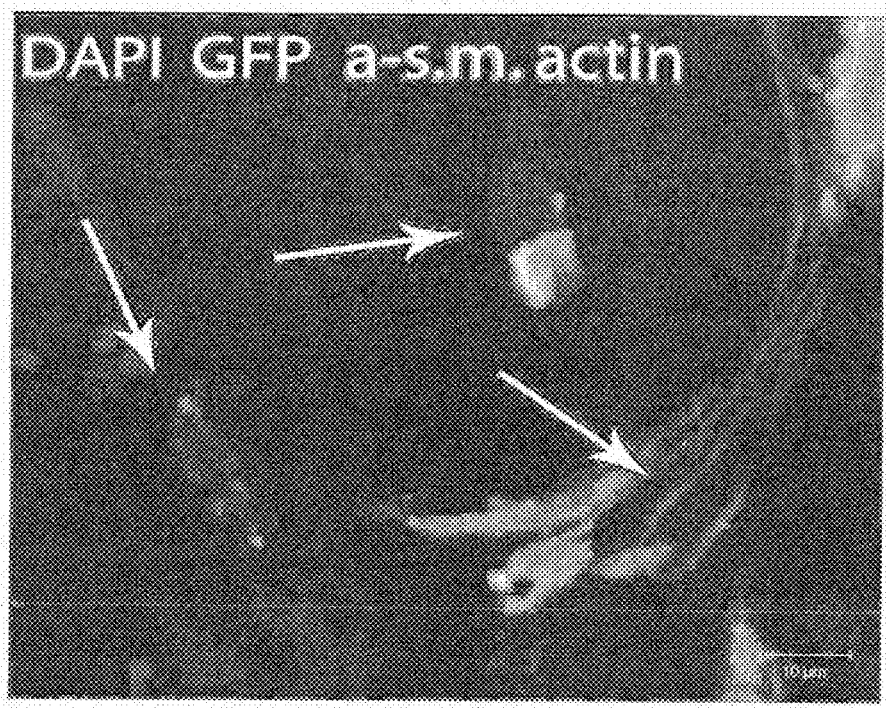
Figure 1H:
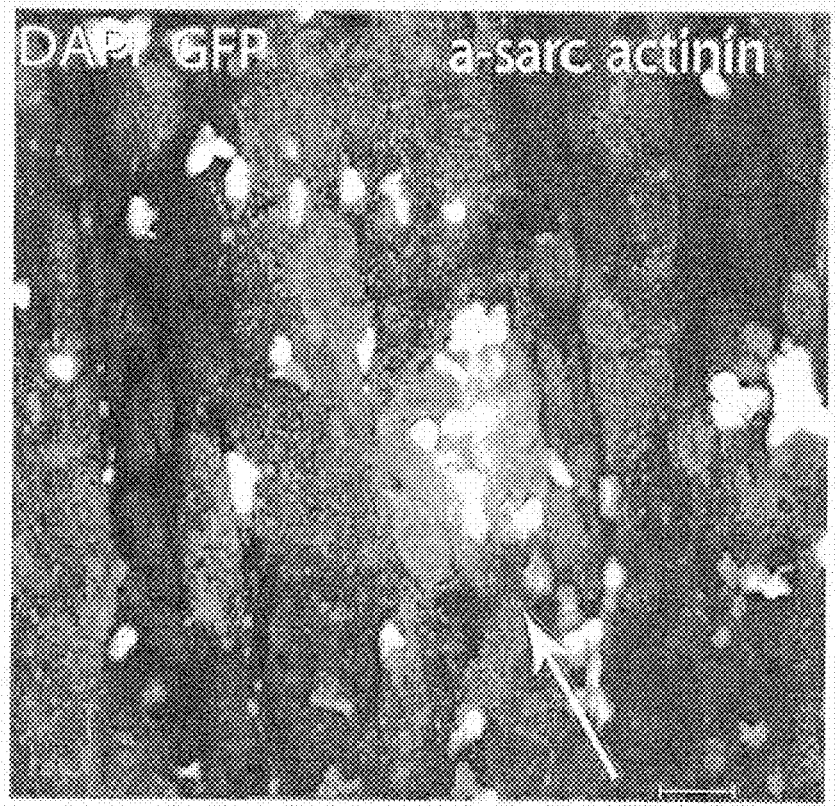
Figure 1I:
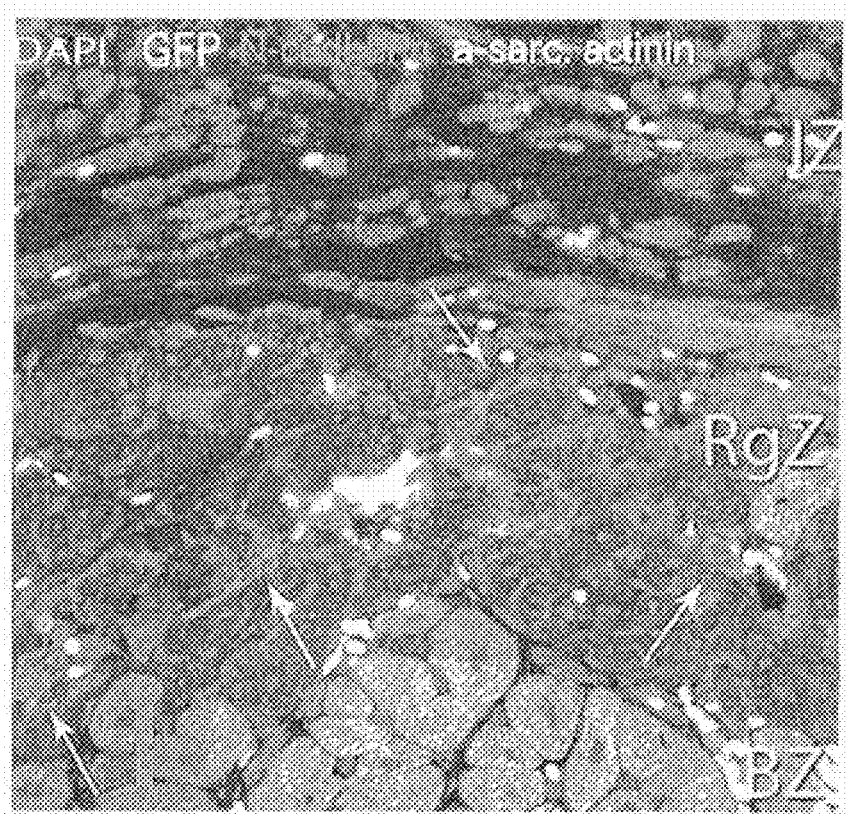

To address lineage commitment of αMSCs we assessed co-localization of GFPpos αMSCs with the cardiac transcription factor GATA-4, endothelial markers Factor VIII and KDR, the vascular smooth muscle marker α-smooth muscle actin, and the cardiomyocyte marker α-sarcomeric actinin. MSCs differentiation into cardiac precursor cells was evident 24 h after transplantation and increased 2-fold by 72 hours, an increase driven by both differentiation as well as cell replication (FIGS. 1A, 1B, FIG. 8C). In addition, endothelial and vascular smooth muscle cell lineage commitment was not present 24 h after transplantation, but could both be detected by 72 hours (FIGS. 1C-1F). There were GFP$^{pos}$ αMSCs (1.3±0.4%) that co-localized with KDR/Factor VIII, documenting lineage commitment to endothelial cells. There was extensive cell-cell interaction between GFP$^{pos}$ αMSCs and native cardiac cells, mediated by Connexin-43 and N-cadherin FIGS. 1G, 1H).

Two weeks after injection, there remained robust cell retention and further differentiation into mature cell phenotypes (FIG. 2, FIGS. 7A-7D]. GFP$^{pos}$ αMSCs expressed α-sarcomeric actinin and GATA-4 and exhibited morphological characteristics both of immature cardiac precursor cells FIGS. 2A, 2B) and of mature cardiac myocytes and vascular cells (FIGS. 2C, 2D). Chimeric myocardium was present within infarct and border zones but not in the remote areas, and formed cell-cell interactions with native cardiac myocytes (FIGS. 2E, 2F).

Figure 2A:
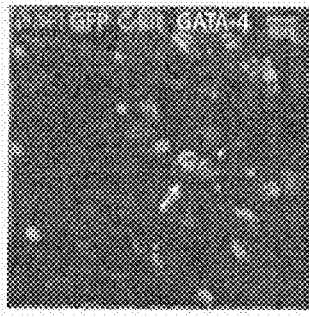
Figure 2B:
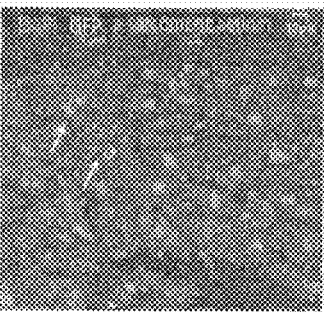
Figure 2C:
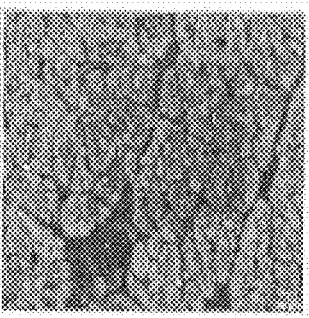
Figure 2D:
Figures 2E, 2F:
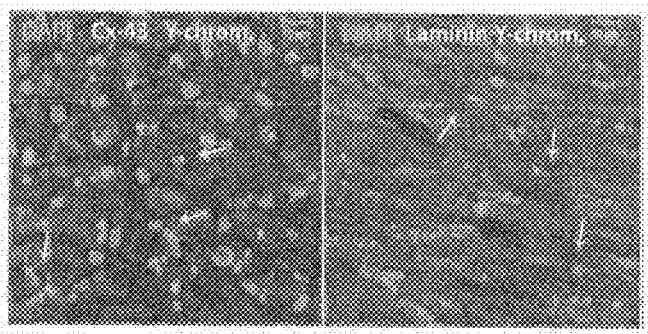
Figure 2G:
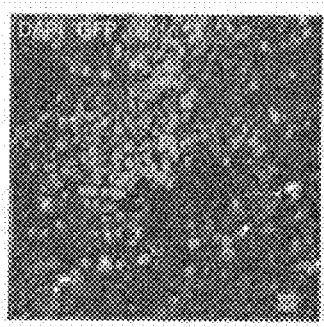
Figure 2H:
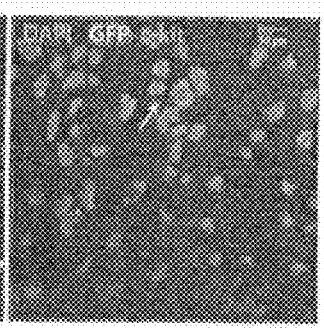

Next, it was tested whether αMSCs interact with endogenous c-kit$^{pos}$ cardiac stem cells (CSCs). Endogenous c-kit$^{pos}$ CSCs were rare 1-3 days after transplantation, but dramatically increased in the αMSCs treated pigs by 2 weeks (FIGS. 2G, 2H). The number of c-kit cells increased by 50-fold in the infarct zone of the treated animals and was also elevated, though less dramatically, in border and remote zones of MSC treated animals (FIGS. 9A-9D). These c-kit$^{pos}$ cells were CD3$^{neg}$, CD14$^{neg}$ and CD68$^{neg}$, excluding inflammatory and mast cells phenotypes, and were detected in clusters in the infarcted and border zones of the αMSCs treated animals. In remote areas and in non-treated hearts, c-kit cells were observed as a rare isolated cell and were not part of cell clusters (FIGS. 2G, 2H, and FIG. 7C and FIGS. 9A-9D]. To address whether endogenous c-kit cells were coupled to host or chimeric cells, the expression of connexin-43 and N-cadherin was tested; c-kit cells formed gap junctions and mechanical connections via these proteins with other c-kit cells as well as with GFP$^{pos}$ MSCs (FIGS. 2I, 2J). These cell-cell interactions closely resemble cardiac stem cell niches. Further immunohistochemical characterization demonstrated that a number of these cells co-expressed MDR1 and GATA-4, indicating the commitment to cardiac lineage within the regenerated niches. There was a 25-fold increase in the number of these cardiac lineage committed c-kit cells in the border zones of the αMSCs treated animals, compared to animals receiving injection of non-cellular vehicle alone, and to untreated control animals. No differences were noted in the infarcted and non-infarcted zones, indicating the presence of an active endogenous repair mechanism in the border zones of the treated hearts (FIGS. 10A-10C). These findings introduce a novel mechanism underlying MSC treatment which, in addition to regenerating chimeric myocardial tissue within the first two weeks after transplantation, also now is shown to orchestrate a program of endogenous cardiac repair comprising an influx of c-kit$^{pos}$ cells with lineage commitment to the myocytes phenotype and through the formation of structures resembling cardiac stem cell niches.

Figure 3A:
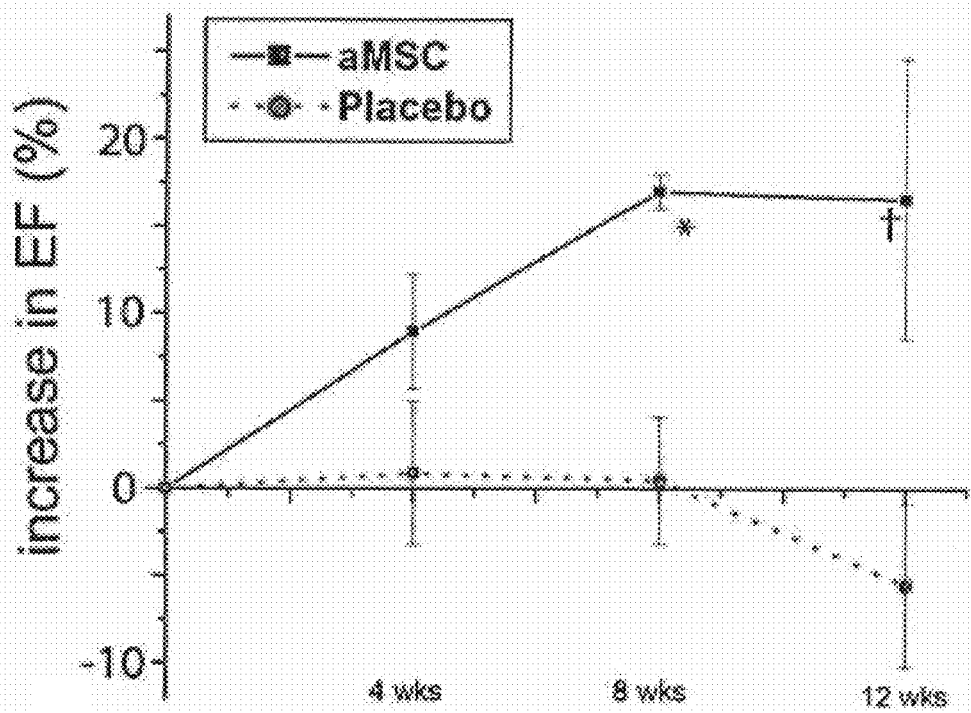
FIGS. 3A to 3J show the long-term functional recovery following αMSCs transplantation.
Figure 3B:
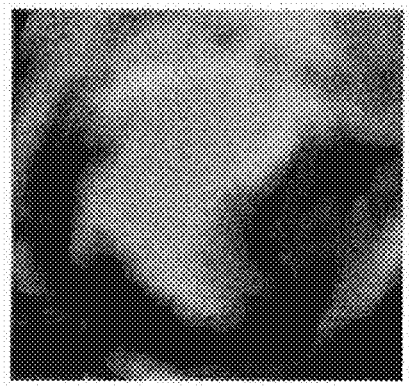
Figure 3C:
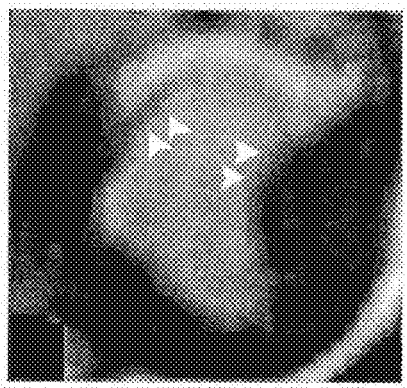
Figure 3D:
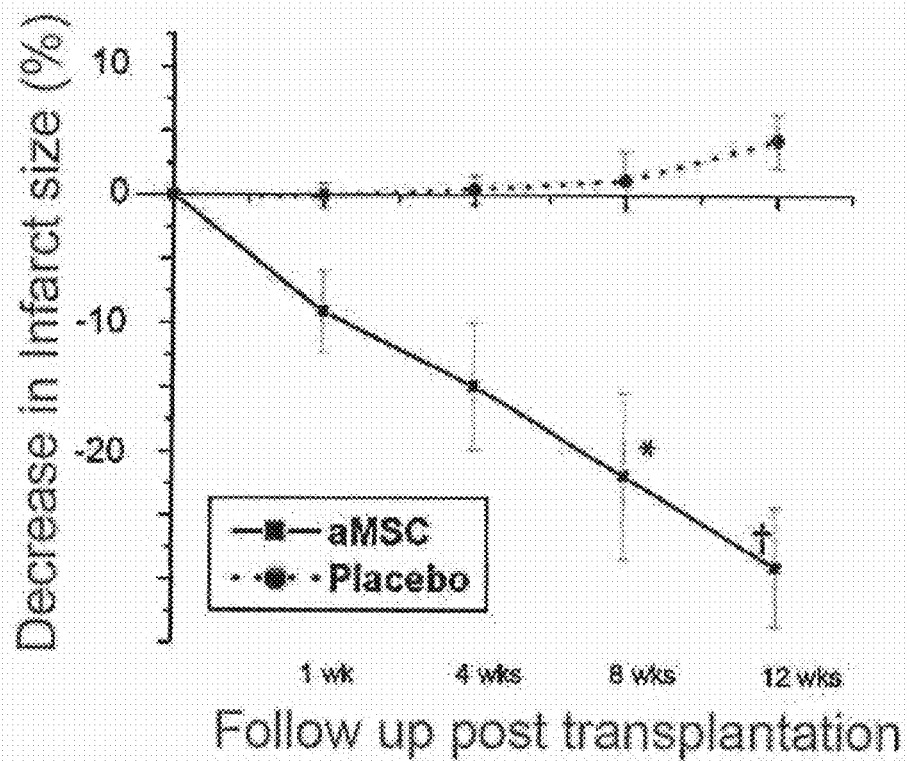
Figures 3E, 3F:
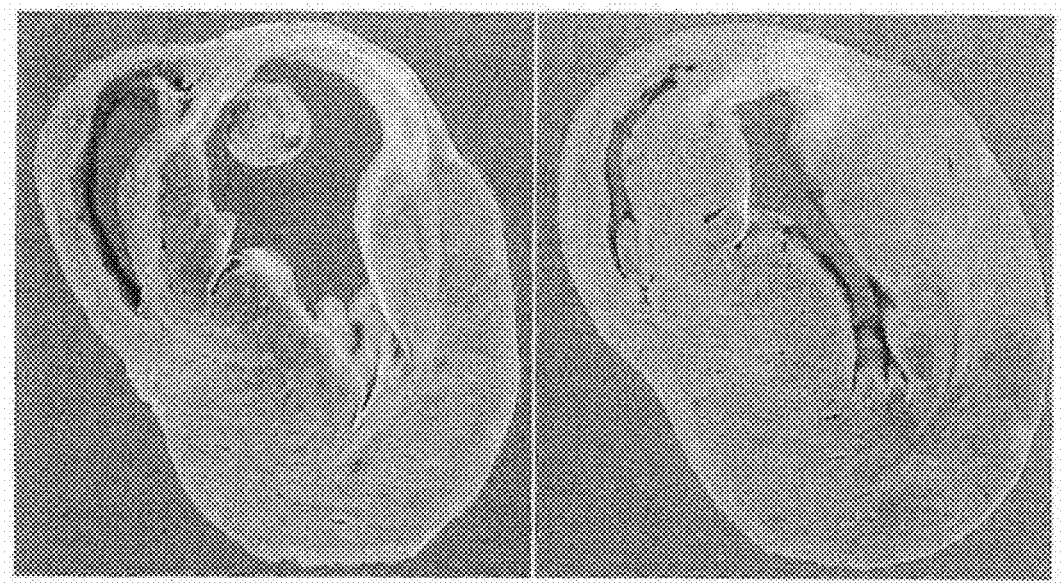
Figure 3G:
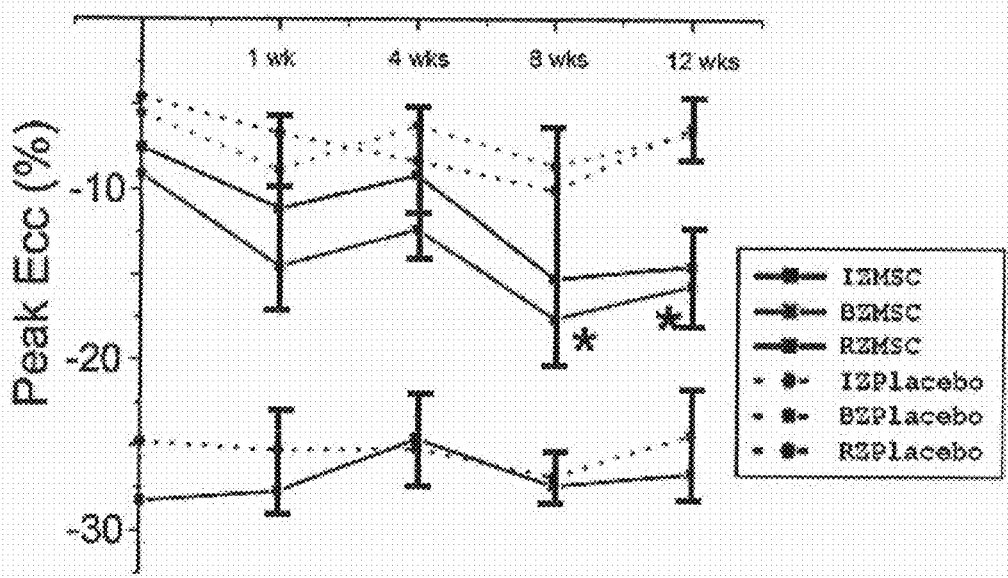
Figure 3H:
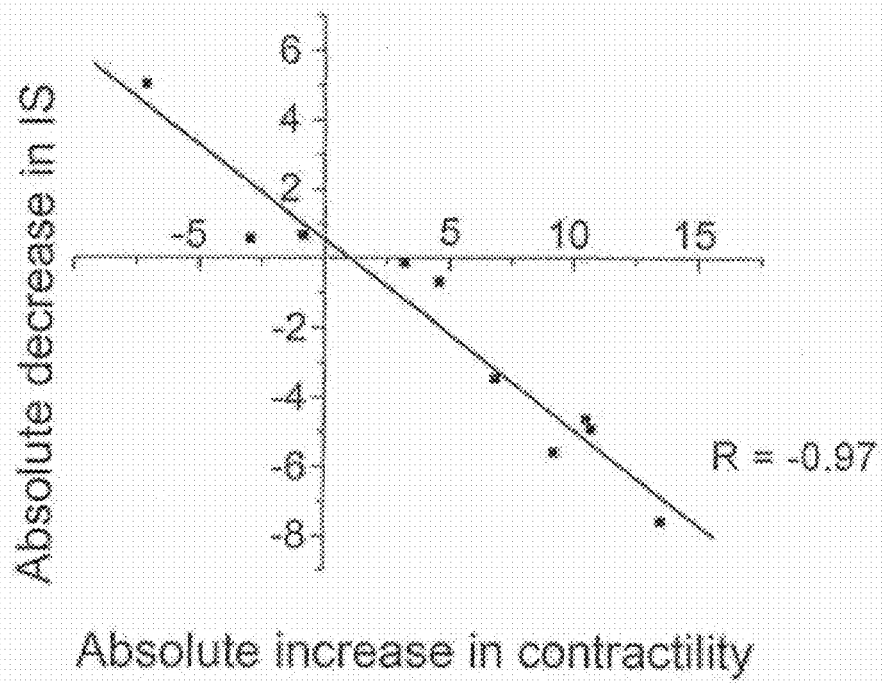
Figure 3I:
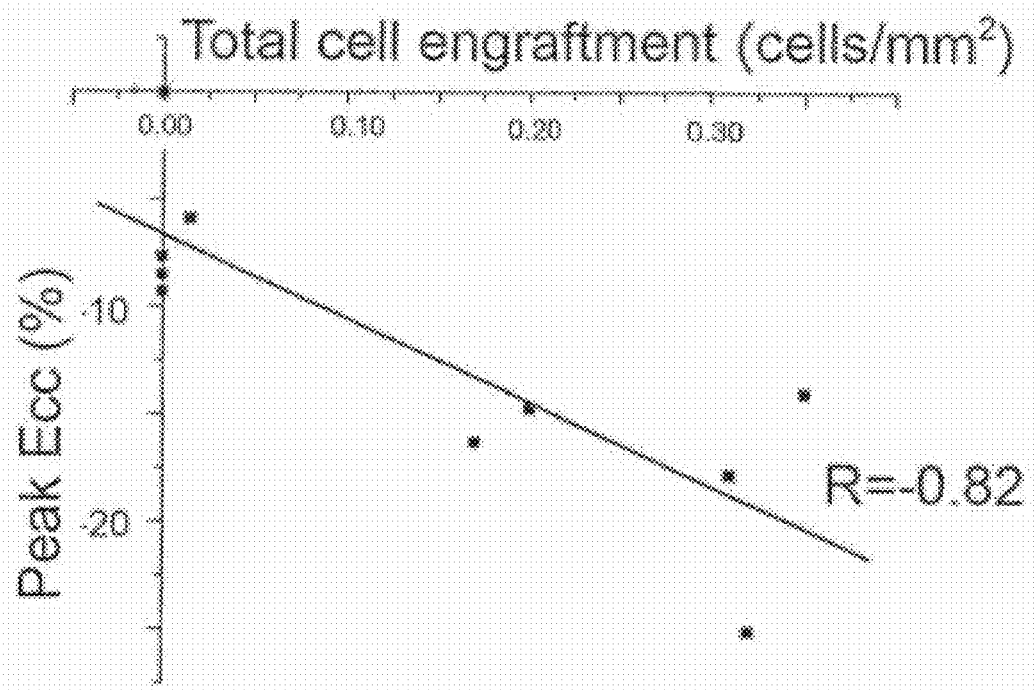
Figure 3J:
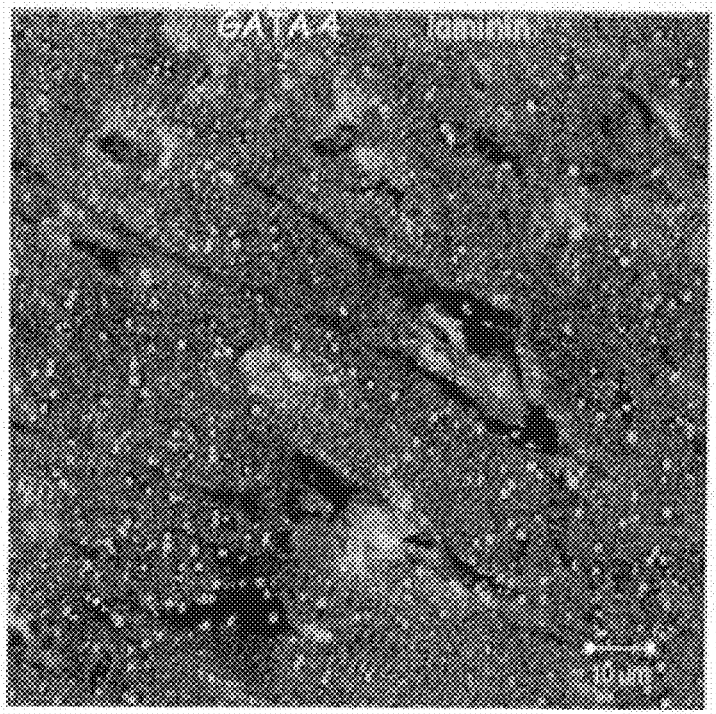

Next long-term αMSC engraftment and contribution to functional cardiac recovery, late after infarction was examined. BrdU-labeled male αMSCs were injected into female animals that had sustained myocardial infarction 3 months prior. These animals were studied for 3 months following cell injection by serial cardiac MRI, followed by histologic evaluation. Three months after MI, pigs had diminished ejection fractions (33.4±1.0% vs 47.7±2.0% at baseline; p=0.008), the infarction scar comprised 18.3±2.5% of the ventricle, and significant regional dysfunction of the scar segment was documented using MR tagging (FIGS. 3A-3J). Intramyocardial injection of αMSCs three months after MI produced substantial increases in ejection fraction, reductions in scar, and restored regional cardiac function in the border zones of the scar corresponding to the regions of scar reduction (FIGS. 3A-3H). Importantly, the reduction in scar size correlated closely with regional functional recovery (FIG. 3H).

Figure 11A:
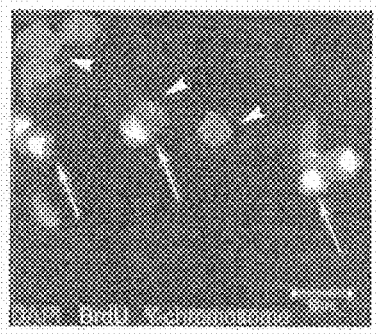
FIGS. 11A to 11C show the long-term retention of αMSCs.
Figure 11B:
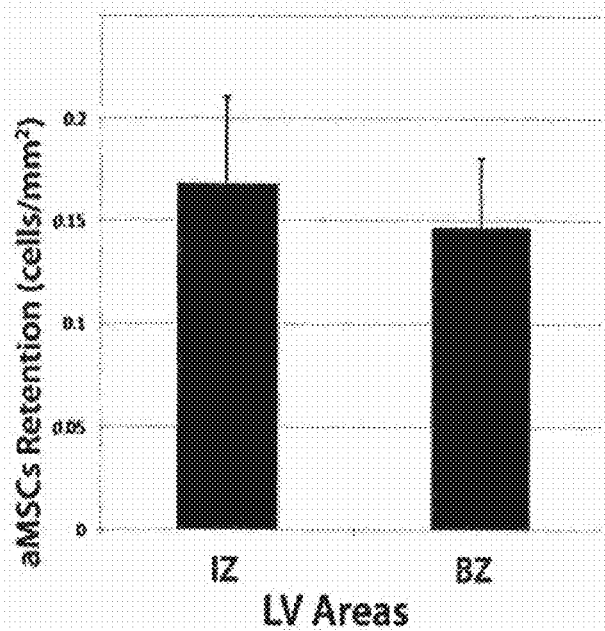
Figure 11C:
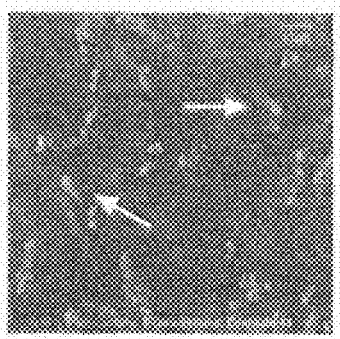
Figures 12A, 12B, 12C, 12D:
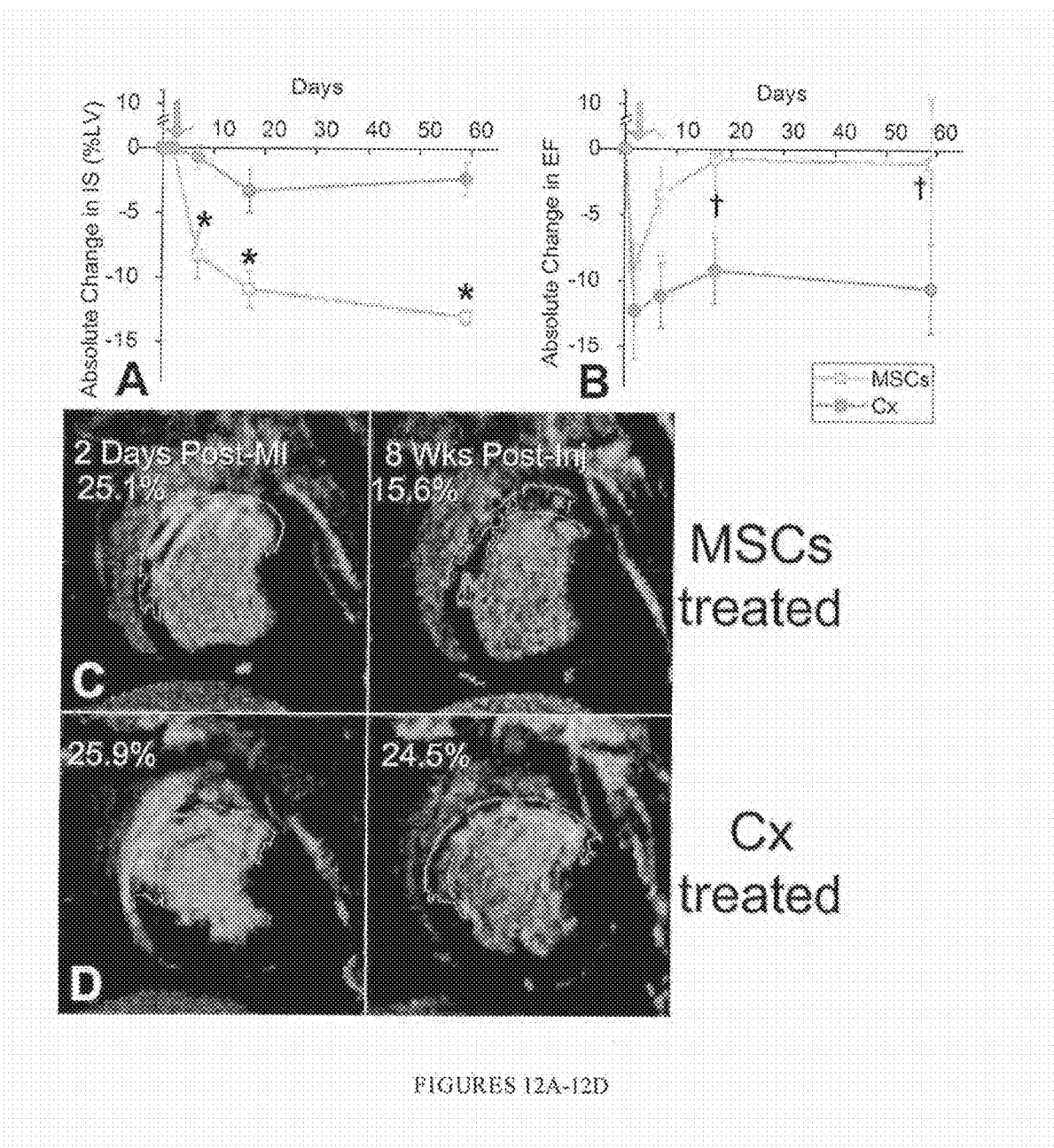
FIGS. 12A-12D: Assessment of infarct size and global LV function by cardiac MRI.

The hearts were analyzed by immunohistologic examination to test whether this functional recovery required cell engraftment. Y chromosome containing cells ($Y^{pos}$) were present in the infarct and border zones of the αMSC-treated group, but were not detected in the placebo group, nor in the remote zones of the αMSC-treated animals. The density of $Y^{pos}$ cells did not differ between the infarct zone (0.17±0.04 cells/mm$^2$) and border zone (0.15±0.03 cells/mm$^2$) (FIGS. 11A, 11B) Co-staining with cardiac-specific transcription factor GATA-4 and α-sarcomeric actinin showed that 14.0±4.0% of $Y^{pos}$ cells had an adult cardiac myocyte phenotype. Interestingly, $Y^{pos}$ cells of donor origin also exhibited putative gap junction formation with resident cardiomyocytes, as indicated by expression of connexin-43 (FIG. 11C). Importantly, the total number of $Y^{pos}$ cells engrafted in the BZ correlated with the improvement in the peak systolic circumferential strain (Ecc) (r=0.8; p=0.03) (FIG. 3I), indicating a critical contribution of cell engraftment and differentiation to the degree of functional recovery.

Figure 4E:
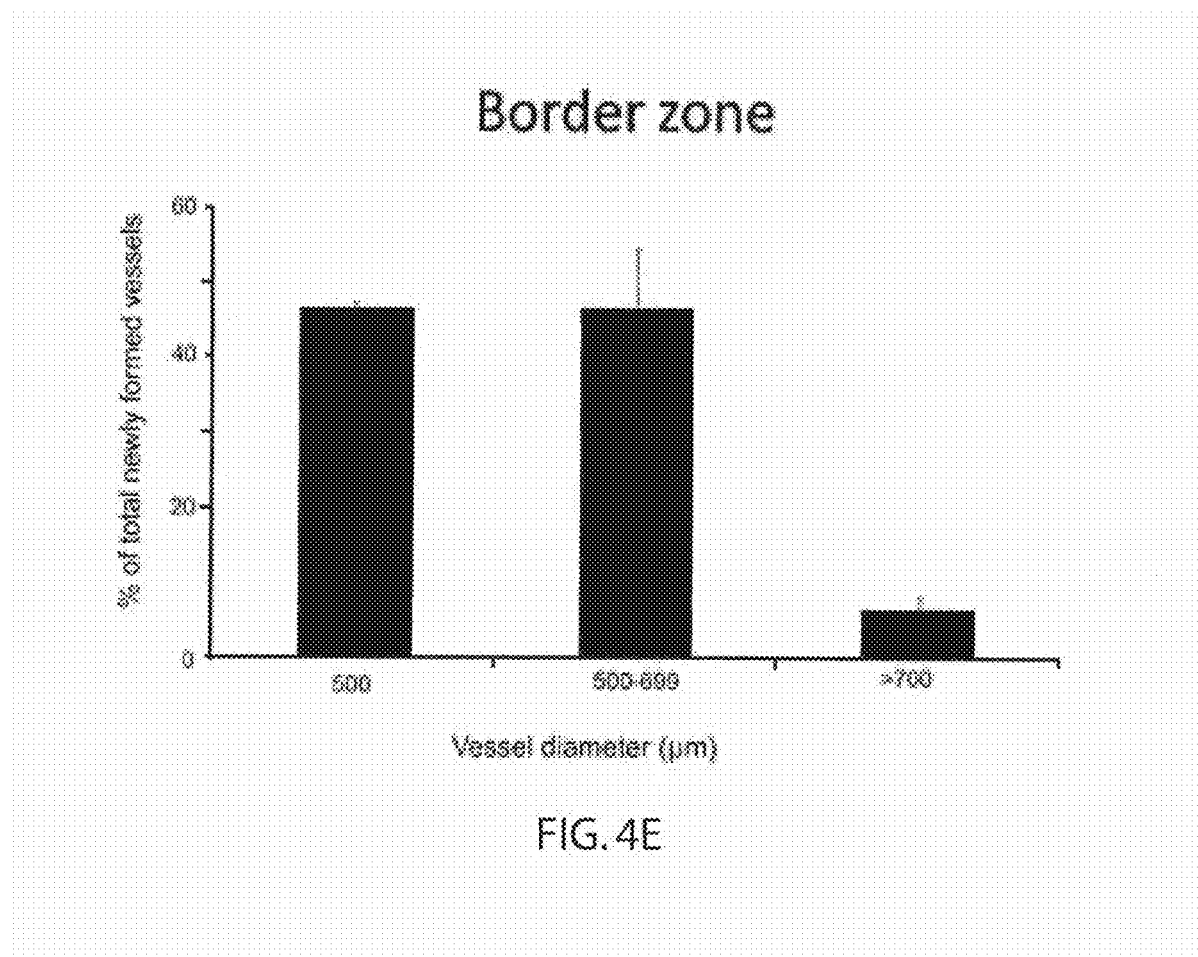

$Y^{pos}$ cells were also present in both large and small vascular structures, supporting participation in new vessel formation in IZ and BZ. Donor cells differentiated into both vascular muscle and endothelial lineages, as evidenced by co-localization of α-smooth muscle actin and factor VIII, respectively (FIGS. 4A, 4C). An overall of 9.9±2.4% of the Ypos cells were incorporated into vessel walls, with 5.9±1.9% co-expressing Factor VIII and 4.0±1.6% α-smooth muscle actin. The density of newly-formed vessels was calculated in vessel length per cubic millimeter. In IZ, the density of the cells was 0.05±0.01 mm/mm$^3$ and in the BZ it was similarly 0.04±0.02 mm/mm$^3$ (FIG. 4D). In BZ αMSCs were incorporated mostly in large and medium size vessels (500 μm$^{-1}$ mm, FIGS. 4A, 4B, 4D, 4E) composed of both endothelial and smooth muscle layers, illustrating their capacity to restore blood flow through large coronary vessels formation. In IZ, most of the new vessels had <20 μm diameter and were composed of single endothelial layers without smooth muscle layers, consistent with capillary formation.

Not all patients with heart disease may be able to receive effective autologous cell-based therapies, since age and host diseases may affect the quality of the autologous grafts per se. MSCs on the other hand, are a true stem cell population with known immunomodulatory and immuno-tolerogenic capacities that are a safe and successful cardiac allograft. MSCs meet all the expectations of a cell product that can be readily available in therapeutic quantities, thus providing an "off-the shelf" cell-based therapy for treating heart disease.

Together these findings demonstrate that allogeneic MSCs, unaltered to enhance their survival, engraft and exhibit trilineage cardiac cell differentiation. The repair process is driven by damage signals, and occurs both in acute and in chronic myocardial infarction. MSC engraftment is accompanied by the formation of cell-cell interactions both with host adult cells and with host endogenous precursor cells. The latter reconstitutes multi-cellular clusters that have the features of stem cell niches and promotes the migration and myocytic differentiation of endogenous cardiac precursor cells. Within 72 h the fate of the allografts is determined, and the level of regeneration is preserved up to three months after transplantation. The degree of engraftment correlates with recovery of cardiac function, which is substantial, and with reduction in myocardial scar formation. While scar reduction is incomplete, these findings raise the possibility that strategies involving repeated αMSCs applications or acceleration of their differentiation rates could result in near total elimination of cardiac scar. The public health impact of an effective treatment for chronic ischemic cardiomyopathy is immense, and these data are the first to indicate such a potential for MSC therapy. The totality of these findings document an impressive capacity of an adult bone marrow derived stem cell to repair acutely and chronically injured hearts, and have important mechanistic and clinical implications.

Example 2: Bone Marrow Mesenchymal Stem Cells Stimulate Cardiac Stem Cell Proliferation and Differentiation Methods This study was reviewed and approved by the University of Miami Institutional Animal Care and Use Committee and complies with all Federal and State guidelines concerning the use of animals in research and teaching as defined by The Guide For the Care and Use of Laboratory Animals (NIH Pub. No. 80-23, revised 1985).

Mesenchymal Stem Cell Isolation, Harvest and Labeling: Swine MSCs were isolated and expanded from a single, healthy male Yorkshire donor as previously described. Briefly, bone marrow was obtained from the iliac crest, and aspirates were passed through a density gradient to eliminate undesired cell types and were plated with 25 ml MEM Alpha media (Mediatech, Manassas, Va.) containing 20% fetal Bovine Serum (Hyclone, Logan, Utah) in 162 cm$^2$ culture flasks (Fisher Scientific, Pittsburgh, Pa.). At 5-7 days after plating, non-adherent cells were washed away during medium changes and the remaining, plastic adherent, purified MSC population was expanded in culture. The MSC population was then harvested and transduced with 5-Bromodeoxyuridin (BrdU) or green fluorescent protein (Lenti-GFP vector, Lentigen) according to manufacturers' instructions. All used cells were harvested when they reached 80-90% confluence at passage. Labeled MSCs were placed in a cryopreservation solution consisting of 10% DMSO, 5% porcine serum albumin, and 85% Plasmalyte. Cells were placed in cryo bags at a concentration of 5-10 million MSCs/ml and frozen in a control-rate freezer to −180° C. until the day of implantation. By using trypan blue staining, the viability of all thawed MSC lots was verified to be >85% before use in the study.

Organotypic Cultures: Cardiac biopsies were collected from the right ventricular septal wall of 7 Yorkshire swine with or without myocardial infarction. The biopsies were harvested and kept in cold Hank's Balanced Salt Solution (Lonza) containing 1% penicillin/streptomycin until processing. After washing thoroughly with DMEM (GIBCO), samples were minced in ~1 mm$^3$ cubes and digested in a solution of DMEM/F12 (GIBCO), 20% FBS, 1% penicillin/streptomycin and 200 units/ml Collagenase-Type II solution (Worthington) at 37° C. for 3 h. Following that, whole lysates were collected, washed twice with DMEM, resuspended in DMEM/F12, 20% FBS, 1% penicillin/streptomycin and plated in T-25 tissue culture flasks (Corning) that contained 2-3×10$^5$ GFP+ porcine MSCs or not. After 1 week, samples were collected by trypsinization and c-kit$^+$ cells were purified by repeated immune panning in a Petri dish as previously described. After 2-3 days in culture, the isolated c-kit$^+$ cells were trypsinized and re-plated in a Petri dish containing F12K (GIBCO), 5% FBS, 10 ng/ml bFGF (peprotech), 20 ng/ml LIF (Sigma) and 1% penicillin/streptomycin where they grew for 7-10 days. Next, only the non-adherent fraction was collected and expanded as semi-adherent cells in tissue culture dishes containing DMEM/F12, 2% FBS, Insulin-Transferrin-Selenite (Sigma), 10 ng/ml bFGF, 10 ng/ml LIF, 20 ng/ml EGF (peprotech), 100 ng/ml SCF (Peprotech) and 1% penicillin/streptomycin. Subsequent immunocytochemical evaluation was performed on cytospin preparations according to manufacturers' instructions (Sakura Finetek).

In vitro differentiation assays: To test the differentiation capacity of CPCs into cardiac myocytes, co-cultures were performed with neonatal rat cardiac myocytes (NRCMs). Briefly, NRCMs were isolated as previously described and plated at a density of 1×10$^5$ NRCMs/cm$^2$ in 12-well plates (Corning) containing collagen-coated glass coverslips. CPCs were then co-cultured with NRCMs in a 1/3 ratio, directly or indirectly using transwell inserts with a 0.4 µm pore size (BD). Cocultures were maintained with NRCM medium consisting of DMEM (GIBCO), insulintransferrin-selenite (Sigma), 2 mg/ml bovine serum albumin, 20 µg/ml ascorbic acid, 1% penicillin-streptomycin and incubated for up to 2 weeks in humidified incubator at 37° C. and 5% $CO_2$. For immunocytochemical evaluation, cells were fixed in 4% paraformaldehyde for 20 min at RT, 24 h, 72 h and 2 weeks after plating.

Induction of Myocardial Infarction and transendocardial Injections: Thirty one healthy female Yorkshire swine weighed 25-35 kg, were included in this study. Experimental myocardial infarction was generated according to our previously described protocols. Briefly, the right common carotid artery was canulated under anesthesia induced with ketamine (33 mg/kg, IM) and maintained with isoflurane (1.5-2.0%). MI was induced by accessing the Left Anterior Descending (LAD) coronary artery and occluding it after the first diagonal branch by inflating a coronary angioplasty balloon (2.75×15 mm) for 60 min followed by reperfusion. All animals were adequately heparinized during the procedure. The study was conducted in 2-phases. In the first phase, it was sought to explore the mechanisms underlying MSCs-based cardiac repair, therefore animals received intramyocardial injections of allogeneic GFP labeled porcine MSCs (75×10$^6$ cells) or Placebo (Plasmalyte alone, Baxter Edwards Critical Care, Deerfield, Ill.), three days after MI.

The second phase was designed to address whether MSCs-implantation is necessary for successful cardiac repair or their secreted factors alone could exert similar effects; therefore animals were randomized to receive intramyocardial injections of allogeneic GFP labeled porcine MSCs (100×10$^6$ cells) or the rich in secreted factors conditioned medium were the MSCs had been expanded into, concentrated 10× (Stirred Cell, Millipore). All investigators involved in this study were blinded. All injections were performed under fluoroscopy, with a pistol-needle tip injection catheter advanced to the LV through a steerable guide catheter (Stiletto, Boston Scientific, Natick, Mass.). Hypokinetic, akinetic, and dyskinetic areas were identified during contrast ventriculography, and injections were performed within and at the borders of the dysfunctional area, as defined by bi-plane ventriculography. A total of 15 injections were performed in each animal, with each injection containing 0.5 ml of the injectate. Each injection was fluoroscopically guided to distribute cells evenly throughout the entire infarct and border zones.

Cardiac MRI: For the second phase, therapeutic effect on cardiac function was assessed by Cardiac MR imaging (cMRI). Cardiac structure and function were monitored at baseline, 1 day prior to injections, 4 days, 2 weeks and 8 weeks post-injections. Serial cMRI images were acquired with a four channel phase array, 1.5 T MR Scanner (Siemens Symphony, Erlangen, Germany) in anesthetized animals with electrocardiography gating and short breath-hold acquisition. The protocol for cine-cMRI and tagging-cMRI has been described before. Briefly, LV Global function was assessed in steady state free precession with a number of slices to cover the entire LV from apex to base. Imaging parameters were as follow: Echo delay time (TE)=1.9 ms, repetition time (TR)=4.2 ms; flip angle 45°; 256×160 matrix; 8 mm slice thickness/no gap; 28 cm field of view (FOV) and 1 number of signal average (NSA). Cine images were analyzed with research comprehensive software validated by the Cardiology MR group at Lund University, Sweden (segment.heiberg.se).

The protocol included an intravenous bolus of Gadolinium-DTPA (0.1 mmol/kg, 5 m/s; MAGNEVIST™, Berlex, Wayne) through a peripheral intravenous line. Images were acquired 15 minutes later at the same location as the short axis cine-images. Imaging parameters were TR=7.3, TE=3.3, TI=200 ms; flip angle=25°, 256×196 matrix; 8 mm slice thickness gap 31.2 kHz, 28 cm FOV and 2 NSA.

Histology: For the first phase of the study, microscopic evaluation between the treated (n=3), placebo (n=3) and control (n=3) Yorkshire pigs was performed at 2 weeks after the intramyocardial injections. Moreover, in order to assess the time course of MSCs engraftment and differentiation, 8 more animals were sacrificed at 24 h (n=2 placebo and n=2 MSCs treated) and 72 h (n=3 placebo and n=3 MSCs treated) post-injections. For the second phase of the study, microscopic evaluation between the MSCs and Cx-treated pigs was performed at 2 weeks (n=3 each) and 8 weeks (n=3 each) after TEIs. All animals were humanely euthanized through intravenous infusion with KCL to arrest the hearts in diastole. The explanted hearts were then washed in ice-cold phosphate buffer saline (PBS) to remove any residual blood, followed by perfusions through the left and right coronary arteries with 10% buffered formalin. Heart chambers were then filled with dental impression material (Imprint, 3M ESPE) to preserve heart's shape during fixation. The hearts were then fixed for 24 h in 10% buffered formalin and sliced transversely into seven to eight ~4 mm thick slices using a commercial meat cutter, weighted and digitally photographed. Representative samples were selected from the infarcted (IZ), border (BZ) and remote areas (RZ) of each slice, and embedded in paraffin (FFPE) for immunohistochemical evaluation. Hematoxylin and Eosin (H&E), as well as Masson's Trichrome staining were used for the primary histological examination. For confocal immunofluorescence quantification, 4-5 µm thick FFPE slides from each region (IZ, BZ, RZ) were evaluated. The total numbers of positively-stained cells were quantified per slide to calculate the number of cells per unit volume ($cm^3$) on each sample. Morphometric analysis was performed by using a custom research package (Image J, NIH, Bethesda, Md.).

Immunofluorescence Confocal Microscopy: Immunofluorescence studies were carried out on 4 µm-thick paraffin sections, according to previously described protocols. Briefly, after deparaffinizing and rehydrating the tissue sections, antigen unmasking was performed by microwaving the slides for 20 min in citrate buffer Solution, pH=6 (Dako, Carpenteria, Calif.). The sections were blocked for 1 h at RT with 10% normal donkey serum (Chemicon International Inc, Temecula, Calif.), followed by 1 h incubation at 37° C. with the primary antibody. The following antibodies were used: C-kit, α-sarcomeric actinin, α-smooth muscle actin, α-smooth muscle myosin heavy chain, Connexin-43 (Sigma, Saint Louis, Mo.), N-cadherin, anti-GFP, Laminin, Phospho-Histone H3, cardiac troponin-I (Abcam, Cambridge, Mass.), GATA-4, MDR1, VE-cadherin, CD3, CD14, CD68 (Santa Cruz Biotechnologies, Santa Cruz, Calif.), activated Caspase-3 (BD Biosciences, San Jose, Calif.), Nkx2.5 (R&D systems Inc, Minneapolis, Minn.), Factor VIII-related antigen (Biocare Medical, Concord, Calif.), Isl-1 (40.2D6, Developmental Studies Hybridoma Bank, Iowa), cardiac myosin light chain-2 (Novus Biologicals, Littleton, Colo.) and KDR (Cell Signaling, Boston, Mass.). Consequently, the antibodies were visualized by incubating the sections for 1 h at 37° C. with FITC, Cy3 and Cy5-conjugated $F(ab)_2$ fragments of affinity-purified secondary antibodies (Jackson Immunoresearch, West Grove, Pa.). Slides were counterstained with DAPI, mounted with Pro-Long Antifade Gold reagent (Invitrogen, Carlsbad, Calif.) and stored at 4° C. until further examination. Microscopic evaluations and image acquisitions were performed with a Zeiss LSM-510 Confocal Microscope (Carl Zeiss MicroImaging, Inc. Thornwood, N.Y.). The Zeiss Axiovision software (release 4.7.1.0, Carl Zeiss Imaging Solutions, GmbH) was used for 3D rendering of the confocal Z-stack images.

Fluorescence in Situ Hybridization: Fluorescence in Situ Hybridization (FISH) was employed to detect the Y-chromosome of the sex-mismatched transplanted allogeneic MSCs in the female porcine hearts. The Y-chromosome containing cells were detected by hybridizing the tissue samples with Cy3-conjugated porcine Y chromosome paints (StarFISH, Cambio Ltd, Cambridge, UK) according to manufacturers' instructions. Briefly, following deparaffinization and rehydration, the samples were microwaved for 20 min in citrate Buffer, pH=6 (Dako). After cooling for 30 min at RT, tissues were digested for 3 min at 37° C. with pepsin, washed with 2×SSC buffer (Invitrogen) and dehydrated through serial ethanol washing steps. The samples were air-dried and the probe was applied. After covering the samples with a coverslip and sealing them with rubber cement, the samples were placed in the hybridizer (Dako) for denaturation (10 min at 80° C.) followed by overnight hybridization at 37° C. The next day, samples were washed with 2×SSC, mounted with DAPI and covered as previously described.

Statistical Analysis: All the values are presented as means±SEM. All analyses were performed by using the SPSS for Windows version 15.0 (SPSS Inc., Chicago, Ill.). Differences between groups following immunohistological evaluation were compared by using One Way ANOVA. Differences between groups in ejection fraction and infarct size based on cMRI were calculated by using two-way repeated measures ANOVA. The Tukey's test was used for the post-hoc analysis. A level of $P \leq 0.05$ was considered statistically significant.

Results:

Although the heart has regenerative potential, it is insufficient to restore functioning myocardium after injury. Cell-based therapies intent to overcome this limited endogenous repair capacity, by directly replacing damaged tissue. Without wishing to be bound by theory, it was hypothesized here, that they could also ameliorate myocardial senescence. The data show that bone marrow mesenchymal stem cells (MSCs) engraft and differentiate into cardiomyocytes, but to a much greater extent stimulate innate cardiopoietic mechanisms. MSCs couple with host myocardium, participate in cell-cell interactions, and enhance endogenous c-kit$^+$ cardiac precursor cell (CPCs) amplification and cardiac lineage commitment. In vitro, MSCs stimulate c-kit$^+$ CPCs to proliferate into enriched populations of adult cardioblasts from which differentiated spontaneously contracting cardiomyocytes arise. MSCs can be used to stimulate host CPCs, a new mechanism of action underlying successful cell-based therapeutics.

It was also hypothesized herein, that MSCs stimulate cardiac repair through cell-autonomous effects that stimulate host myocardial precursor cells to amplify and differentiate into cardiomyocytes. To address this prediction, $100 \times 10^6$ GFP-labeled, male porcine MSCs were injected into the infarct and border zone in female pigs 3 days following myocardial infarction (MI); another group received injection of concentrated conditioned medium (CCM), so as to test whether secreted factors alone would be sufficient to stimulate host cardiac repair.

As shown by serial cardiac magnetic resonance imaging (cMRI), MI was accompanied by a reduced ejection fraction (EF) [27.9±1.13% and 25.8±3.1% for MSC and CCM groups respectively, p=NS, p<0.001 vs baseline] and scar tissue that comprised ~25% of the left ventricle (25.4±2.2% and 24.7±2.9% of the left ventricles of the MSC and CCM groups, respectively, p=NS) (FIGS. 12A-12D). MSC-treatment decreased infarct size as early as 4 days after implantation achieving ~50% reduction in scar size by 8 weeks. By 2 weeks EF had improved significantly, reaching normal function by week 8 (FIGS. 12A-12D). In contrast, treatment with CCM did not produce significant structural or functional improvements, indicating a dependence upon the cells for sustained cardiac repair.

Confocal immunofluorescence was employed to detect GFP and Y chromosome labeled cells in infarct (IZ) and border (BZ) zones of the myocardium (FIGS. 16A-16D) and 1,585±746 and 1,317±393 cells/cm$^3$ were detected 1 and 3 days post-implantation, respectively. As early as 1 day after injection, MSCs entered the cell cycle, evidenced by the mitotic marker of serine-10 phosphorylated histone-H3 (Phospho-H3), and exhibited minimal apoptosis, as evidenced by the pro-apoptotic marker activated caspase-3 (FIGS. 16A-16D).

While MSCs lacked of any marker of cardiovascular lineage in vitro, their commitment into cardiomyocytes began to occur within 24 hours and by 2 weeks they had differentiated into new, mature cardiomyocytes and vascular structures (FIGS. 13A-13E). Chimeric myocardium was detected throughout IZ and BZ but not in the remote zones of the treated hearts (FIGS. 13A-13E). Quantification of Y-chromosome containing cardiomyocytes illustrated that the lineage commitment of MSCs was persistent from 3 days throughout the 2 month period of the study, and similar numbers of MSCs that had differentiated into myocytes were detected during this time (FIGS. 13A-13E; FIG. 14A). Immunophenotypic characteristics of porcine MSCs before transplantation were shown by immunocytochemical staining of the porcine MSCs illustrating their native phenotype; all cells were negative for markers such as GATA-4, KDR, isl-1, CD68, MDR1 and c-kit. Porcine Peripheral Blood Mononuclear Cells (PBMCs) used as a control cell type, for evaluating the aforementioned markers. PBMCs were negative for GATA-4 and Is1-1, but contained positive fractions for KDR, c-kit, CD68 and MDR1.

Next, the impact of MSCs on endogenous CPCs was addressed, as identified by the expression of the stem cell factor-receptor, c-kit. It was first confirmed that the detected c-kit$^+$ cells lacked GFP or the y-chromosome, confirming their endogenous origin (FIGS. 14A-14H). Quantification of c-kit$^+$ cells in infarct hearts illustrated sporadic distribution during the first 3 days after transplantation that was not different between MSC and CCM groups. However, 2 weeks after the transendocardial injections, endogenous c-kit$^+$ CPCs increased 11-fold in MSC but not CCM treated animals (FIGS. 14A-14H; FIGS. 17A-17F). Importantly, CPCs were detected in clusters in the IZ and BZ of MSC treated animals, but they were found as rare isolated cells in remote areas as well as in the non-MSC treated hearts (FIGS. 14A-14H; FIGS. 17A-17F). In addition, CPCs formed potential gap junctions and mechanical connections with other c-kit$^+$ cells, adult cardiomyocytes, and with GFP$^+$ MSCs (FIGS. 14A-14H; FIGS. 17A-17F), and formed structures that resemble cardiac stem cell niches. Further immunohistochemical characterization demonstrated that a number of CPCs coexpressed MDR1 and GATA-4, indicating a cardiac lineage commitment (FIGS. 14A-14H). The number of cardiac committed CPCs was 2-fold increased in the IZ and 15-fold increased in the BZ of MSC-treated animals compared to animals receiving either CCM, non-cellular vehicle alone, and untreated controls. There were no differences between groups in the non-infarcted zones, indicating the presence of an active endogenous repair mechanism in the damaged zones of the treated hearts (FIGS. 14A-14H).

In vitro experiments were next performed to study the function of endogenous CPCs (FIGS. 15A-15K$_1$). The origin of c-kit$^+$ CPCs as well as their association to MSCs, was examined in ex vivo organotypic co-culture experiments. Fresh or cryopreserved endomyocardial biopsies from porcine hearts were cultured for one week with or without MSCs. In additional control experiments, MSCs were cultured under the same conditions without a myocardial biopsy. After 3 days, myocardial biopsies became infiltrated by MSCs and adhered to the MSC monolayers. In contrast, biopsies cultured without MSCs remained in suspension (FIGS. 15B, 15C). Within one week organotypic co-cultures became confluent, and purification by repeated immune panning illustrated that the number of GFP-negative, c-kit$^+$ cells egressing from the biopsy were 6-fold greater compared to biopsies cultured alone (FIGS. 15A, 15F). These cells were CD68$^{neg}$, small, semi-adherent and self-renewing (FIGS. 15D, 15H). As expected, c-kit$^+$ cells could not be harvested from MSC-control cultures. Similarly to our in-situ findings, immunocytochemical analysis documented the development of connexin-43 mediated cell-cell interactions between GFP$^+$ and c-kit$^+$ cells (FIG. 15G). In contrast, c-kit$^+$ cells purified from biopsies cultured without MSCs had a large, antigen-presenting cell-morphology that did not proliferate (FIG. 15E).

In contrast to previous studies, purification of c-kit$^+$ CPCs from single biopsy samples was dramatically accelerated by co-culture with MSCs, and facilitated an outgrowth of highly myocardiocytic CPCs; greater than 90% of the cells expressed the cardiac transcription factors Nkx2.5 and GATA-4 and the ATP-binding cassette transporter MDR1 while lacking expression of the VEGF-receptor, KDR (FIGS. 15A-15K$_1$). Interestingly, a fraction of the cells stained positive for the LIM-homeodomain transcription factor Is1-1 (FIG. 15J-15J$_2$], a marker that identifies a subset of CPCs during development of the embryonic heart, reported to withdraw from the post-natal heart. Importantly, isl-1 expression could not be detected in vivo and was absent from the c-kit+ CPCs found in the adult porcine myocardium. This finding corroborates previous reports, where the post-natal phenotype of c-kit+ CPCs represented a distinct population from the isl-1$^+$ CPCs. These observations highlight the capacity of MSCs to regenerate stem cell niches and signify a key role for c-kit and isl-1 that could link mechanisms between cardiac development and disease.

To test the capacity of the CPCs to differentiate into myocytes, cocultures with neonatal rat cardiomyocytes (NRCMs) were performed. Porcine CPCs were seeded on transwell membranes, and placed on top of NRCM monolayers. After 3-4 days in co-culture, CPCs differentiated into spontaneously contracting porcine cardiomyocytes, thus exhibiting their capacity to adopt fully differentiated cardiomyocytic lineages (FIG. 15I, FIGS. 17A-17F).

Here, it was demonstrated that extra-cardiac, bone marrow derived MSCs, when injected into hearts following myocardial infarction, facilitate cardiac recovery involving host cells as well as MSC engraftment and differentiation. Differentiation of MSCs occurs acutely after transplantation, while direct coupling with endogenous c-kit$^+$ CPCs causes the latter to amplify and differentiate into fully developed adult cardiomyocytes. This mechanism closely resembles cell-cell interactions between CPCs and stromal cells in the cardiac niche, which play a role for the regulation and expansion of the nascent cardiac stem cell pool. All findings were replicated ex-vivo and developed in-vitro cardiac niches that harbored CPCs previously found only in pre-natal hearts, conveying to important therapeutic potentials.

These findings introduce a novel approach to enhance endogenous cardiac repair by stimulating the proliferation and maturation of endogenous CPCs. This study illustrates how the hearts' own regenerative properties can be stimulated to facilitate cardiac recovery following myocardial infarction. The approach employed a cell-based rather than pharmacologic approach to enhance cardiac repair, and as such these results have important biological and therapeutic implications.

Importantly, these experiments have utilized a highly translational experimental model of ischemic cardiomyopathy thus reduce to practice methodologies which could greatly enhance manufacturing of adult cardioblasts from individual hosts. Last, these results offer insights into the mechanism of action of a cell-based therapy, whereby significant cardiac repair occurs in the absence of a degree of engraftment and differentiation sufficient to account for the degree of cardiac functional recovery. Together these findings support the concept that MSCs may replenish or restore cardiac stem cell niches lost or injured during myocardial infarction.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the Disclosure is provided to allow the reader to quickly ascertain the nature of the technical disclosure. It is submitted with the understanding that it will not be used to interpret or limit the scope or meaning of the following claims.

What is claimed is:

1. A method of treating heart disease or heart disorders in a patient comprising:
   purifying c-kit$^{pos}$ cardiac stem cells from a sample;
   mixing ex-vivo mesenchymal stem cells with the purified cardiac stem cells; and
   administering to a patient's cardiac tissue in vivo the mixture of mesenchymal stem cells and cardiac stem cells in a concentration effective to repair damaged cardiac tissue.

2. The method of claim 1, wherein the mesenchymal stem cells are autologous to the patient.

3. The method of claim 1, wherein the mesenchymal stem cells are multi-lineage stem cells.

4. The method of claim 3, wherein the mesenchymal stem cells differentiate into at least one lineage of cardiac cells.

5. The method of claim 3, wherein the mesenchymal stem cells differentiate into at least two lineages of cardiac cells.

6. The method of claim 3, wherein the mesenchymal stem cells differentiate into three lineages of cardiac cells.

7. The method of claim 3, wherein the lineages of cardiac cells are identified by at least one marker comprising cardiac transcription factor GATA-4; endothelial cell markers Factor VIII and KDR; vascular smooth muscle marker α-smooth muscle actin; or cardiomyocyte marker α-sarcomeric actinin.

8. The method of claim 1, wherein the mesenchymal stem cells are obtained from bone marrow, circulation or tissues and organs.

9. The method of claim 8, wherein the mesenchymal stem cells are isolated from adult bone marrow cells.

10. The method of claim 1, wherein the mesenchymal cells recruit endogenous cardiac stem cells, reconstitute myocardial stem cell niches and accelerate endogenous cell differentiation into myocytes.

11. The method of claim 1, wherein the purified cardiac stem cells are additionally identified by at least one further marker comprising connexin-43, N-cadherin, CD3$^{neg}$, CD14$^{neg}$ and CD68$^{neg}$.

12. The method of claim 1, further comprising administering mesenchymal stem cell factors to the patient.

13. A method of recruiting endogenous cardiac stem cells to damaged heart tissue in a patient comprising:
   administering to the damaged heart tissue in the patient a pharmaceutical composition comprising purified mesenchymal stem cells and purified c-kitpos cardiac stem cells,
   wherein the mixture recruits endogenous cardiac stem cells to the damaged heart tissue.

14. The method of claim 13, wherein the mesenchymal stem cells are purified from adult bone marrow.

15. The method of claim 13, wherein the mesenchymal stem cells are autologous, heterologous, syngeneic, allogeneic or xenogeneic to the patient.

16. The method of claim 13, wherein the purified cardiac stem cells are additionally identified by at least one further marker comprising connexin-43, N-cadherin, CD3$^{neg}$, CD14$^{neg}$ and CD68$^{neg}$.

17. The method of claim 13, wherein the damage to heart tissue comprises disease, physical damage, chemical damage, surgery, transplantation, or congenital defects.

18. A method of inducing cardiac stem cell proliferation comprising: isolating mesenchymal stem cells; co-culturing ex-vivo mesenchymal stem cells and c-kit$^{pos}$ cardiac stem cells in a concentration sufficient to induce cardiac stem cell proliferation in a patient.

19. The method of claim 18, wherein the cardiac stem cells differentiate into cardiac cells expressing at least one of MDR1 or GATA-4.

20. The method of claim 18, wherein the cardiac stem cells are derived from an autologous or histocompatible tissue biopsy, heterologous, syngeneic, allogeneic or xenogeneic to the patient.

21. The method of claim 18, further comprising administering the cardiac stem cells to the patient.

22. The method of claim 18, wherein the mesenchymal cells and cardiac tissue are autologous, heterologous, syngeneic, allogeneic or xenogeneic to the patient.

23. The method of claim 18, wherein isolated mesenchymal stem cells and cardiac tissue are isolated from differing sources.

24. The method of claim 18, wherein the cardiac stem cells are additionally identified by at least one further marker comprising connexin-43, N-cadherin, CD3$^{neg}$, CD14$^{neg}$ and CD68$^{neg}$.

25. The method of claim 18, wherein the mesenchymal cells are autologous stem cells and are administered to the patient in a therapeutically effective dose to recruit endogenous stem cells to damaged tissue.

26. A method of treating heart disease or heart disorders in a patient comprising:
   mixing mesenchymal stem cells with purified c-kitpos cardiac stem cells ex vivo to produce a cell mixture; and
   administering the cell mixture to a patient's cardiac tissue in vivo in a concentration effective to repair damaged cardiac tissue.

27. The method of claim 26, wherein the administered cardiac stem cells differentiate into cells having at least one marker comprising cardiac transcription factor GATA-4; endothelial cell markers Factor VIII and KDR; vascular smooth muscle marker α-smooth muscle actin; or α-sarcomeric actinin.

28. The method of claim 26, wherein the mesenchymal stem cells are obtained from the group selected from bone marrow, circulation, tissues, organ and combinations thereof.

29. The method of claim 28, wherein the mesenchymal stem cells are isolated from adult bone marrow cells.

30. The method of claim 26, wherein the mesenchymal cells recruit endogenous cardiac stem cells, reconstitute myocardial stem cell niches and accelerate endogenous cardiopoesis.

31. The method of claim 26, wherein the mesenchymal stem cells are autologous, heterologous, syngeneic, allogeneic or xenogeneic to the patient.

32. The method of claim 26, wherein the damage to heart tissue comprises disease, physical damage, chemical damage, surgery, transplantation, or congenital defects.

33. The method of claim 16, wherein the cardiac stem cells differentiate into cardiac precursor cells.

34. The method of claim 18, wherein the cardiac stem cells differentiate into cardiac precursor cells.

35. The method of claim 26, wherein the number of mesenchymal cells is one million.

36. The method of claim 26, wherein the method comprises administering 20-50 µl of mesenchymal stem cells at a concentration of $10\text{-}40\times10^6$ MSCs/ml.

37. The method of claim 1, wherein the mesenchymal stem cells are allogenic to the patient.

38. The method of claim 1, wherein the administration of the mixture increases ejection fraction of the patient's heart.

* * * * *